(12) United States Patent
Yarmush et al.

(10) Patent No.: US 11,136,553 B2
(45) Date of Patent: Oct. 5, 2021

(54) ISOLATED ADULT CELLS, ARTIFICIAL ORGANS, REHABILITATED ORGANS, RESEARCH TOOLS, ORGAN ENCASEMENTS, ORGAN PERFUSION SYSTEMS, AND METHODS FOR PREPARING AND UTILIZING THE SAME

(71) Applicants: THE GENERAL HOSPITAL CORPORATION, Boston, MA (US); MASSACHUSETTS INSTITUTE OF TECHNOLOGY, Cambridge, MA (US)

(72) Inventors: Martin Yarmush, Newton, MA (US); Basak E. Uygun, Cambridge, MA (US); Korkut Uygun, Cambridge, MA (US); Maria-Louisa Izamis, Boston, MA (US); Alejandro Soto-Gutierrez, Boston, MA (US); Herman Tolboom, Zurich (CH); Hiroshi Yagi, Brookline, MA (US); Carley Shulman, Sudbury, MA (US); Jack Milwid, Denver, CO (US)

(73) Assignees: Massachusetts Institute of Technology, Cambridge, MA (US); The General Hospital Corporation, Boston, MA (US)

(*) Notice: Subject to any disclaimer, the term of this patent is extended or adjusted under 35 U.S.C. 154(b) by 0 days.

(21) Appl. No.: 14/645,527

(22) Filed: Apr. 7, 2015

(65) Prior Publication Data
US 2015/0322404 A1 Nov. 12, 2015

Related U.S. Application Data

(63) Continuation of application No. 13/392,661, filed as application No. PCT/US2010/040663 on Jun. 30, 2010, now abandoned.
(Continued)

(51) Int. Cl.
*C12N 5/071* (2010.01)
*A61K 35/407* (2015.01)
(Continued)

(52) U.S. Cl.
CPC .............. *C12N 5/067* (2013.01); *A01N 1/021* (2013.01); *A01N 1/0247* (2013.01); *A61K 35/407* (2013.01); *A61M 1/14* (2013.01)

(58) Field of Classification Search
CPC combination set(s) only.
See application file for complete search history.

(56) References Cited

U.S. PATENT DOCUMENTS

| 1,682,344 A | 8/1928 | Lesieur |
| 1,916,658 A | 7/1933 | Davidson |

(Continued)

FOREIGN PATENT DOCUMENTS

| EP | 1246903 | 10/2002 |
| KR | 10-2001-0002227 A | 1/2001 |

(Continued)

OTHER PUBLICATIONS

Nelson et al., Journal of Gastroenterology & Hepatology, 12 (8): 923-930.*
(Continued)

*Primary Examiner* — Allison M Fox
*Assistant Examiner* — Qing Xu
(74) *Attorney, Agent, or Firm* — Fish & Richardson P.C.

(57) ABSTRACT

One aspect of the invention provides a method for harvesting adult cells from an organ. The method includes perfusing the organ with a perfusate and isolating adult cells from the organ, thereby harvesting the adult cells from the organ. Another aspect of the invention provides a method for rehabilitating an organ. The method includes: dividing the organ into a first portion and a second portion, perfusing the
(Continued)

first portion with a decellularization medium, isolating adult cells from the second portion, and recellularizing the first portion with a suspension of the adult cells, thereby rehabilitating the organ.

23 Claims, 34 Drawing Sheets

Related U.S. Application Data

(60) Provisional application No. 61/330,959, filed on May 4, 2010, provisional application No. 61/304,860, filed on Feb. 16, 2010, provisional application No. 61/222,266, filed on Jul. 1, 2009.

(51) Int. Cl.
*A01N 1/02* (2006.01)
*A61M 1/14* (2006.01)

(56) References Cited

U.S. PATENT DOCUMENTS

| | | | |
|---|---|---|---|
| 3,183,961 A | 5/1965 | Herbert | |
| 3,406,531 A | 10/1968 | Swenson et al. | |
| 3,468,136 A | 9/1969 | Swenson et al. | |
| 3,545,221 A | 12/1970 | Swenson et al. | |
| 3,607,646 A | 9/1971 | Roissart | |
| 3,660,241 A | 5/1972 | Michielsen | |
| 3,738,914 A | 6/1973 | Knudson et al. | |
| 3,772,153 A | 11/1973 | De Roissart | |
| 3,810,367 A | 5/1974 | Peterson | |
| 3,843,455 A | 10/1974 | Bier | |
| 3,877,843 A | 4/1975 | Fischel | |
| 3,881,990 A | 5/1975 | Burton et al. | |
| 3,914,954 A | 10/1975 | Doerig | |
| 3,995,444 A | 12/1976 | Clark et al. | |
| 4,186,565 A | 2/1980 | Toledo-Pereyra | |
| 4,242,883 A | 1/1981 | Toledo-Pereyra | |
| 4,745,759 A | 5/1988 | Bauer et al. | |
| 4,798,824 A | 1/1989 | Folkert et al. | |
| 5,356,771 A | 10/1994 | O'Dell | |
| 5,602,026 A | 2/1997 | Dunn et al. | |
| 5,942,436 A | 8/1999 | Dunn et al. | |
| 6,046,046 A | 4/2000 | Hassanein | |
| 6,524,785 B1 | 2/2003 | Cozzone et al. | |
| 6,642,045 B1* | 11/2003 | Brasile | A01N 1/02 435/1.2 |
| 7,371,400 B2 | 5/2008 | Borenstein et al. | |
| 7,410,474 B1 | 8/2008 | Friend et al. | |
| 7,504,201 B2 | 3/2009 | Taylor et al. | |
| 7,572,622 B2 | 8/2009 | Hassanein et al. | |
| 7,651,835 B2 | 1/2010 | Hassanein et al. | |
| 7,691,622 B2 | 4/2010 | Garland et al. | |
| 7,749,693 B2 | 7/2010 | Brassil et al. | |
| 7,811,808 B2 | 10/2010 | Plaats et al. | |
| 7,824,848 B2 | 11/2010 | Owen et al. | |
| 8,268,612 B2 | 9/2012 | Owen et al. | |
| 8,287,580 B2 | 10/2012 | Rakhorst et al. | |
| 8,323,954 B2 | 12/2012 | Kravitz et al. | |
| 8,440,390 B2 | 5/2013 | Brockbank | |
| 8,765,364 B2 | 7/2014 | Curtis et al. | |
| 8,771,930 B2 | 7/2014 | Curtis et al. | |
| 8,927,257 B2 | 1/2015 | Hutzenlaub et al. | |
| 8,986,978 B2 | 3/2015 | Brassil | |
| 9,078,428 B2 | 7/2015 | Hassanein et al. | |
| 9,215,867 B2 | 12/2015 | Hassanein et al. | |
| 9,247,728 B2 | 2/2016 | Fishman et al. | |
| 2002/0039786 A1* | 4/2002 | Reid | C12N 5/0672 435/325 |
| 2004/0058432 A1 | 3/2004 | Owen et al. | |
| 2005/0147958 A1 | 7/2005 | Hassanein et al. | |
| 2005/0221269 A1* | 10/2005 | Taylor | A01N 1/02 435/1.1 |
| 2006/0019326 A1 | 1/2006 | Vacanti et al. | |
| 2007/0009881 A1 | 1/2007 | Arzt et al. | |
| 2007/0042339 A1 | 2/2007 | Toner et al. | |
| 2007/0148139 A1 | 6/2007 | Vacanti et al. | |
| 2008/0096184 A1 | 4/2008 | Brasile | |
| 2008/0234768 A1 | 9/2008 | Hassanein et al. | |
| 2008/0288399 A1 | 11/2008 | Curtis et al. | |
| 2009/0123437 A1 | 5/2009 | Takebe | |
| 2011/0183310 A1 | 7/2011 | Kravitz et al. | |

FOREIGN PATENT DOCUMENTS

| | | |
|---|---|---|
| WO | 20071025233 | 3/2007 |
| WO | 20081024195 | 2/2008 |

OTHER PUBLICATIONS

Donato et al., Drug Metabolism and Disposition, 33(1):108-114 (2005). "Liver grafts preserved in celsior solution as source of hepatocytes for drug metabolism studies: comparison with surgical liver biopsies."
Hughes et al., Liver Transplantation, 12:713-717 (2006). "Isolation of hepatocytes from livers from non-heart-beating donors for cell transplantation."
Nelson, et al., http://cat.inist.fr/?aModele=afficheN&cpsidt=1451795; accessed Aug. 21, 2008. "An improved ex vivo method of primary porcine hepatocyte isolation for use in bioartificial liver systems."
Taylor et al., Transplantation Proceedings, 40:480-482 (2008). "Twenty-four hour hypothermic machine perfusion preservation of porcine pancreas facilitates processing for islet isolation."
Tolboom et al., Tissue Engineering, 13(8):2143-2151 (2007). "A model for normothermic preservation of the rat liver."
Bessems et al., "Improved Machine Perfusion Preservation of the Non-Heart-Beating Donor Rat Liver Using Polysol: A New Machine Perfusion Preservation Solution", Liver Transplantation 11(11):1379-1388 (2005).
Bessems et al., "Machine Perfusion Preservation of the Pig Liver Using a New Preservation Solution, Polysol", Transplant Proceedings 38(5):1238-1242 (2006).
Brockmann et al., "Normothermic Perfusion: A New Paradigm for Organ Preservation", Annals of Surgery 250(1):1-6 (2009).
Buis et al., "Altered bile composition after liver transplantation is associated with the development of nonanastomotic biliary strictures", Journal of Hepatology 50(1):69-79 (2009).
Butler et al., "Successful Extracorporeal Porcine Liver Perfusion for 72 Hr", Transplantation 73(8):1212-1218 (2002).
Chen et al., "Effective Application of ET-Kyoto Solution for Clinical Lung Transplantation", Transplantation Proceedings 36(9):2812-2815 (2004).
Cypel et al., "Normothermic Ex Vivo Perfusion Prevents Lung Injury Compared to Extended Cold Preservation for Transplantation", American Journal of Transplantation 9:2262-2269 (2009).
De Rougemont et al., "One Hour Hypothermic Oxygenated Perfusion (HOPE) Protects Nonviable Liver Allografts Donated After Cardiac Death", Ann Surg. 250(5):674-683 (2009).
De Vera et al., "Liver Transplantation Using Donation After Cardiac Death Donors: Long-Term Follow-Up From a Single Center", American Journal of Transplantation 9:773-781 (2009).
Fahy et al., "Cryopreservation of Complex Systems: The Missing Link in the Regenerative Medicine Supply Chain", Rejuvenation Research 9(2):279-291 (2006).
Friend et al., "Normothermic Perfusion of the Isolated Liver", Transplantation Proceedings 33:3436-3438 (2001).
Geuken et al., "Rapid increase of bile salt secretion is associated with bile duct injury after human liver transplantation", Journal of Hepatology 41:1017-1025 (2004).
Giknis et al., "Clinical Laboratory Parameters for Crl:CD(SD) Rats", Charles River Laboratories 1-18 (2006). Online: http://www.criver.com/sitecollectiondocuments/rm_rm_r_clinicalparameters_cd_rat_06.

(56) References Cited

OTHER PUBLICATIONS

Hertl et al., "Evidence of Preservation Injury to Bile Ducts by Bile Salts in the Pig and its Prevention by Infusions of Hydrophilic Bile Salts", Hepatology 21(4):1130-1137 (1995).
Hoekstra et al., "Bile Salt Toxicity Aggravates Cold Ischemic Injury of Bile Ducts After Liver Transplantation in Mdr2+/− Mice", Hepatolgy 43(5):1022-1031 (2006).
Imber et al., "Optimisation of Bile Production during Normothermic Preservation of Porcine Livers", American Journal of Transplantation 2:593-599 (2002).
Jain et al., "Long-Term Survival After Liver Transplantation in 4,000 Consecutive Patients at a Single Center", Annals of Surgery 232(4):490-500 (2000).
Kamiike et al., "Adenine Nucleotide Metabolism and its Relation to Organ Viability in Human Liver Transplantation", Transplantation 45(1):138-143 (1988).
Lanir et al., "Hepatic Transplantation Survival: Correlation with Adenine Nucleotide Level in Donor Liver", Hepatology 8(3):471-475 (1988).
Lee et al. "Metabolic Flux Analysis of Postburn Hepatic Hypermetabolism", Metabolic Engineering 2(4):312-327 (2000).
Mccord, "Oxygen-Derived Free Radicals in Postischemic Tissue Injury", N Engl J Med. 312(3):159-163 (1985).
Mccormack et al., "Use of Severely Steatotic Grafts in Liver Transplantation: A Matched Case-Control Study", Ann Surg. 246(6):940-948 (2007).
Minor et al., "Fibrinolysis in organ procurement for transplantation after cardiocirculatory compromise", Thromb Haemost 90(2):361-362 (2003).
Mitchell et al., "Energy Metabolism Following Prolonged Hepatic Cold Preservation: Benefits of Interrupted Hypoxia on the Adenine Nucleotide Pool in Rat Liver", Cryobiology 39:130-137 (1999).
Miyagi et al., "The Significance of Preserving the Energy Status and Microcirculation in Liver Grafts from Non-Heart-Beating Donor", Cell Transplantation 17(1-2):173-178 (2008).
Moore et al., "Impact of Donor, Technical, and Recipient Risk Factors on Survival and Quality of Life After Liver Transplantation", Arch Surg. 140(3):273-277 (2005).
Okamoto et al., "Successful Sub-Zero Non-freezing Preservation of Rat Lungs at −2C Utilizing a New Supercooling Technology", Journal of Heart and Lung Transplant 27(10):1150-1157 (2008).
Peter et al., "Hepatic Control of Perfusate Homeostasis During Normothermic Extrocorporeal Preservation", Transplantation Proceedings 35(4):1587-1590 (2003).
Reddy et al., "Non-Heart-Beating Donor Porcine Livers: the Adverse Effect of Cooling", Liver Transplantation 11(1):35-38 (2005).
Reddy et al., "Preservation of Porcine Non-Heart-Beating Donor Livers by Sequential Cold Storage and Warm Perfusion", Transplantation 77(9):1328-1332 (2004).
Sakaguchi et al., "Preservation of Myocardial Function and Metabolism at Subzero Nonfreezing Temperature Storage of the Heart", J Heart Lung Transplant 15(11):1101-1107 (1996).
Serracino-Inglott et al., "Hepatic ischemia-reperfusion injury", The American Journal of Surgery 181(12:160-166 (2001).
Soltys et al., "Successful Nonfreezing, Subzero, Preservation of Rat Liver with 2,3-Butanediol and Type I Antifreeze Protein", Journal of Surgical Research 96(1):30-34 (2001).
St Peter et al., "Extended preservation of non-heart-beating donor livers with normothermic machine perfusion", British Journal of Surgery 89:609-616 (2002).
Tolboom et al., "Recovery of Warm Ischemic Rat Liver Grafts by Normothermic Extracorporeal Perfusion", Transplantation 87(2):170-177 (2009).

Tolboom et al., "Sequential Cold Storage and Normothermic Perfusion of the Ischemic Rat Liver", Tranplantation Proceedings 40(5):1306-1309 (2008).
Vairetti et al., "Correlation Between the Liver Temperature Employed During Machine Perfusion and Reperfusion Damage: Role of Ca2+", Liver Transplantation 14:494-503 (2008).
Vajdova et al., "ATP-Supplies in the Cold-Preserved Liver: A Long-Neglected Factor of Organ Viability", Hepatology 36(6):1543-1552 (2002).
Vajdova et al., "Cold-Preservation-Induced Sensitivity of Rat Hepatocyte Function to Rewarming Injury and its Prevention by Short-Term Reperfusion", Hepatology 32(2):289-296 (2000).
Van Der Plaats et al., "The Groningen Hypothermic Liver Perfusion Pump: Functional Evaluation of a New Machine Perfusion System", Annals of Biomedical Engineering 34(12):1924-1934 (2006).
Vollmar et al., "In vivo quantification of ageing changes in the rat liver from early juvenile to senescent life", Liver 22(4):330-341 (2002).
Wojcicki et al., "Biliary Tract Complications after Liver Transplantation: A Review", Dig Surg. 25:245-257 (2008).
Zhao K et al., "Cell-permeable Peptide Antioxidants Targeted to Inner Mitochondrial Membrane Inhibit Mitochondria Swelling, Oxidative Cell Death, and Reperfusion Injury", The Journal of Biological Chemistry 279(33):34682-34690 (2004).
Sugimachi et al., "Nonmetabolizable glucose compounds impart cryotolerance to primary rat hepatocytes", Tissue Eng 12(3):579-588 (2006).
Amersi et al, "Bucillamine, a thiol antioxidant, prevents transplantation-associate reperfusion injury," Proc. Nat'l Acacl. Sci., Jun. 2002, 99(13):8915-8920.
Dunn et aL, "Long-Term in Vitro Function of Adult Hepatocytes in a Collagen Sandwich Configuration," Biotechnology Progress, May 1991, 7(3):237-45.
Gui et al., "Novel utilization of serum in tissue decellularization," Tissue Engineering, Apr. 2010, 16(2):173-184.
Hoffenberg, "Measurement of the synthesis of liver-produced plasma proteins with particular reference to dietary protein and amino acid supply," The Biochemical Journal, Sep. 1972, 129(2):3P-3P.
Khetani & Bhatia, "Microscale culture of human liver cells for drug development," Nature Biochemistry Jan. 2008, 26(1):120-126.
Liu et al., "Operative Outcomes of Adult-to-Adult Right Lobe Live Donor Liver Transplantation: A Comparative Study With Cadaveric Whole-Graft Liver Transplantation in a Single Center," Annals of Surgery, Mar. 2006, 243(3):404-410.
PCT International Preliminary Report on Patentability in International Appln. No. PCT/US2010/040663, dated Jan. 4, 2012, 7 pages.
PCT International Search Report and Written Opinion in International Appln. No. PCT/US2010/040663, dated Mar. 17, 2011, 11 pages.
Rodriguez et al., "Subzero nonfreezing storage of rat hepatocytes using modified University of Wisconsin solution (mUW) and 1, 4-butanediol. I-effects on cellular metabolites during cold storage," Annals of Hepatology, 2009, 8(1):57-62.
Shah et al, "Adult-to-adult living donor liver transplantation," Can. J. Gastroenterol., 2006, 20(5):339-343.
Terry et al, "Cryopreservation of isolated human hepatocytes for transplantation. State of the art," Cryobiology, Oct. 2006, 53(2):149-159.
Tolbloom et al., "Recovery of warm ischemic rat liver grafts by normothermic extracorporeal perfusion," Transplantation, Jan. 2009, 87(2):170-77.

* cited by examiner

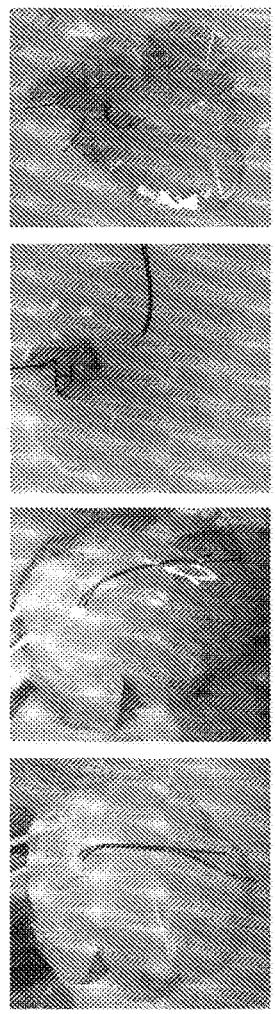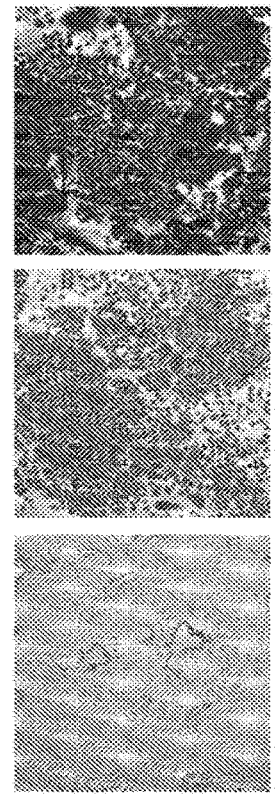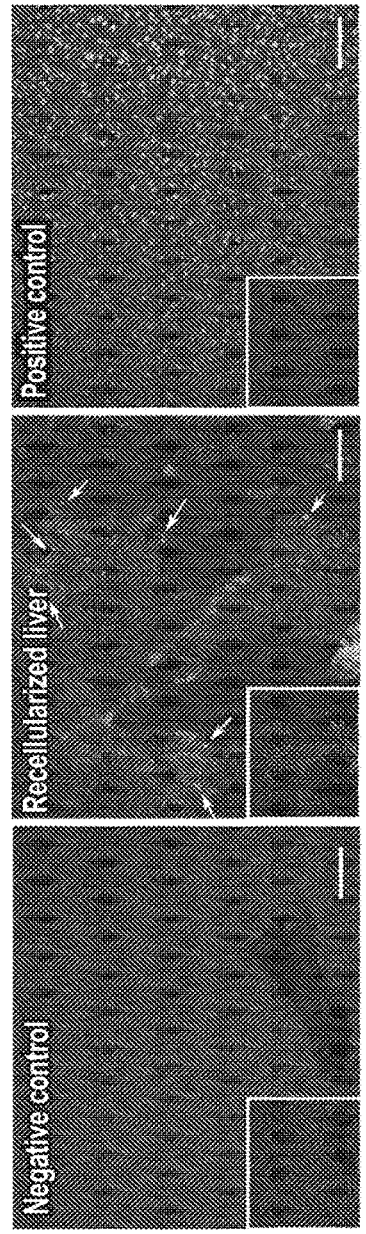
FIG. 14A  FIG. 14B  FIG. 14C  FIG. 14D
FIG. 15A  FIG. 15B  FIG. 15C
FIG. 16A  FIG. 16B  FIG. 16C

ISOLATED ADULT CELLS, ARTIFICIAL ORGANS, REHABILITATED ORGANS, RESEARCH TOOLS, ORGAN ENCASEMENTS, ORGAN PERFUSION SYSTEMS, AND METHODS FOR PREPARING AND UTILIZING THE SAME

RELATED APPLICATIONS

This application is a Continuation of U.S. patent application Ser. No. 13/392,661 filed Mar. 13, 2013, which is a 35 U.S.C. § 371 National Phase Entry Application of International Application No. PCT/US2010/040663 filed Jun. 30, 2010, which claims benefit under 35 U.S.C. § 119(e) of U.S. Provisional Patent Application Ser. No. 61/222,266, filed Jul. 1, 2009; U.S. Provisional Patent Application Ser. No. 61/304,860 filed Feb. 16, 2010; and U.S. Provisional Patent Application Ser. No. 61/330,959, filed May 4, 2010. The entire contents of each application are incorporated herein by reference.

STATEMENT AS TO RIGHTS TO INVENTIONS MADE UNDER FEDERAL SPONSORED RESEARCH AND DEVELOPMENT

This invention was made with government support under Grant Nos. DK059766 and DK080942 awarded by the National Institutes of Health and Grant No NSF CBET-0853569 awarded by the National Science Foundation. The U.S. Government has certain rights in this invention.

BACKGROUND

About thirty million people in the United States suffer from liver disorders of varying causes and about 27,000 deaths are registered annually in the United States due to liver disease. At this time, the only definitive treatment of hepatic failure is orthotopic liver transplantation. However, there is a critical shortage of organs with the total organ waiting list currently including about 100,000 requests (for all organs) and increasing at about 5% annually. Given that only organs in pristine condition are transplantable and the hidden demand for organs as an anti-aging solution will be many times the current figures, there will always be a limited pool of organs for orthotopic transplantation.

In addition, human hepatocytes (HHs) are in increasing demand as an ideal model tier absorption, distribution, metabolism, excretion, and toxicology (ADMET) studies in drug development. HHs are ideal for drug development and testing as they enable a realistic estimation of the response of the human liver, whereas animal models are greatly limited because detoxification metabolism varies between species. Further, as liver replacement therapies such as cell transplantation, engineered hepatic tissues, and bioartificial livers approach clinical realization, the demand for human cells is expected to increase drastically.

Cell transplantation is a new and elegant approach that can address the need for organs and can also be used for patients that are severely ill or as a preventative therapy. However, the direct delivery of cells is inefficient due to low engraftment. A tissue-engineered vehicle designed to ensure long-term cell engraftment, viability, and functionality is a necessity to make cell transplantation work clinically. Unfortunately, tissue engineering has so far had limited success in many tissues, including the liver. The key factor that prevents advancement of the field is the lack of an ideal transplantable scaffold that has all the necessary microstructure and extracellular cues for cell attachment, differentiation, functioning, as well as vascularization, which has so far proven to be difficult to manufacture in vitro.

Currently, the availability and quality of human cells and tissues, including hepatocytes (the major cell type in the liver) is very limited. The only reliable source of cells and tissues is human donor livers. Stem-cell-derived hepatocytes are not fully equivalent to primary human hepatocytes (adult hepatocytes) and are time consuming and very expensive to produce in mass quantities. However, organs in good condition are used for transplantation. Therefore, only the worst quality livers are available for hepatocyte isolation. The available livers typically are either excessively fatty or are recovered from donors after cardiac death. In either case, the hepatocytes suffer extended ischemic damage, and the quantity and quality of the cells isolated is greatly reduced compared to ideal livers.

Accordingly, there is a need for new methods and devices for harvesting cells from damaged organs, rehabilitating damaged organs with harvested cells, and providing artificial organs containing harvested cells.

SUMMARY OF THE INVENTION

One aspect of the invention provides a method for harvesting adult cells from an organ. The method includes perfusing the organ with a perfusate and isolating adult cells from the organ, thereby harvesting the adult cells from the organ.

In one embodiment, the organ is a mammalian organ. In another embodiment, the organ is a human organ. In still another embodiment, the organ is a liver. The adult cells can be selected from the group consisting of: hepatocytes, endothelial cells, cholangiocytes (bile duct cells), Kupffer cells, stellate cells, and smooth muscle cells. The organ can be selected from the group consisting of: pancreas, spleen, heart, lung, and kidney. The organ can be ischemic.

In another embodiment, the perfusate includes one or more oxygen carriers. The one or more oxygen carriers can include erythrocytes. The perfusate can include one or more anti-inflammatory agents. The one or anti-inflammatory agents can include hydrocortisone. The perfusate can include collagenase. The perfusate can be normothermic perfusate, a room temperature perfusate, or a hypothermic perfusate.

In another embodiment, the method includes culturing the harvested adult cells. The method can include providing the organ. The step of isolating the adult cells from the organ can include filtering the perfusate. The filtering the perfusate step can include filtering the perfusate through one or more mesh filters. The one or more mesh filters can have pore sizes ranging, from about 1 µm to about 1000 µm. The step of isolating the adult cells from the organ can include performing density centrifugation on the perfusate. The method can include circulating the perfusate through a dialyzer. The organ can be a damaged organ. The perfusion step can improve the vitality of the adult cells.

Another aspect of the invention provides a method for rehabilitating an organ. The method includes: dividing the organ into a first portion and a second portion, perfusing the first portion with a decellularization medium, isolating adult cells from the second portion, and recellularizing the first portion with a suspension of the adult cells, thereby rehabilitating the organ.

In one embodiment, the method includes preserving the first portion. The preserving step can include washing the first portion with one or more isotonic washes. The preserving step can include storing the first portion in a storage medium. The storage medium can include one or more antimicrobial agents. The one or more antimicrobial agents can be selected from the group consisting of antibiotics and fungicides.

In another embodiment, the method includes culturing the adult cells. The method can include perfusing the recellularized first portion. The method can include transplanting the first portion into a subject. The organ can be previously harvested from the subject. The organ can be a damaged organ. The method can include utilizing the first portion as an in vitro model. The in vitro model can be an in vitro model of organ function. The method can include the first portion as an in vitro drug model. The in vitro drug model can be an in vitro model of drug absorption, drug metabolism, drug excretion, and/or drug toxicity. The first portion and the second portion can be substantially equal in size.

In another embodiment, the decellularization medium includes one or more agents selected from the group consisting of detergents, vasodilators, buffers, inorganic salts, and enzymes.

In another embodiment, the organ is mammalian and/or human. The organ can be selected from the group consisting of liver, pancreas, kidney, spleen, heart, and lung.

Another aspect of the invention provides a rehabilitated organ prepared by a method including: dividing an organ into a first portion and a second portion, perfusing the first portion with a decellularization medium, isolating adult cells from the second portion, and recellularizing the first portion with a suspension of the adult cells, thereby preparing a rehabilitated organ.

In one embodiment, the method includes preserving the first portion. The method can include washing the first portion with one or more isotonic washes. The method can include storing the first portion in a storage medium. The storage medium can include one or more antimicrobial agents. The one or more antimicrobial agents can be selected from the group consisting of antibiotics and fungicides.

The organ can be a damaged organ. The first portion and the second portion can be substantially equal in size. The decellularization medium can include one or more agents selected from the group consisting of detergents, vasodilators, buffers, inorganic salts, and enzymes. The organ can be mammalian and/or human. The organ can be selected from the group consisting of liver, pancreas, kidney, spleen, heart, and lung.

Another aspect of the invention provides an artificial organ including: a bioscaffold comprising an extracellular matrix having a vascular network and a plurality of adult cells. The adult cells are engrafted to the matrix and are vascularized such that the adult cells are capable of organ function.

In one embodiment, the plurality of adult cells were previously harvested from one or more other organs. The bioscaffold can be derived from a previously decellularized organ. The bioscaffold can be bioartificial organ device. The bioscaffold and the adult cells can be mammalian-derived. The bioscaffold and the adult cells can be human-derived. The bioscaffold and the adult cells can be derived from an organ selected from the group consisting of: liver, pancreas, kidney, spleen, heart, and lung. The bioscaffold and the adult cells can be derived from a liver. The adult cells are harvested from an organ by any method described herein.

In another embodiment, the bioscaffold is prepared according to a method including: cannulating one or more vessels of an organ and decellularizing the organ, thereby preparing a bioscaffold comprising a decellularized extracellular matrix having a vascular network. The decellularizing step can include perfusing the organ with a decellularization medium. The decellularization medium can include one or more agents selected from the group consisting of detergents, vasodilators, buffers, inorganic salts, and enzymes. The perfusion can be single or multidirectional perfusion. The perfusion is can be machine- or gravity-driven perfusion. The temperature of the decellularization medium can be maintained between about 4° C. and about 42° C. The organ can be perfused from about 4 hours to about 14 days. The organ can be perfused for between about 4 days and about 7 days.

In another embodiment, the method includes preserving the bioscaffold. The preserving step can include washing the bioscaffold with one or more isotonic washes. The preserving step can include storing the bioscaffold in a storage medium. The storage medium can include one or more antimicrobial agents. The one or more antimicrobial agents can be selected from the group consisting of antibiotics and fungicides. The bioscaffold can be stored at a temperature less than about 4° C.

In another embodiment, the organ is mammalian and/or human. The organ can be selected from the group consisting of liver, pancreas, kidney, spleen, heart, and lung. The organ can be a liver.

Another aspect of the invention provides a method for fabricating an artificial organ. The method includes: cannulating one or more vessels in a bioscaffold and cellularizing the bioscaffold by introducing a suspension of adult organ cells into the bioscaffold, thereby preparing an artificial organ.

In one embodiment, the method includes perfusing the cellularized bioscaffold. The perfusion can be machine- or gravity-driven perfusion. The suspension can include a solution of osmolality ranging from about 100 mOsm to about 500 mOsm, one or more oxygen carriers, one or more antioxidants, one or more anti-inflammatory agents, one or more vasodilators, one or more amino acids, one or more buffers, one or more inorganic salts, one or more substrates for metabolism, and one or more agents to maintain oncotic pressure between about 15 to about 45 mm Hg.

In one embodiment, the suspension of adult organ cells is introduced into the bioscaffold by injection or perfusion.

In another embodiment, the method includes preserving the artificial organ. The preserving step can include washing the artificial organ with one or more isotonic washes. The preserving step can include storing the artificial organ in a storage medium. The storage medium can include one or more antimicrobial agents. The one or more antimicrobial agents can be selected from the group consisting of antibiotics and fungicides. The artificial organ can be stored at a temperature less than about 4° C.

In another embodiment, the bioscaffold and the adult cells are mammalian-derived and/or human-derived. The bioscaffold and the adult cells can be derived from an organ selected from the group consisting of liver, pancreas, kidney, spleen, heart, and lung. The bioscaffold and the adult cells can be derived from a liver. The adult cells can be harvested from an organ by any method described herein.

In another embodiment, the method includes preparing the bioscaffold according to a method including: cannulating one or more vessels of an organ and decellularizing the organ, thereby preparing a bioscaffold comprising a decellularized extracellular matrix having a vascular network. Decellularizing the organ can include perfusing the organ with a decellularization medium. The decellularization medium can include one or more agents selected from the group consisting of detergents, vasodilators, buffers, inorganic salts, and enzymes. The perfusion can be single or multidirectional perfusion. The perfusion can be machine- or gravity-driven perfusion. The temperature of the decellurization medium can be maintained between about 4° C. and about 42° C. The organ can be perfused from about 4 hours to about 14 days. The organ can be perfused for between about 4 days and about 7 days.

In another embodiment, the method includes preserving the bioscaffold. The preserving step can include washing the bioscaffold with one or more isotonic washes. The preserving step can include storing the bioscaffold in a storage medium. The storage medium can include one or more antimicrobial agents. The one or more antimicrobial agents can be selected from the group consisting of antibiotics and fungicides. The bioscaffold can be stored at a temperature less than about 4° C.

In another embodiment, the organ is mammalian and/or human. The organ can be selected from the group consisting of liver, pancreas, kidney, spleen, heart, and lung. The organ can be a liver.

Another aspect of the invention provides an organ encasement including: a first membrane and a second membrane adapted for coupling with the first membrane to encase an organ.

In one embodiment, the organ encasement also includes coupling means for coupling the first and the second membrane. The coupling means can be selected from the group consisting of: magnets, screws, bolts, nuts, rivets, adhesives, and zipper storage assemblies.

In another embodiment, the first membrane and the second membrane are flexible. The first membrane and the second membrane can be gas permeable. The first membrane and the second membrane can be biocompatible. The first membrane and the second membrane can include one or more biocompatible materials selected from the group consisting of: silicone, thermoset polymers, thermoplastic polymers, amniotic membranes, small intestinal submucosa (SIS), fascia, dura mater, peritoneum, and pericardium.

Another aspect of the invention provides an organ perfusion system including: an organ encasement and a primary circuit in fluid communication with an organ encasement for circulating a perfusate.

In one embodiment, the primary circuit includes a pressure sensor. In other embodiments, the primary circuit can include a sampling port, a heat exchanger, a bubble trap, an oxygenator, and/or one or more pumps. The primary circuit can include a first cannula in communication with the organ and a second cannula in communication with the organ.

In another embodiment, the organ perfusion system includes: dialyzer in communication with the primary circuit and a secondary circuit in communication with the dialyzer. The secondary circuit can include: a pump and a dialysate reservoir.

In another embodiment, the primary circuit includes one or more decellularization modules and/or one or more recellularization modules. The organ perfusion system can be adapted to preserve the organ.

Another aspect of the invention provides a method of perfusing an organ. The method includes: providing an organ perfusion system including an organ encasement and a primary circuit in fluid communication with an organ encasement for circulating perfusate; placing an organ within the organ encasement; and circulating the perfusate.

In one embodiment, the perfusate is a normothermic perfusate. The perfusate can be a room temperature perfusate. The perfusate can be a hypothermic perfusate.

Another aspect of the invention provides a kit for perfusing an organ. The kit includes: an organ encasement, a perfusate, and instructions for use.

Another aspect of the invention provides a kit for preparing a recellularized bioscaffold. The kit includes: a plurality of adult cells, a perfusate, and instructions for use.

In one embodiment, the kit includes a bioscaffold encasement.

Another aspect of the invention provides an artificial organ production system including: an organ encasement and a primary circuit in fluid communication with an organ encasement for circulating a perfusate. The primary circuit includes: one or more decellularization modules and one or more recellularization modules.

Another aspect of the invention provides a method for producing, a research tool. The method includes: slicing a decellularized organ to produce a decellularized organ slice, plating the decellularized organ slice, seeding the decellularized organ slice with one or more cells to produce a recellularized organ slice, and culturing the recellularized organ slice.

In one embodiment, the method includes storing the recellularized organ slice. The method can include using the recellularized organ slice in an experiment. The one or more cells can be adult cells and/or stem cells.

Another aspect of the invention provides a research tool prepared by a method including: slicing a decellularized organ to produce a decellularized organ slice, plating the decellularized organ slice, seeding the decellularized organ slice with one or more cells to produce a recellularized organ slice, and culturing the recellularized organ slice.

Another aspect of the invention provides a method for producing a research tool. The includes: slicing an organ to produce an organ slice; decellularizing the organ slice to produce a decellularized organ slice; seeding the decellularized organ slice with one or more cells to produce a recellularized organ slice; and culturing the recellularized organ slice.

In one embodiment, the method includes storing the recellularized organ slice. The method can include using the recellularized organ slice in an experiment. The one or more cells can be adult cells. The one or more cells can be stem cells. The method can include plating the decellularized organ slice.

Another aspect of the invention provides a research tool prepared by a method including: slicing an organ to produce an organ slice; decellularizing the organ slice to produce a decellularized organ slice; seeding the decellularized organ slice with one or more cells to produce a recellularized organ slice; and culturing the recellularized organ slice.

Another aspect of the invention provides a method for producing a research tool. The method includes: slicing a recellularized organ to produce a recellularized organ slice and plating the recellularized organ slice.

In one embodiment, the method includes storing the recellularized organ slice. The method can include using the recellularized organ slice in an experiment.

Another aspect of the invention provides a research tool prepared by a method including: slicing a recellularized organ to produce a recellularized organ slice and plating the recellularized organ slice.

In one embodiment, the research tool includes a recellularized organ slice. The research tool can also include a vessel. The recellularized organ slice can be received within the vessel. The vessel can contain an agar and wherein the recellularized organ slice is mounted on the agar. The recellularized organ slice can be seeded with cells before slicing. The recellularized organ slice can be seeded with cells after slicing.

Another aspect of the invention provides an assay method including: applying one or more test agents to a recellularized organ slice, incubating the recellularized organ slice, and analyzing one or more metabolites of the test agent.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views and wherein:

FIGS. 14A-14D are representative photographs of liver during infusion with isolated rat hepatocytes.

FIGS. 15A-15C are representative photographs of H&E-stained recellularized livers.

FIGS. 16A-16C are representative photographs of TUNEL-stained recellularized livers after eight hours of perfusion. FIG. 16A depicts a negative control of TUNEL staining without antibodies. FIG. 16b depicts the staining of apoptic cells in green. FIG. 16C depicts TUNEL staining of a DNAse exposed liver sample as a positive control. DAPI staining of nuclei is presented in the bottom left inset of each figure.

FIGS. 18A and 18D depict normal livers. FIGS. 18B and 18E depict recellularized livers 24 hours after recellularization. FIGS. 18C and 18F depict recellularized livers 48 hours after recellularization.

FIG. 22A depicts the decellularized liver matrix before perfusion with Allura Red AC dye and FIG. 22B depicts the decellularized liver matrix after perfusion with Allura Red AC dye.

FIG. 24A is an SEM image of a blood vessel. FIG. 24B is a section featuring bile-duct-like small vessels identified with white arrows. FIG. 24C displays the extracellular matrix within the parenchyma with hepatocyte-size free spaces. The scale bar in each of FIGS. 24A-C represents 20 µm.

DETAILED DESCRIPTION

Figure 1:
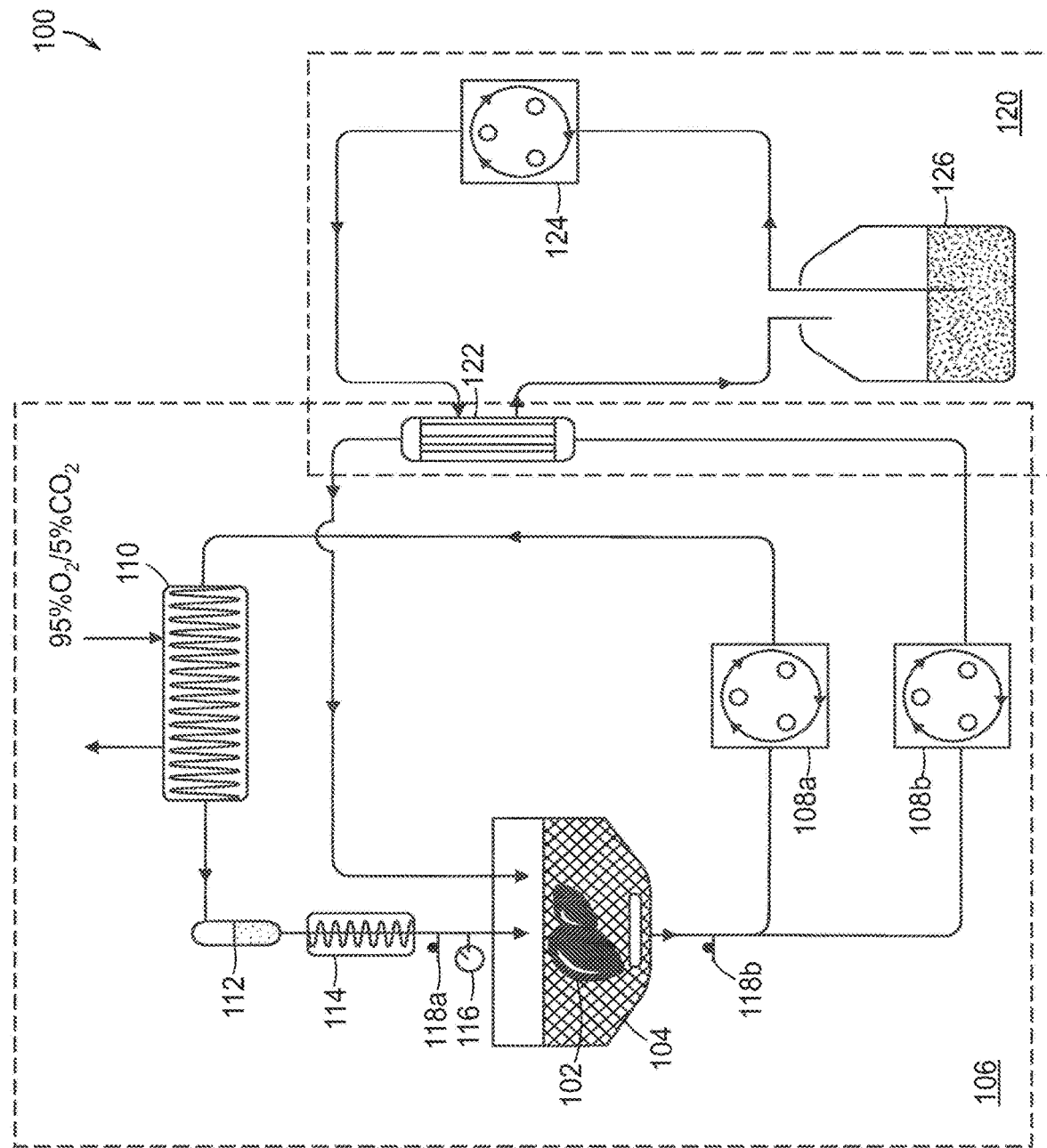
FIG. 1 depicts a perfusion system according to an embodiment of the invention.

The instant invention is most clearly understood with reference to the following definitions:

As used in the specification and claims, the singular form "a," "an," and "the" include plural references unless the context clearly dictates otherwise.

An "adult cell" shall be understood to mean any cell capable of perforating essential organ functions. The term "adult cell," as used in the specification and shall be distinguished from the term "stem cell."

The term "biocompatible" shall be understood to refer to any material that is nontoxic and, optionally, does not provoke an immunological rejection. Biocompatible materials can be naturally occurring or synthetic and permit diffusion of liquids, gases, and/or ions. Biocompatible materials in accordance with the invention include, for example, membranous materials selected from the group consisting of silicone, thermoset polymers, thermoplastic polymers, amniotic membranes, small intestinal submucosa (SIS), fascia, dura mater, peritoneum, and pericardium.

A "bioscaffold" shall be understood to include any structure that provides an extracellular matrix sufficient to support one or more cells.

A "damaged organ" shall be understood to indicate an organ that is in less than ideal condition far transplantation, such that the expected probability of transplant success is reduced. Examples of damaged organs include, but are not limited to, organs that suffer warm ischemia for more than 30 minutes, organs that suffer cold ischemia for more than 12 hours, moderate or highly steatotic livers (e.g., livers with greater than 30% fat), fibrotic livers, cirrhotic livers, livers from patients afflicted with hepatitis C or HIV, and the like.

The term "decellularize" shall be understood to mean any process for the removing one or more cells from an organ. Preferably, a decellularization process maintains the extracellular matrix and vascular structure of the organ.

"Essential hepatic function" shall be understood to include one or more of the following: protein synthesis; protein storage; transformation of carbohydrates; synthesis of cholesterol, bile salts, and/or phospholipids; and detoxification, modification, and/or excretion of exogenous and endogenous substances.

An "extracellular matrix" shall be understood to be the portion of an organ and/or a bioscaffold that provides structural and life support for one or more cells.

A "health care provider" shall be understood to mean any person providing medical care to a patient. Such persons include, but are not limited to, medical doctors, physician's assistants, nurse practitioners (e.g., an Advanced Registered Nurse Practitioner (ARNP)), nurses, residents, interns, medical students, or the like. Although various licensure requirements may apply to one or more of the occupations listed above in various jurisdictions, the term health care provider is unencumbered for the purposes of this patent application.

"Hypothermic" shall be understood to mean temperatures below room temperature. For example, "hypothermic" temperatures include, but are not limited to, temperatures between about 0° C. to about 15° C., temperatures between about 1° C. to about 8° C., temperatures between about 3° C. to about 5° C., and the like.

An "in vitro model" shall be understood to be a model created outside of an organism of a subset of the organism's constituent parts, for example, for studying the function of the constituent parts. An "in vitro drug model" shall be understood to be an in vitro model created to study the interaction of a drug, pharmaceutical, test agent, and the like with a subset of an organism's constituent parts. Interactions can include absorption, distribution, metabolism, toxicity, and the like.

"Normothermic" shall be understood to mean temperatures above room temperature. For example, "normothermic" temperatures include, but are not limited to, temperatures between about 25° C. and about 42° C., temperatures between about 30° C. and about 38° C., temperatures between about 37° C. and about 37.5° C., and the like.

An "organ" is a tissue that performs a specific function or group of functions within an organism. The term organ includes the heart, lungs, stomach, liver, gallbladder, pancreas, spleen, kidneys, and the like.

A "perfusate" shall be understood to be any fluid capable of improving or maintaining the vitality of a cell, tissue, organ (including decellularized and recellularized organs), bioscaffold, and the like. Improving or maintaining vitality can include one or more of the following: maintenance of appropriate osmotic pressure, maintenance of appropriate oncotic pressure, maintenance of appropriate temperature, inhibition of decay, inhibition of microbial growth, and the like.

The term "recellularize" shall be understood to be any process for engrafting one or more cells within a decellularized organ or bioscaffold.

"Room temperature" shall be understood to mean a temperature between about 15° C. and about 25° C. For example, "room temperature" includes, but is not limited to, temperatures between about 18° C. and about 23° C., temperature between about 19° C. and about 21° C., temperatures between about 24° C. and about 25° C., temperatures between about 20° C. and about 21° C. and the like.

A "storage medium" shall be understood to be any substance for preserving vitality of a cell, tissue, organ (including decellularized and recellularized organs), bioscaffold, and the like. Preservation of vitality can include one or more of the following: maintenance of appropriate osmotic pressure, maintenance of appropriate oncotic pressure, maintenance of appropriate temperature, inhibition of decay, inhibition of microbial growth, and the like.

A "subject" shall be understood to include any mammal including, but not limited to, humans, primates, swine, cows, sheep, and rats.

A "test agent" shall be understood to include any substance that is evaluated for its ability to diagnose, cure, mitigate, treat, or prevent disease in a subject, or is intended to alter the structure or function of the body of a subject. A test agent in an embodiment can be a "drug" as that term is defined under the Federal Food, Drug, and Cosmetic Act at 21 U.S.C. § 321(g)(1). Test agents include, but are not limited to, chemical compounds, biologic agents, proteins, peptides, nucleic acids, lipids, polysaccharides, supplements, diagnostic agents and immune modulators.

A "vascular network" shall be understood to be the portion of an organ that provides fluid (e.g., blood) access to one or more cells. The vascular network can form part of the extracellular matrix and is capable of handling the pressure and viscosity of physiological fluids.

Aspects of the invention provide new methods and devices for harvesting cells from and rehabilitating damaged organs.

Organ Perfusion Systems

Referring to FIG. 1, a perfusion system 100 is provided for perfusing an organ prior to cell isolation. An organ 102 (e.g., a liver) is received within a perfusion chamber 104. The perfusion chamber 102 can be any vessel capable of holding an organ and a perfusate. In some embodiments, the perfusion chamber 102 is a vessel such as a glass or plastic bowl. In other embodiments, the perfusion chamber 102 is an organ encasement as described herein.

A primary circuit 106 circulates a perfusate through the organ 102 and perfusion chamber 104. The primary circuit 106 can include one or more pumps 108a, 108b to promote perfusate circulation. Alternatively, the perfusion can be gravity-driven. The primary circuit can also include an oxygenator 110, a bubble trap 112, a heat exchanger 114, a pressure sensor 116, and one or more sampling ports 118a, 118b.

Some embodiments of the perfusion system 100 include a secondary circuit 120 that interfaces with the primary circuit 106 via a dialyzer 122. In some embodiments, the dialyzer is a hollow fiber dialyzer with a 30 kD nominal molecular weight cut-off membrane. The secondary circuit 120 can include a pump 124 for circulating a dialysate 126 through the dialyzer 122.

In some embodiments, a control unit (not depicted) monitors operating parameters (e.g., pressure, flow rate, temperature, oxygen levels, electrolyte levels, and the like) and/or organ function and viability indicators (e.g., production of albumin, urea, nitrogen oxide, and the like) via sample ports 118a, 118b. The control unit can control the operation of pumps 108a, 108b, 124 and heat exchanger 114. The control unit can include a user interface for displaying one or more parameters and indicators and/or allowing a user to alter one or more parameters.

Additionally or alternatively, the control unit can include storage means for storing one or more parameters and indicators and/or communication means for communicating one or more one or more parameters and indicators with another system (e.g., a personal computer, a cellular phone, a personal digital assistant, and the like). In some embodiments, the control unit includes an audible and/or visual alarm to alert users when one or more parameters or indicators exceeds a threshold.

In some embodiments, organ perfusion system 100 is modified to create an artificial organ production system. In such an embodiment, organ perfusion system 100 includes one or more decellularization or recellularization modules (not depicted) to implement the methods described herein. Such modules can include appropriate media as described herein to achieve the decellularization of an organ and/or recellularization of a bioscaffold. For example, organ perfusion system can be configured to perfuse an organ to maintain vitality before actuating the decellularization module to perfuse with a detergent as described herein to decellularize the organ. Finally, the recellularization module can be actuated to recellularize the organ with cells harvested from another source.

Organ Encasements

Conventional organ perfusion systems utilize a rigid vessel such as a glass bowl as a perfusion chamber. Such rigid vessels can be problematic for several reasons. First, the geometry of rigid vessels typically does not compliment the geometry of the organ, which can cause pressure points where the organ contacts the vessel. Second, gravitational forces can deform the organ to fit into corners of the vessel.

Figure 2A:
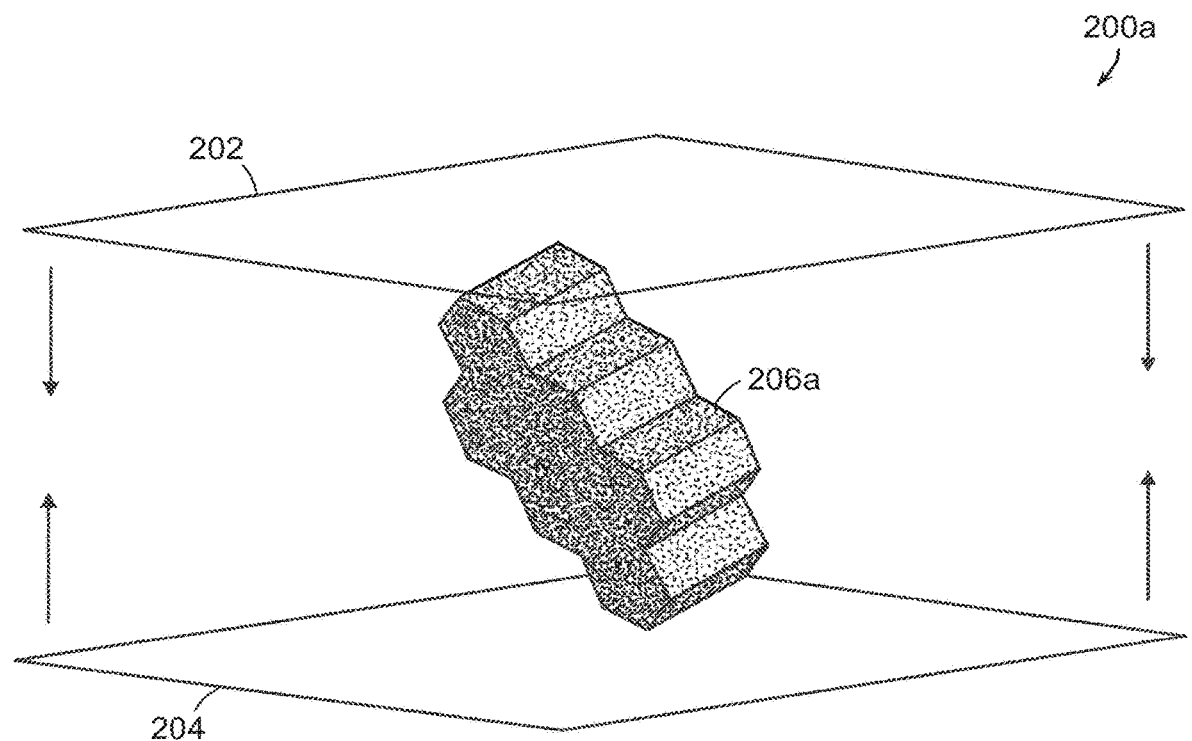
FIGS. 2A and 2B depict organ encasement system according to an embodiment of the invention.

In order to improve the function of organ perfusion systems, an organ encasement 200a is provided in FIG. 2A. The organ encasement 200a includes a first membrane 202 and a second membrane 204. The first membrane 202 and the second membrane 204 are pressed together to encase an organ 206a. The first membrane 202 and the second membrane 204 are flexible and therefor conform to the geometry of the organ 206a. Instead of resting on a few pressure points in a rigid vessel, the organ 206a is uniformly supported by one or more of the membranes 202, 204 in a manner similar to a human lying in a hammock.

In some embodiments, membranes 202 and 204 are formed by a single sheet of a biocompatible material that is folded upon itself.

Figure 2B:
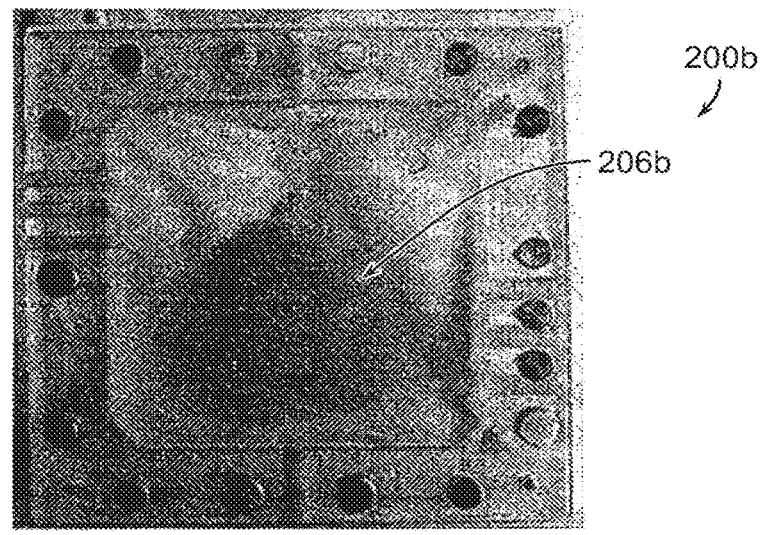

FIG. 2B depicts an embodiment of an organ encasement 200b encasing a rat liver 206b.

Preferably, membranes 202 and 204 are biocompatible materials. In some embodiments, the membranes 202, 204 are gas permeable. The membranes 202, 204 can also be elastic and/or deformable to better compliment the geometry of the organ 206.

Suitable membrane materials 202, 204 include medical-grade silicone membranes (also known as polydimethylsiloxane or PDMS). For example, the membranes 202, 204 can be fabricated from USP Class VI silicon. Silicone membranes are available from manufacturers such as McMaster-Carr Supply Company of Santa Fe Springs, Calif. and MedArray, Inc. of Ann Arbor, Mich. Other suitable membranes 202, 204 include thermoplastic or thermoset polymers, amniotic membranes, small intestinal submucosa (SIS), fascia, dura mater, peritoneum, pericardium, and the like.

In some embodiments, the membranes 202, 204 are transparent, translucent, or opaque. The membranes 202, 204 can be sterilized through various techniques (e.g., heat, steam, gases such as ethylene oxide or propylene oxide, and the like). Membranes 202, 204 can be water-repellant, capable of forming watertight seals, non-stick, have low chemical reactivity, and/or have low toxicity. In some embodiments, the membranes 202, 204 do not support microbiological growth.

Membranes 202 and 204 can be the same material or can be different materials. For example, if organ encasement is designed for orientation wherein the first membrane 202 is the upper membrane and the second membrane 204 is the lower membrane, first membrane 202 can be a membrane selected for maximal gas permeability and second membrane 204 can be selected for maximal compliance to better support organ 206.

In some embodiments, the organ encasement is suspended so that the organ encasement does not rest on a rigid surface, thereby causing pressure points on the organ 206 via one of membranes 202, 204. Suspension can be accomplished via a variety of devices. For example, one or more clips can attach to one or more of membranes 202, 204 to suspend the organ encasement device. In another example, a plurality of grommets can be formed one or more of membranes 202, 204 to suspend the organ encasement device 200. In still another example, a rigid or substantially rigid frame is interposed between membranes 202, 204. The rigid flume can then be supported or suspended on one or more supports.

Membranes 202, 204 can be coupled via a variety of means. For example, the membranes 202, 204 (and, in some embodiments, the rigid or substantially rigid frame) can be coupled by magnets, screws, bolts, nuts, rivets, adhesives, and/or zipper storage assemblies.

Membranes 202, 204 can be coupled to allow for one or more cannulae and/or lumens to pass between membranes 202, 204 for perfusion of organ 206, in some embodiments, membranes 202, 204 are fabricated with one or more access ports to receive one or more cannulae and/or lumens.

Methods of Harvesting Adult Cells

Figure 3:
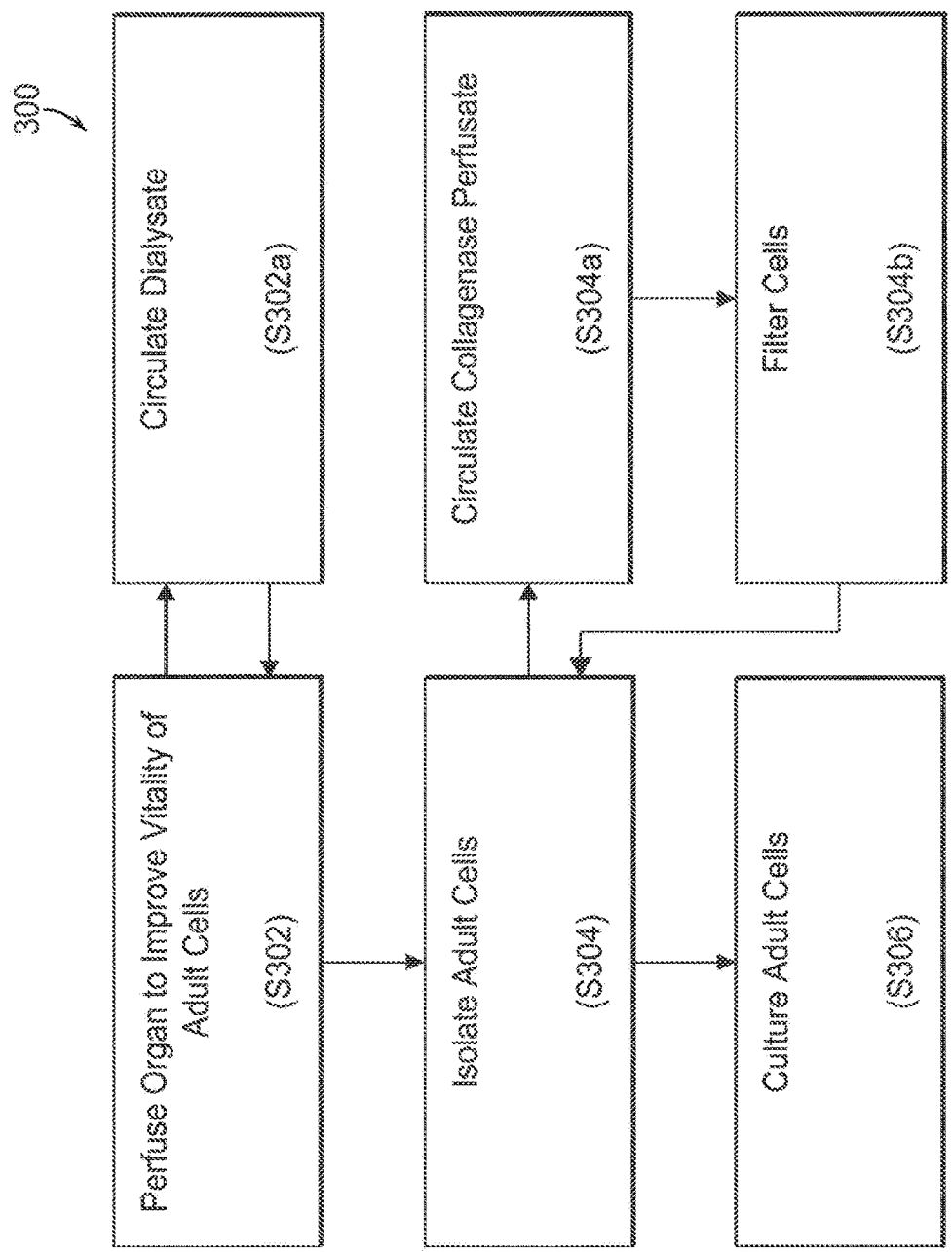
FIG. 3 depicts a method of harvesting adult cells according to an embodiment of the invention.

Referring to FIG. 3, a method 300 of harvesting adult cells is provided. In step S302, an organ is perfused with a perfusate to improve the vitality of the adult cells. Perfusion enhances the recovery of cells from damaged organs by improving cell health before the cells are isolated from the organ. Additionally, perfusion resuscitates damaged organs.

The organ culture perfusion step S302 can be accomplished in the organ perfusion system 100 described herein or in similar devices.

The organ culture perfusate in step S302 can vary to reflect varying species, organs, and organ health. For rat livers, about 50 mL of perfusate is sufficient. Several litters of perfusate may be required for human livers. In some embodiments, the perfusate include a solution having an osmolality of about 100 mOsm to about 500 mOsm, one or more oxygen carriers, one or more antioxidants, one or more anti-inflammatory agents, one or more vasodilators, one or more amino acids, one or more buffers, one or more inorganic salts, one or more substrates for metabolism, one or more hormones, one or more antibiotics, plasma, one or more anticoagulants, and/or one or more agents to maintain oncotic pressure for the perfusate between about 15 mm Hg and about 45 mm Hg.

The base solution can be Williams' Medium E solution (available from Sigma-Aldrich Corp. of St. Louis, Mo.). The one or more oxygen carriers can include erythrocytes (e.g., about 20% hematocrit). The one or more antioxidants can include bucillamine. See Farin Amersi, et al, "Bucillamine, a thiol antioxidant, prevents transplantation-associate reperfusion injury," 99(13) Proc. Nat'l Acad. Sci. 8915-20 (2002). The one or more anti-inflammatory agents can include hydrocortisone. The one or more vasodilators can include alpha-adrenoceptor antagonists ("alpha-blockers"), endothelin receptor antagonists ("ERAs"), angiotensin converting enzyme inhibitors ("ACE inhibitors"), and the like. The one or more amino acids can include L-argenine, L-glutamine, and the like. The one or more buffers can include phosphate buffered saline ("PBS"), Krebs-Ringer buffer ("KRB") (available from Sigma Aldrich, Inc. of St. Louis, Mo.), and the like. The one or more inorganic salts can include sodium, calcium, potassium, and the like. The one or more substrates for metabolism can include glucose and other carbohydrates, lactate, fatty acids, other energy sources, vitamins, and the like. The one or more hormones can include insulin (e.g., about 2 U/L). The one or more antibiotics can include (e.g., about 40,000 U/L) and/or streptomycin (e.g., about 40 mg/L). The plasma can have a volume-volume percentage of about 10%. The one or more anticoagulants can include heparin (e.g., about 1000 U/L), The one or more agents fur maintaining oncatic pressure can include albumin, polyethylene glycol, and the like.

In some embodiments, the oxygen tension of the perfusate is maintained between about 50 mm Hg and about 150 mm Hg. In some embodiments, the temperature of the perfusate is maintained between about 4° C. and about 42° C.

In some embodiments, the organ culture perfusion step S302 includes circulating a dialysate through a secondary circuit 120 (S302a).

In one embodiment, the operating parameters for the organ perfusions system 100 are as follows:

Flow rate=1.84±0.05 ml/min/g;
Portal hydrostatic pressure=12-16 cm $H_2O$ (8-12 mm Hg);
Hematocrit=17.8%±0.8%
Inlet oxygen pressure=128.4±8.1 mm Hg;
Outlet oxygen pressure=47.9±1.7 mm Hg;
Inlet carbon dioxide pressure=30.1±1.1 mm Hg; and
Outlet carbon dioxide pressure=34.6±1.6 mm Hg.

In step S304, adult cells are isolated from the organ. In one embodiment, the adult cells are isolated by perfusing the organ with a collagenase perfusate (step 304a). The collagenase perfusate can include a solution having an osmolality of about 100 mOsm to about 500 mOsm, one or more enzymes (e.g., collagenase I, collagenase II. collagenase III, collagenase IV, collagenase V, collagenase VI, trypsin, hyaluronidase and the like), one or more oxygen carriers, one or more antioxidants, one or more anti-inflammatory agents, one or more vasodilators, one or more amino acids, one or more buffers, one or more inorganic salts, one or more substrates for metabolism, one or more hormones, one or more antibiotics, plasma, and one or more anticoagulants. Collagenase IV can be obtained from *clostridium histolyticum* bacteria. The base solution and the components of the collagenase perfusate can be the same or similar to the organ culture perfusate described above.

The collagenase perfusate breaks the peptide bonds in collagen molecules in the organ to release the adult cells. The adult cells can be recovered from the collagenase perfusate through a variety of tissue culture methods. In one embodiment, the collagenase perfusate is filtered to isolate the adult cells (step 304b). For example, the collagenase perfusate can be filtered through one or more filters having pore sizes ranging from about 1 μm to about 1,000 μm. Additionally or alternatively, density centrifugation can be performed on the perfusate to isolate the adult cells from the collagenase perfusate.

In step S306, the adult cells are cultured in accordance with existing tissue culture methods. A variety of hepatocyte isolation and preservation protocols are described in U.S. Pat. Nos. 5,602,026 and 5,942,436, U.S. Patent Application Publication No. 2006/0019326, and James C. Y. Dunn et al., "Long-Term in Vitro Function of Adult Hepatocytes in a Collagen Sandwich Configuration," 7(3) Biotechnology Progress 237-45 (1991). Hepatocytes can be cryopreserved for later use as described in Claire Terry et al., "Cryopreservation of isolated human hepatocytes for transplantation: State of the art," 53 Cryobiology 149-59 (2006).

The cell isolation method 300 can recover a single type of cell or can recover multiple types of cells. For example, hepatocytes, endothelial cells, cholangiocytes (bile duct cells), Kupffer cells, stellate cells, and smooth muscle cells can be isolated from the liver. Other organs will yield different types of cells as will be appreciated by one of skill in the art. For example, islet cells (e.g., insulin-producing beta cells) or acinar cells can be isolated from the pancreas.

Preparation of Bioscaffolds

Figure 4:
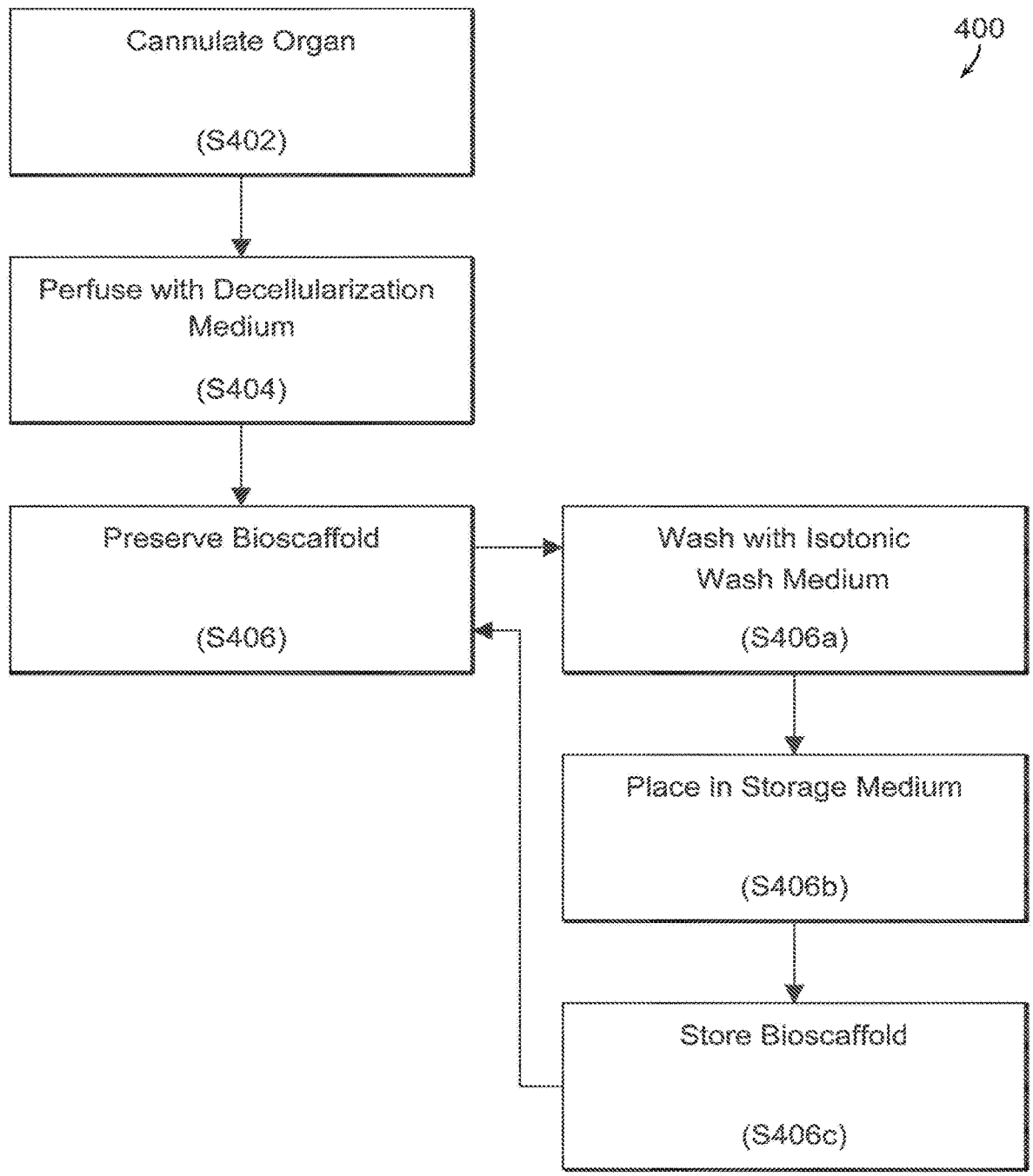
FIG. 4 depicts a method of preparing a bioscaffold according to an embodiment of the invention.

Referring to FIG. 4, a method 400 of preparing a bioscaffold is provided. In step S402, one or more vessels of the organ are cannulated.

In step S404, the organ is perfused with a decellularization medium. The decellularization medium can include one or more detergents, one or more vasodilators, one or more amino acids, one or more buffers, one or more inorganic salts, one or more substrates for metabolism, and/or one or more enzymes. The one or more detergents can include sodium dodecyl sulfate (SDS) and Triton X-100 ($C_{14}H_{22}O$ $(C_2H_4O)_n$) (available from Sigma Aldrich, Inc. of St. Louis, Mo.). The one or more vasodilators can include alpha-adrenoceptor antagonists ("alpha-blockers"), endothelin receptor antagonists ("ERAs"), angiotensin converting enzyme inhibitors ("ACE inhibitors"), and the like. The one or more amino acids can include L-glutamine, L-arginine, and the like. The one or more buffers can include phosphate buffered saline ("PBS"). The one or more inorganic salts can include sodium, calcium, potassium, and the like. The one or more substrates for metabolism can include glucose and other carbohydrates, lactate, fatty acids, other energy sources, vitamins, and the like. The one or more substrates for enzymes can include collagenase I, II, III, IV, V, or VI.

The decellularization medium can also include a serum as discussed in Ligiong Gui et al., "Novel Utilization of Serum in Tissue Decellularization," 16(2) Tissue Engineering 173-84 (2010). Suitable serums include human serum and non-human serums such as fetal bovine serum (FBS), porcine serum, and the like. Serums can be selected from the same or different species as the organ to be decellularized and can even be provided from the donor of the organ and/or recipient of a recellularized organ to be fabricated from the organ.

One or more serums can be mixed with other materials as discussed herein and Gui et al. and can be administered as part of a single decellularization medium or as part of a follow-on decellularization medium to further remove DNA after an initial decellularization.

The temperature of the decellularization medium can be maintained between about 4° C. and about 42° C. The decellularization process may last between about 4 hours and about one month. For example, the decellularization process may last for about 5 hours, about 6 hours, about 7 hours, about 8 hours, about 9 hours, about 10 hours, about 11 hours, about 12 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 21 days, about 28 days, and the like.

In step S406, the bioscaffold is preserved. In step S406a, the bioscaffold can be washed with one or more isotonic wash mediums (e.g., saline, phosphate buffered saline, and the like). In step S406b, the bioscaffold can be placed in storage medium that includes one or more antimicrobial agents. The storage medium can include one or more antimicrobial agents. The one or more antimicrobial agents can include one or more antibiotics and/or fungicides. The one or more antibiotics and/or fungicides can include penicillin (e.g., about 40,000 U/L), streptomycin (e.g., about 40 mg/L), (amphotericin B (e.g., about 2.5 µg/mL), and the like.

In step S406c, the bioscaffold can be stored. A variety of storage techniques can be employed. In one embodiment, the bioscaffold is stored at room temperature, at less than about 4° C., at about −20° C. or about −40° C. in a freezer), or at about −180° C. (e.g., in liquid nitrogen). In another embodiment, the bioscaffold can be perfused indefinitely. In other embodiment, the bioscaffold is dried. In still another embodiment, the bioscaffold is stored using subzero non-freezing techniques as described in publications such as Joaquín V. Rodríguez et al., "Subzero nonfreezing storage of rat hepatocytes using modified University of Wisconsin solution (mUW) and 1,4-butanediol. I-effects on cellular metabolites during cold storage," 8(1) Annals of Hepatology 57-62 (2009).

Methods of Preparing Artificial Organs

Figure 5:
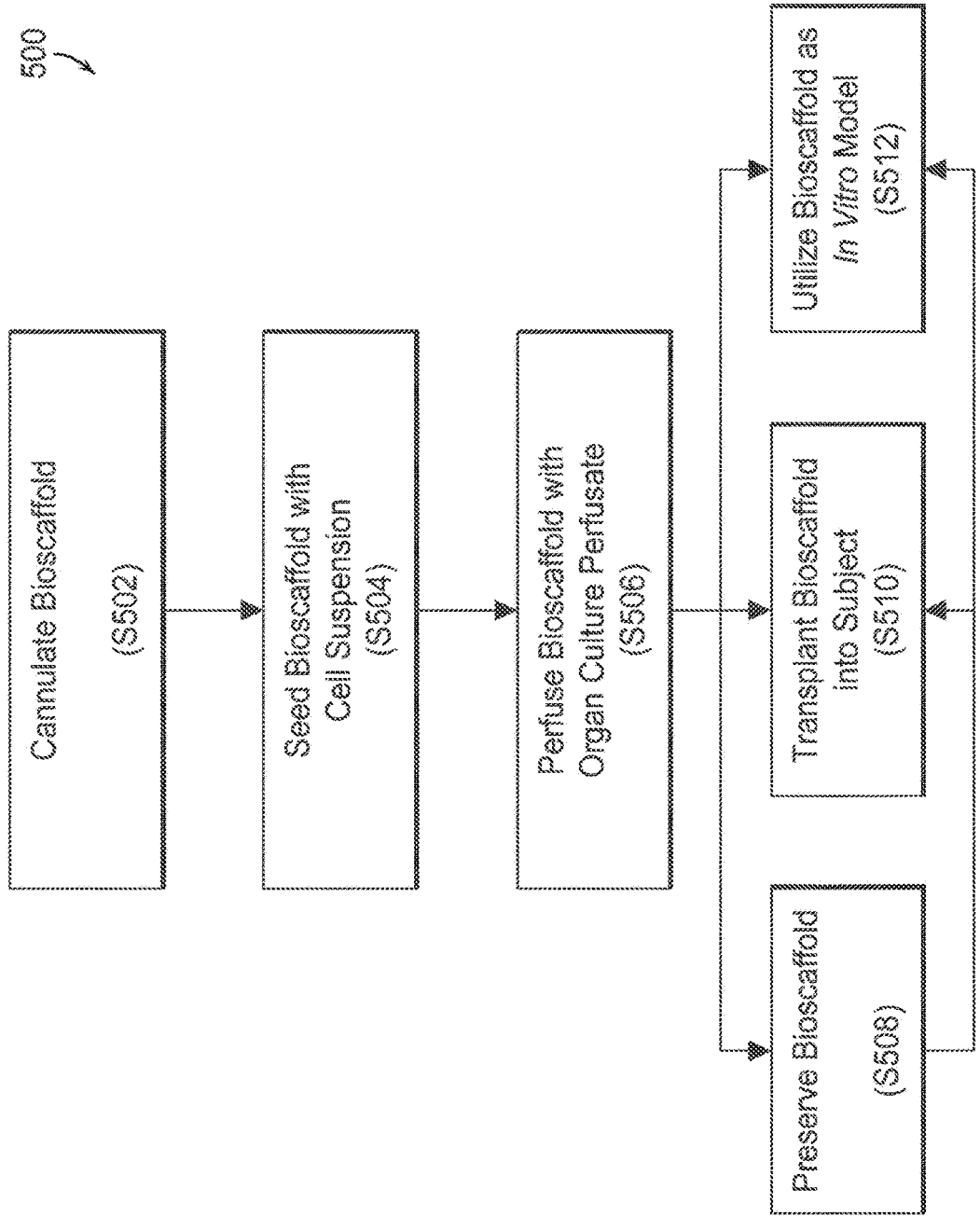
FIG. 5 depicts a method of recellularizing a bioscaffold according to an embodiment of the invention.

Referring to FIG. 5, a method 500 of preparing an artificial organ from a bioscaffold is provided.

In some embodiments, the bioscaffold can be a decellularized organ, for example, a decellularized organ prepared according to the methods provided herein. In other embodiments, the bioscaffold is a bioartificial organ device such as those described in U.S. Pat. No. 7,371,400 and U.S. Patent Application Publication Nos. 2006/0019326 and 2007/0148139.

In step S502, one or more vessels of the bioscaffold are cannulated.

In step S504, the bioscaffold is seeded with a cell suspension. In some embodiments, the cell suspension includes a solution having an osmolality ranging front about 100 mOsm to about 500 mOsm, a plurality of cells of one or more types, one or more oxygen carriers, one or more antioxidants, one or more anti-inflammatory agents, one or more vasodilators, one or more amino acids, one or more buffers, one or more inorganic salts, one or more substrates for metabolism, one or more hormones, one or more antibiotics, plasma, one or more anti-coagulants, and/or one or more agents to maintain oncotic pressure of the suspension between about 15 and about 45 mm Hg.

The cell suspension can include a single type of cells or multiple types of cells. For example, a liver bioscaffold can be seeded with hepatocytes, endothelial cells, cholangiocytes (bile duct cells), Kupffer cells, stellate cells, and/or smooth muscle cells. In another example, a pancreas bioscaffold can be seeded with islet cells (e.g., insulin-producing beta cells) or acinar cells. Particular cell types can be seeded in specific locations of the bioscaffold. Alternatively, each cell type can be generally perfused throughout the bioscaffold.

The cell suspension can, but need not, include cells harvested from the same species as the bioscaffold and/or the recipient of the recellularized bioscaffold.

The base solution can be Williams' Medium E solution (available from Sigma-Aldrich Corp. of St. Louis, Mo.). The one or more oxygen carriers can include erythrocytes (e.g., about 20% hematocrit). The one or more antioxidants can include bucillamine. The one or more anti-inflammatory agents can include hydrocortisone. The one or more vasodilators can include alpha-adrenoceptor antagonists ("alpha-blockers"), endothelin receptor antagonists ("ERAs"), angiotensin converting enzyme inhibitors ("ACE inhibitors"), and the like. The one or more amino acids can include L-glutamine, L-arginine, and the like. The one or more buffers can include phosphate buffered saline ("PBS"). The one or more inorganic salts can include sodium, calcium, potassium, and the like. The one or more substrates for metabolism can include glucose and other carbohydrates, lactate, fatty acids, other energy sources, vitamins, and the like. The one or more hormones can include insulin (e.g., about 2 U/L). The one or more antibiotics can include penicillin (e.g., about 40,000 U/L) and/or streptomycin (e.g., about 40 mg/L). The plasma can have a volume-volume percentage of about 10%. The one or more agents for maintaining oncotic pressure can include albumin, polyethylene glycol, and the like.

The bioscaffold can be seeded by perfusing the bioscaffold with the cell suspension. In other embodiments, the bioscaffold is seeded by injecting the bioscaffold with the cell suspension in one or more locations. In still other embodiments, the bioscaffold is seeded by injecting cells in multiple phases as discussed herein in the context of FIG. 25.

In step S506, the recellularized bioscaffold is perfused with an organ culture perfusate to promote engrafting of the cells to the bioscaffold and organ function. The organ culture perfusate can include the same or similar components of the perfusate for enhancing cell vitality as described herein. The recellularized bioscaffold can be perfused for hours, days, weeks, months, or indefinitely. For example, the recellularized bioscaffold can be perfused for about 4 hours, about 8 hours, about 12 hours, about 16 hours, about 20 hours, about 1 day, about 2 days, about 3 days, about 4 days, about 5 days, about 6 days, about 7 days, about 8 days, about 9 days, about 10 days, about 11 days, about 12 days, about 13 days, about two weeks, about three weeks, and about one month.

In step S508, the recellularized bioscaffold is preserved. The recellularized bioscaffold can be preserved in a manner similar to the preservation of a decellularized organ as discussed herein, namely washing with one or more isotonic wash mediums, continuous perfusion, drying, storage in a medium including one or more antimicrobial agents, storage at less than about 4° C., about −20° C., about −40° C., and about −180° C., and/or subzero nonfreezing storage.

In step S510, recellularized bioscaffold can be transplanted into a subject by a health care provider in accordance with known surgical techniques. Alternatively, in step S512, the recellularized bioscaffold can be used an in vitro model (e.g., an in vitro pharmacologic model) in accordance with known laboratory techniques such as those described in U.S. Patent Application Publication No. 2006/0019326.

Methods of Organ Rehabilitation

Figure 6:
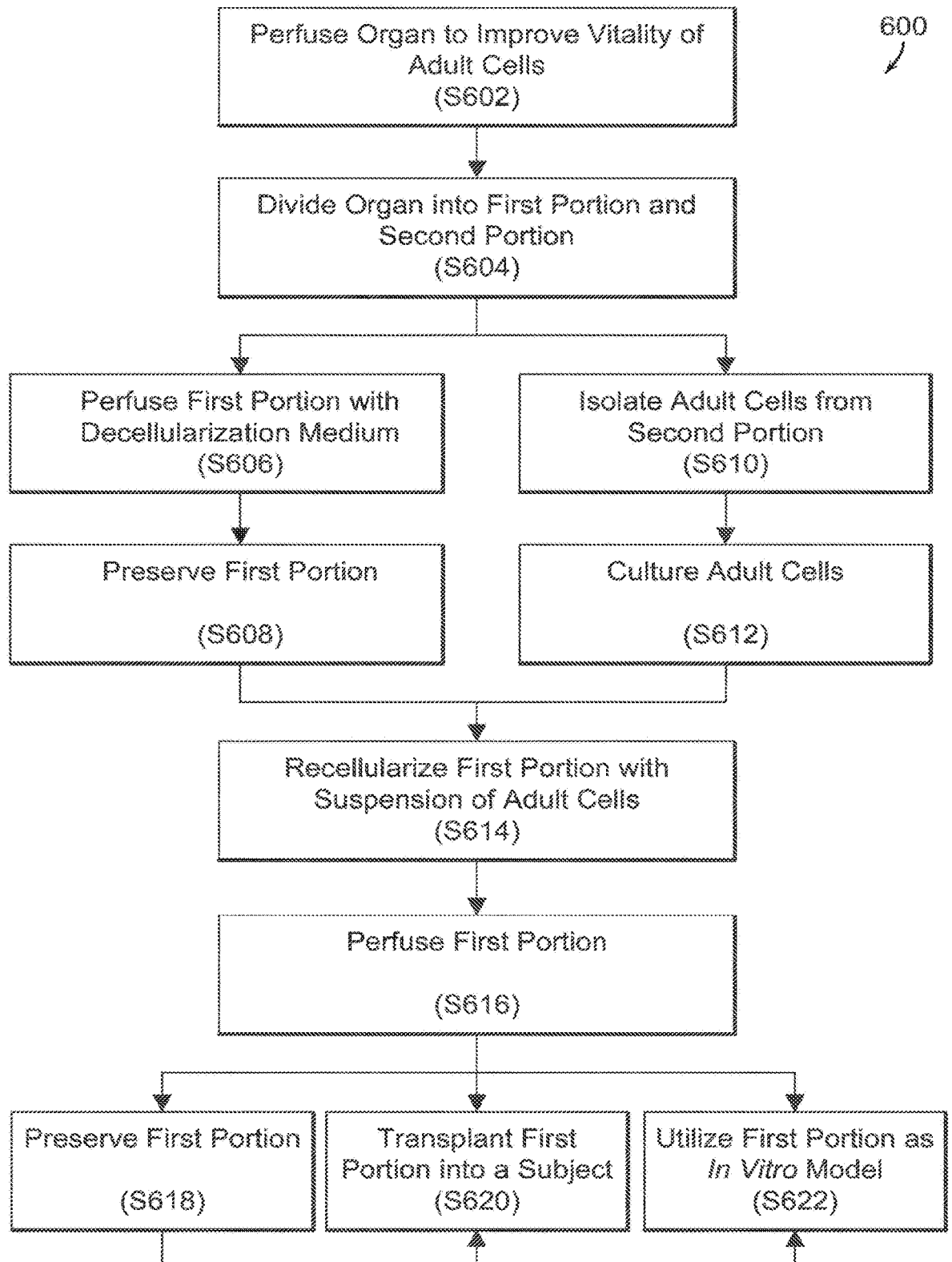
FIG. 6 depicts a method of organ rehabilitation according to an embodiment of the invention.

Referring to FIG. 6, a method 600 of organ rehabilitation is provided. Organ rehabilitation can be particularly advantageous because, in some embodiments, a rehabilitated organ can be fabricated solely from a subject's own organ, thereby minimizing the risk of transplant rejection. Accordingly, in some embodiments the organ can be harvested from the subject, rehabilitated according to the method below, and transplanted to the same subject. During the interim period when the rehabilitation method is performed, the subject can be sustained with one or more external support systems (e.g. dialysis machines) and/or internal bioartificial organ devices (e.g. bioartificial liver devices) such as those described in U.S. Patent Application Publication No. 2007/0148139.

In step S602, the organ is perfused to improve the vitality of adult cells as described herein.

In step S604, the organ is divided into first portion and a second portion. Division of the organ into the first and section portion can be accomplished using existing surgical techniques, including, but not limited to living donor transplantation techniques. For example, in living donor liver transplantation (LDLT) techniques, either the right lobe or the left lobe of the liver is resected from the donor for transplantation to the recipient. LDLT techniques are described in publications such as S. A. Shah et al, "Adult-to-adult living donor liver transplantation," 20(5) Can, J. Gastroenterol. 339-43 (2006); and Chi Leung Liu et al., "Operative Outcomes of Adult-to-Adult Right Lobe Live Donor Liver Transplantation: A Comparative Study With Cadaveric Whole-Graft Liver Transplantation in a Single Center," 243(3) Annals of Surgery 404-10 (2006).

The first portion and the second portion are processed independently. In steps S606 and S608, the first portion is perfused with a decellularization medium and preserved, as described herein. In step S610 and S612, the adult cells are cultured as described herein.

In steps S614 and S616, the first portion is recellularized with a suspension of adult cells as described herein and perfused with an organ culture perfusate as described herein.

In step S618, the first portion is preserved. The first portion can be preserved. in a manner similar to the preservation of a decellularized organ as discussed herein, namely washing with one or more isotonic wash mediums, continuous perfusion, drying, storage in a medium including one or more antimicrobial agents, storage at less than about 4° C., about −20° C., about −40° C., and about −180° C., and/or subzero nonfreezing storage.

In step S620, the first portion can be transplanted into a subject by a health care provider in accordance with known surgical techniques.

In some embodiments, the first portion and the second portion are substantially equal in size (e.g. mass and/or volume). In another embodiment, the first portion is larger than the first portion to provide for a larger vascular structure to support an increased number of cells. In still another embodiment, the first and the second portion are selected based on the relative health of the vascular structure and the target cells in the various regions of the organ. For example, if "region A" of an organ had relatively intact vasculature and "region B" of the organ had relatively healthy target cells, region A could be selected decellularization and region B could be selected for cell isolation.

Use of Recellularized Organs for Research

Recellularized organs can be used in a variety of research applications. For example, recellularized organs (e.g., recellularized livers) can be used for drug discovery (e.g., ADMET testing). Entire recellularized organs or portions thereof can be used, depending on the needs of a particular application.

Referring again to step S512 of FIGS. 5 and S622 of FIG. 6, a recellularized bioscaffold or recellularized first portion of an organ (collectively referred to as a "recellularized bioscaffold") can be used as an in vitro model. The entire recellularized bioscaffold can be used as an in vitro model. Alternatively, the recellularized bioscaffold can be sliced accordingly to existing laboratory techniques and plated for use as an in vitro model.

Figure 7A:
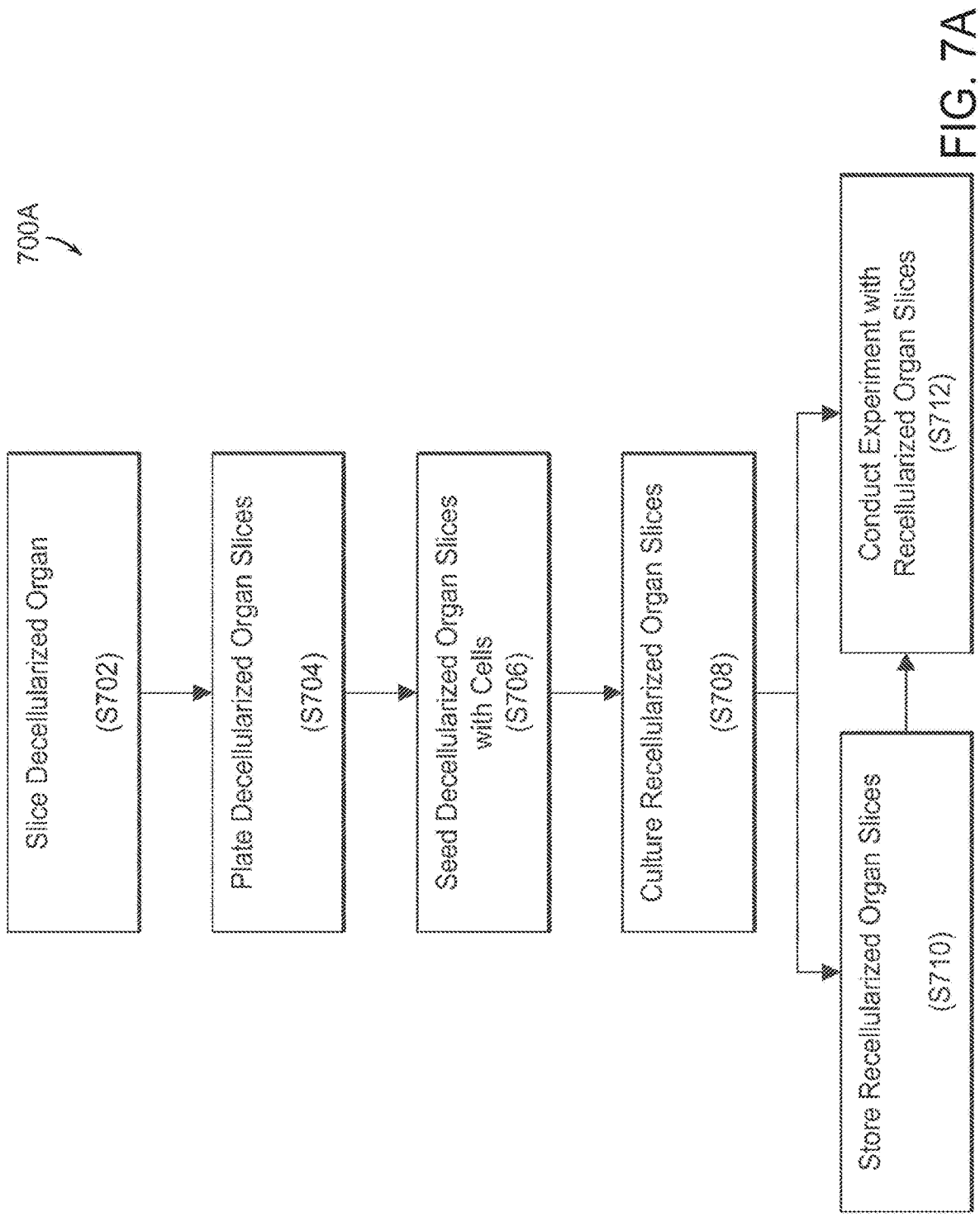
FIGS. 7A and 7B depict methods of creating a research tool according to embodiments of the invention.

Referring now to FIG. 7A, another method 700A of creating a research tool is provided.

In step S702, a decellularized organ is sliced according to existing laboratory techniques. The decellularized organ can be produced according to the methods described herein or other methods. Additionally or alternatively, one or more mechanical methods such as agitation and/or sonication can be used to decellularize the organ.

In step S704, the decellularized organ slice is plated in a vessel such as a Petri dish. The Petri dish can, in some embodiments, contain an agar to support the organ slice and cells added in step S706.

In step S706, the decellularized organ slice is seeded with cells. The cells can be seeded by placing the cells on top of the decellularized organ slice (e.g., by pouring or transferring a recellularization medium containing the cells with a pipette or other device). In step S708, the recellularized organ slices are cultured, for example, with a culture medium described herein.

In step S710, the recellularized organ slices are stored according to existing laboratory protocols. In step S712, the recellularized organ slices are used in an experiment (e.g., a pharmacologic experiment). For example, one or more test agents can be applied to the recellularized organ slice. The one or more test agents and the recellularized organ slice can then be incubated to form an enzyme-substrate complex between the one or more test agents and one or more enzymes contained in the recellularized organ slice. One or more metabolites of the test agent can be then be detected with various laboratory techniques (e.g., mass spectrometry, fluorescence screening, and the like).

Referring now to FIG. 78, another method 700B of creating a research tool is provided.

In step S714, an organ is sliced according to existing laboratory techniques.

In step S716, the organ slices are placed in a vessel such as a Petri dish. The Petri dish can, in some embodiments, contain an agar to support the organ slice and cells added in step S720.

In step S718, the organ slice is decellularized, for example, by exposing the organ slice to a decellularization medium as discussed herein. Additionally or alternatively, one or more mechanical methods such as agitation and/or sonication can be used to decellularize the organ slice.

Figure 7B:
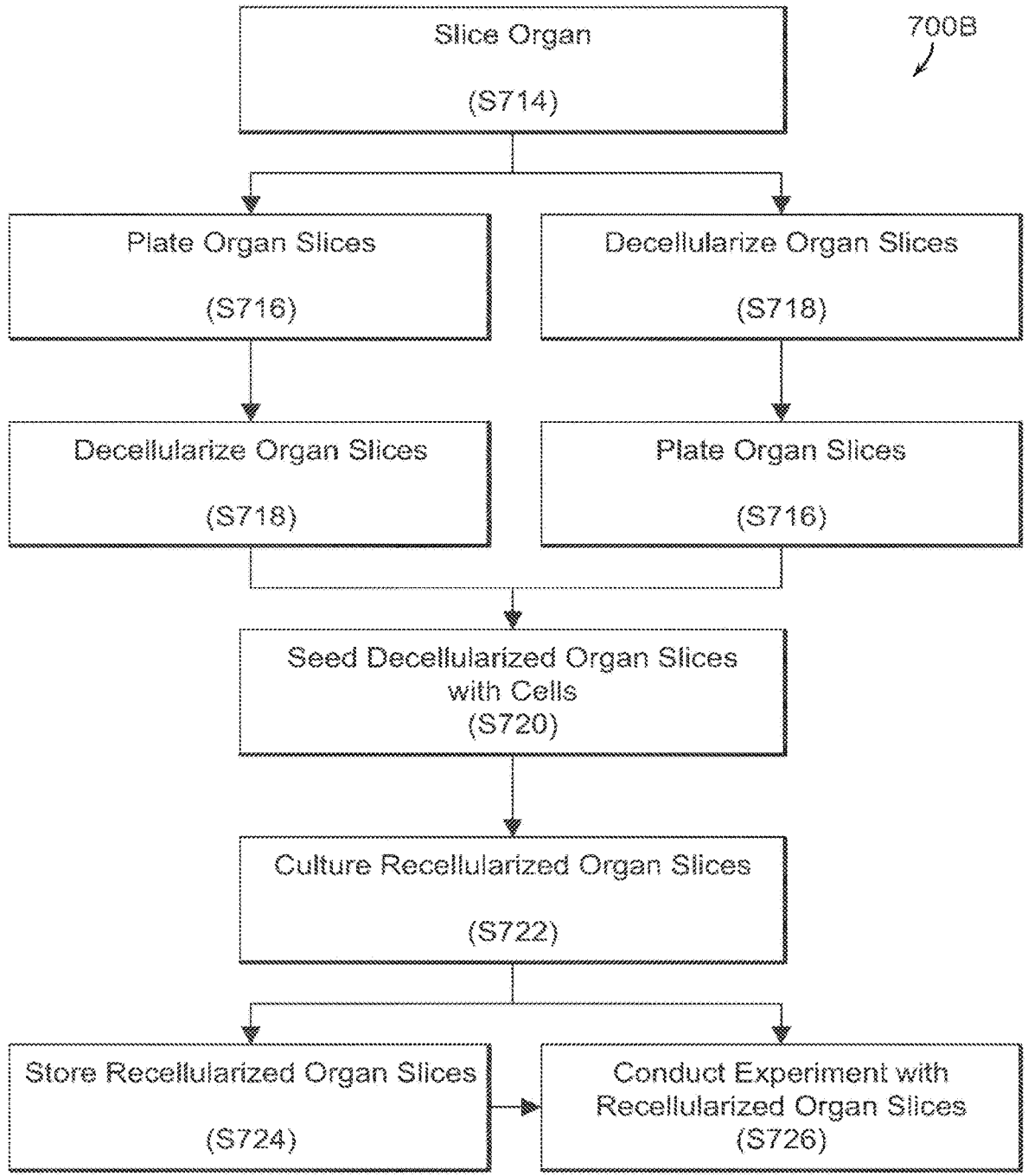

As depicted in FIG. 7B, steps S716 and S718 can be performed in any order (i.e., the organ can be plated before decellularization or can be decellularized after plating).

In step S720, the decellularized organ slice is seeded with cells. The cells can be seeded by placing the cells on top of the decellularized organ slice (e.g., by pouring or transferring a recellularization medium containing the cells with a pipette or other device). In step S722, the recellularized organ slices are cultured, for example, with a culture medium described herein.

In step S724, the recellularized organ slices are stored according to existing laboratory protocols. In step S726, the recellularized organ slices are used in an experiment (e.g., a pharmacologic experiment). For example, one or more test agents can be applied to the recellularized organ slice. The one or more test agents and the recellularized organ slice can then be incubated to form an enzyme-substrate complex between the one or more test agents and one or more enzymes contained in the recellularized organ slice. One or more metabolites of the test agent can be then be detected with various laboratory techniques (e.g., mass spectrometry, fluorescence screening, and the like).

Test agents can include, but are not limited to, opioid analgesics, anti-inflammatory drugs such as antihistamines and non-steroidal anti-inflammatory drugs (NSAIDs), diuretics such as carbonic anhydrase inhibitors, loop diuretics, high-ceiling diuretics, thiazide and thiazide-like agents, and potassium-sparing diuretics, agents that impinge on the renal and cardiovascular systems such as angiotensin-converting enzyme inhibitors, cardiac drugs such as organic nitrates, calcium channel blockers, sympatholytic agents, vasodilators, β-adrenergic receptor agonists and antagonists, α-adrenergic receptor agonists and antagonists, cardiac glycosides, anti-arrhythmic drugs, agents that affect hyperlipoproteinemias such as 3-hydroxymethylglutaryl-coenzyme A (HMG-CoA) inhibitors, anti-neoplastic agents such as alkylating agents, antimetabolites, natural products, antibiotics, and other drugs, immunomodulators, anti-diabetic agents, and anti-microbial agents such as antibacterial agents, antiviral agents, antifungal agents, antiprotozoal agents, and antihelminthic agents.

Enzymes can include, but are not limited to, cytochrome P450, alkaline phosphatase, α-galactosidase, β-galactosidase, α-glucosidase, β-glucosidase, glucuronidase, β-glucuronidase, α-amylase, NADPH-cytochrome P450 reductase, cytochrome $b_5$, N-demethylase, O-demethylase, acetylcholinesterase, pseudocholinesterase, epoxide hydrolase, amidases, uridine diphosphate (UDP)-glucuronosyltransferases, phenol sulfotransferase, alcohol sulfotransferase, sterid sulfotransferase, and arylamine sulfotransferase, UDP-glycosyltransferases, purine phosphoribosyltransferase, N-acetyltransferases, glutathione S-transferase, phenylethanolamine N-methyltransferase, non-specific N-methyltransferase, imidazole N-methyltransferase, catechol-O-methyltransferase, hydroxyindole-O-methyttransferase, S-methyltransferase, alcohol dehydrogenase, aldehyde dehydrogenase, xanthine oxidase, monoamine oxidases, diamine oxidases, flavoprotein N-oxidases, hydroxylases, aromatases, cysteine conjugate β-lyase, and alkylhydrazine oxidase. The enzyme can be endogenously expressed in the recellularized organ slice, and can have either normal enzymatic activity or altered enzymatic activity, for example, such as where the enzyme contains a polymorphism or mutation.

WORKING EXAMPLE #1

Use of Normothermic Perfusion to Restore Organ Vitality

As a model of Donors after Cardiac Death (DCD), lean livers were harvested from rats (inbred Lewis strain) and held at 34° C. for 60 min. This temperature is slightly lower than physiological, which is justified by the fact that core body temperature tends to decrease after death. After one hour of ischemia, the livers were perfused for five hours in the organ perfusion system depicted in FIG. 1 using the methods described above. Perfusate samples (1 ml) were collected from the inlet of the liver and analyzed using a PICCOLO® miniature blood chemistry analyzer available from Abaxis, Inc. of Union City, Calif.

Figure 8A:
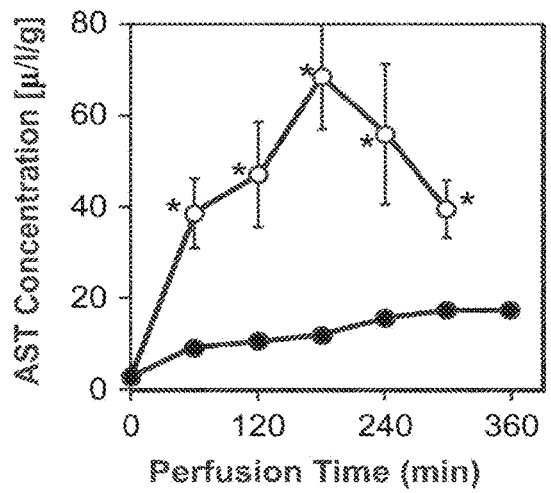
FIGS. 8A-8E depict functional parameters of perfused ischemic livers during normothermic perfusion as compared to perfused fresh livers.
Figure 8B:
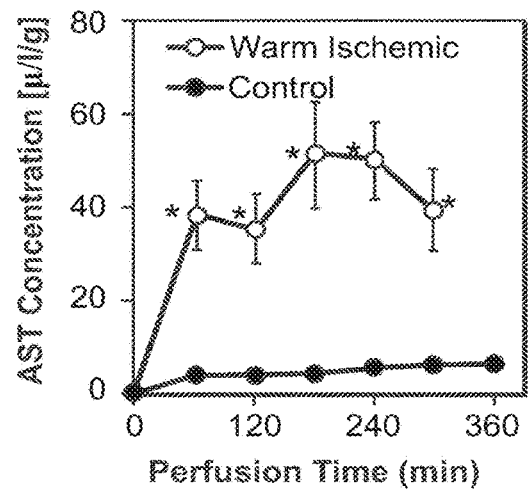

FIGS. 8A-8E depict functional parameters of harvested livers during normothermic perfusion. Alanine transaminase (ALT) and aspartate transaminase (AST) activities are depicted in FIGS. 8A and 8B as indicators of hepatocellular damage. Both AST and ALT accumulated during the first 180 minutes of perfusion and then decreased. These values were severalfold higher than those for the control group of freshly isolated livers not subjected to any warm ischemia. Neither ALT nor AST were detected in the dialysate (data not shown).

Figure 8C:
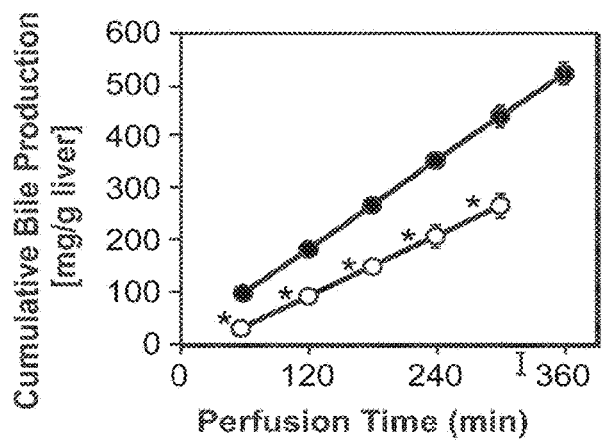
Figure 8D:
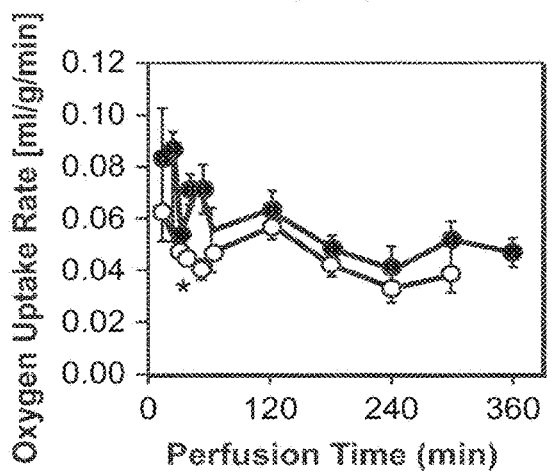
Figure 8E:
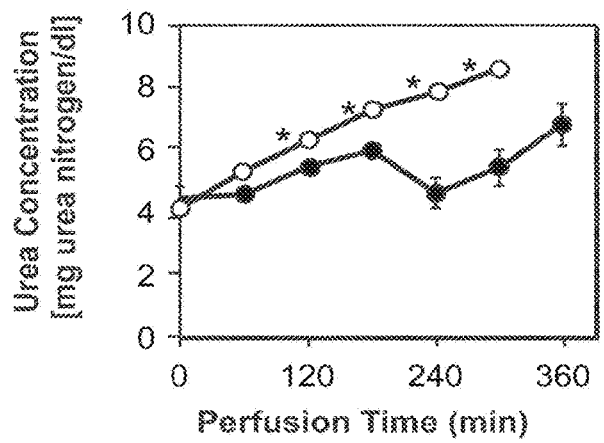

Bile secretion and oxygen consumption describe the metabolic state of the liver. Bile was produced at a constant rate throughout the perfusion as depicted in FIG. 8C. This rate was 40% lower compared to freshly isolated livers. The Oxygen Uptake Rate (OUR) of warm ischemic livers declined rapidly during the first 60 minutes of the perfusion and then remained stable as depicted in FIG. 8D. This behavior was very similar to the control group. The OURs of the perfused warm ischemic and freshly isolated livers were very similar in the plateau region beyond 60 minutes. The urea level in the perfusate showed a steady increase from 4.20 mg/dL at t=0 to 8.60 mg/dL at t=300 minutes, indicating a constant rate of urea production. This rate was consistently higher than that observed in perfused healthy livers as depicted in FIG. 8E. The bile and oxygen uptake values were significantly lower than the control group and the urea levels were significantly higher than the control group (p<0.01 by ANOVA). Asterisks (*) in FIGS. 8A-4E indicate a statistical difference compared to healthy perfused livers as p<0.1

Warm ischemic livers were transplanted into recipient rats after five hours of normothermic perfusion (n=13) or five hours of Static Cold Storage (SCS) in University of Wisconsin solution at 0° C. (n=6). In addition, freshly isolated livers not subjected to any warm ischemia were transplanted after six hours of SCS (n=6) or normothermic perfusion (n=11) and ischemic livers were transplanted directly without having undergone preservation (n=9).

Transplantation of perfusion-treated ischemic livers was uneventful in all but one case, where bleeding at the anastomosis occurred. All animals recovered from anesthesia rapidly. The animal that bled during surgery died on day four postoperatively. The other recipient animals survived beyond one month and did not exhibit external signs of liver failure, such as jaundice.

Figure 9:
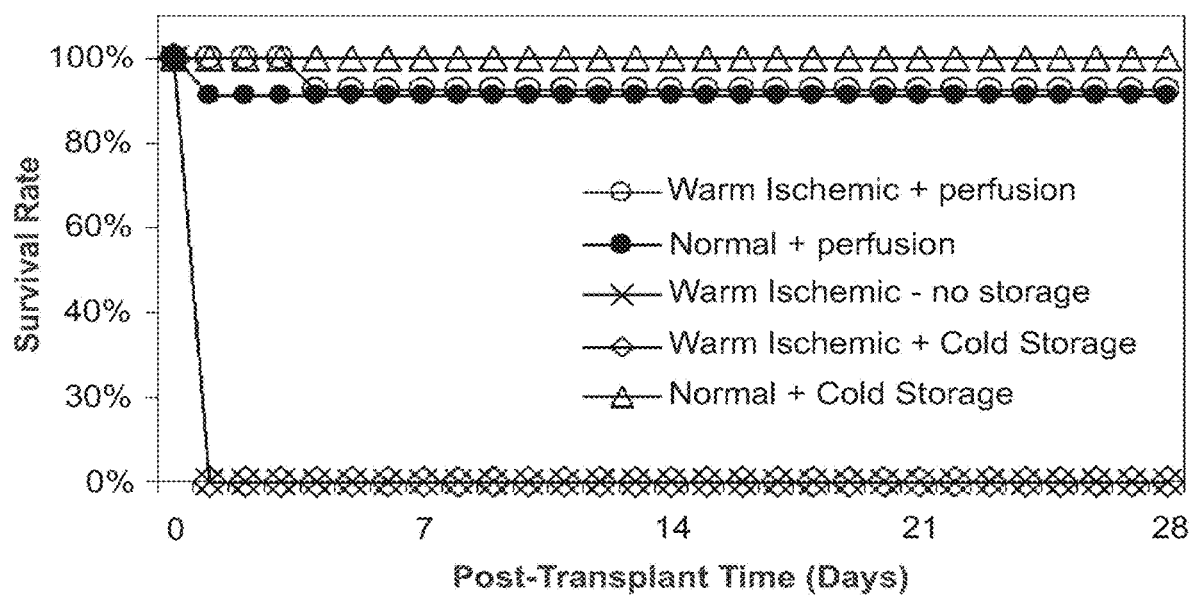
FIG. 9 depicts survival rates of transplant recipients of perfused ischemic rat livers compared to survival rates of recipients of fresh (normal) and warm ischemic livers with different modalities of preservation.

No surgical complications occurred during transplantation of ischemic livers preserved by SCS and recipients recovered rapidly from anesthesia, but within six hours, all developed symptoms of primary nonfunction and died within 12 hours. Autopsy revealed patchy livers and serous fluid in the abdomen. All recipients of directly transplanted ischemic livers died in a similar way within 24 hours post-operatively. All controls that received freshly isolated livers preserved for six hours by SCS recovered rapidly from surgery and survived beyond one month. Survival rates are depicted in FIG. 9.

Because primary nonfunction indicates disruption of liver microcirculation and death of parenchymal and nonparenchymal cells, in this context recipient death due to primary nonfunction is an indicator of poor conditions for hepatocyte isolation compared to livers that demonstrate no such symptoms. Accordingly, these results provide strong evidence that normothermic perfusion enhances viability of damaged livers for hepatocyte isolation.

Figure 10:
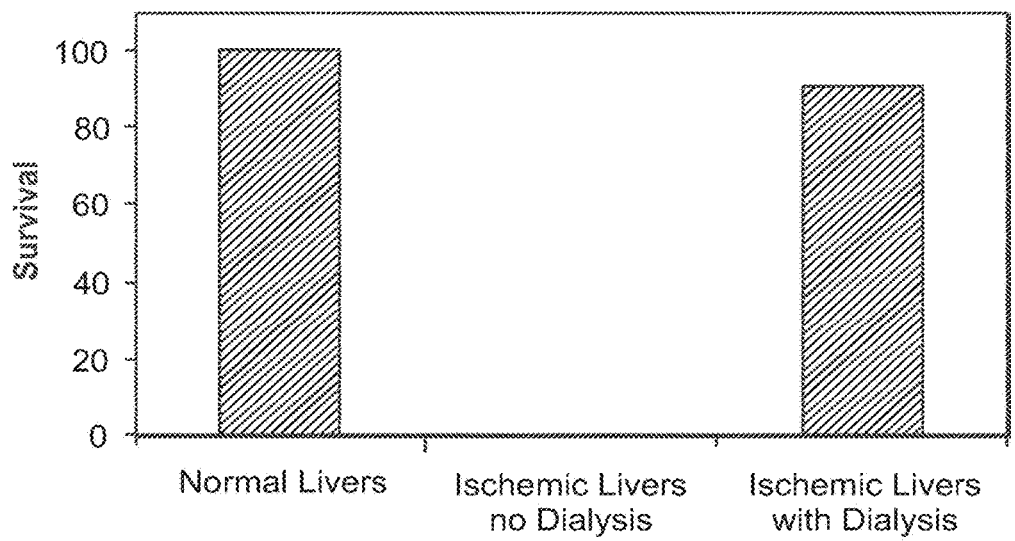
FIG. 10 depicts a comparison of survival rates for transplant recipients of perfused ischemic livers compared with different versions of the perfusion systems described herein.

Additionally, as depicted in FIG. 10, the use of an organ perfusion system 100 with a secondary dialysis circuit 120 yields significantly better results than perfusion without a secondary dialysis circuit 120. (Survival rates are shown at four weeks post-operation; n>6 for all groups).

WORKING EXAMPLE #2

Isolation of Hepatocytes from Livers after Normothermic Perfusion

Lean livers were harvested from heparinized Lewis rats and held at 34° C. for 60 minutes. After one hour of ischemia, one group of livers was perfused in the organ perfusion system depicted in FIG. 1, and cell isolation was performed with livers in the other group. Hepatocytes were isolated using a two-step collagenase perfusion procedure as described previously James C. Y. Dunn et al., "Long-Term in Vitro Function of Adult Hepatocytes in a Collagen Sandwich Configuration," 7(3) Biotechnology Progress 237-45 (1991).

For short-term function evaluation, recovered hepatocytes were cultured in suspensions ($1\times10^6$ cells/mL) for six hours with continuous gentle mixing in an incubator in 90% air/10% $CO_2$ at 37° C.

For long-term function evaluation, recovered hepatocytes were cultured in the double gel sandwich configuration to maintain stable liver specific function. Briefly, tissue culture dishes were coated with a mixed solution of nine parts type 1 rat tail collagen (1.1 mg/mL) and one part 10× Dulbecco's Modified Eagle's Medium (DMEM) and incubated for one hour at 37° C. to forma collagen gel. After gelation, 125,000 cells per well were seeded in nine-well culture dishes, and incubated in 90% air/10% CO2 at 37" C. The following day, after aspirating the culture medium from the dishes, the second collagen gel layer was overlaid on the hepatocytes and incubated for one hour at 37° C. After gelation, 1 mL of hepatocyte culture medium was applied, and then changed daily.

Standard hepatocyte culture medium used both in suspension and collagen gel cultures includes DMEM with 10% fetal bovine serum, 7 ng/mL glucagon, 7.5 µg/mL hydrocortisone, 0.5 insulin, 20 ng/mL epidermal growth factor, 200 U/mL penicillin, and 200 µg/mL streptomycin. Group comparisons were performed via a t-test.

Figure 11A:
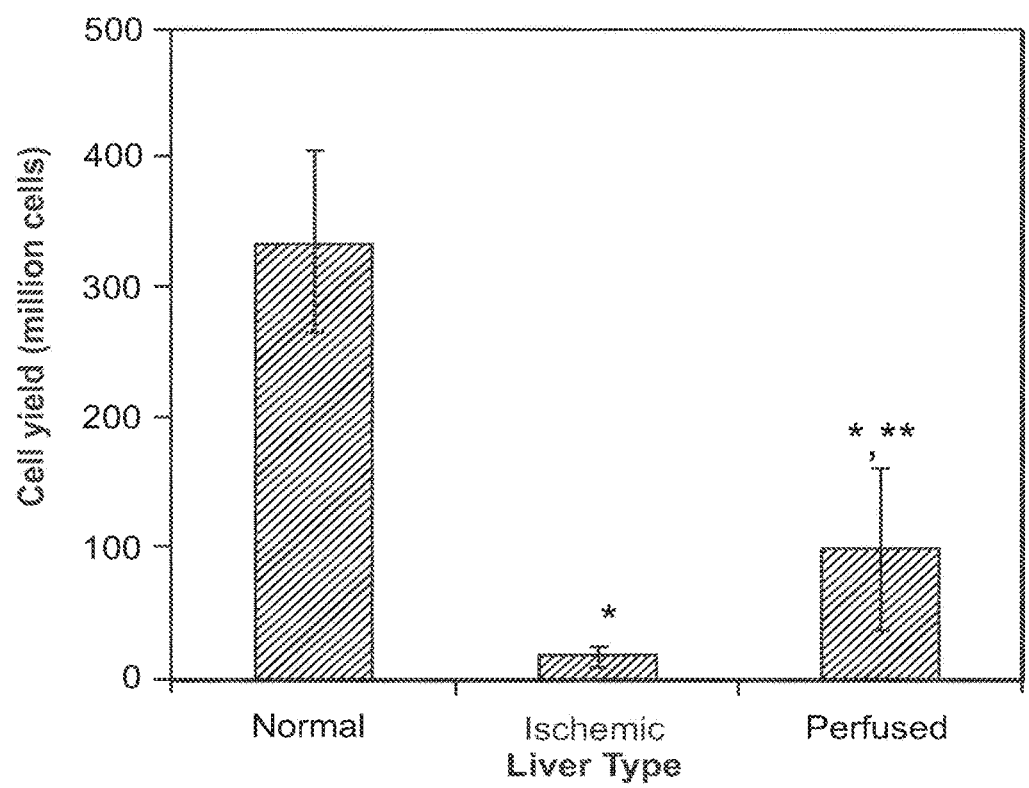
FIGS. 11A and 11B depict cell yields and viability for harvested livers.
Figure 11B:
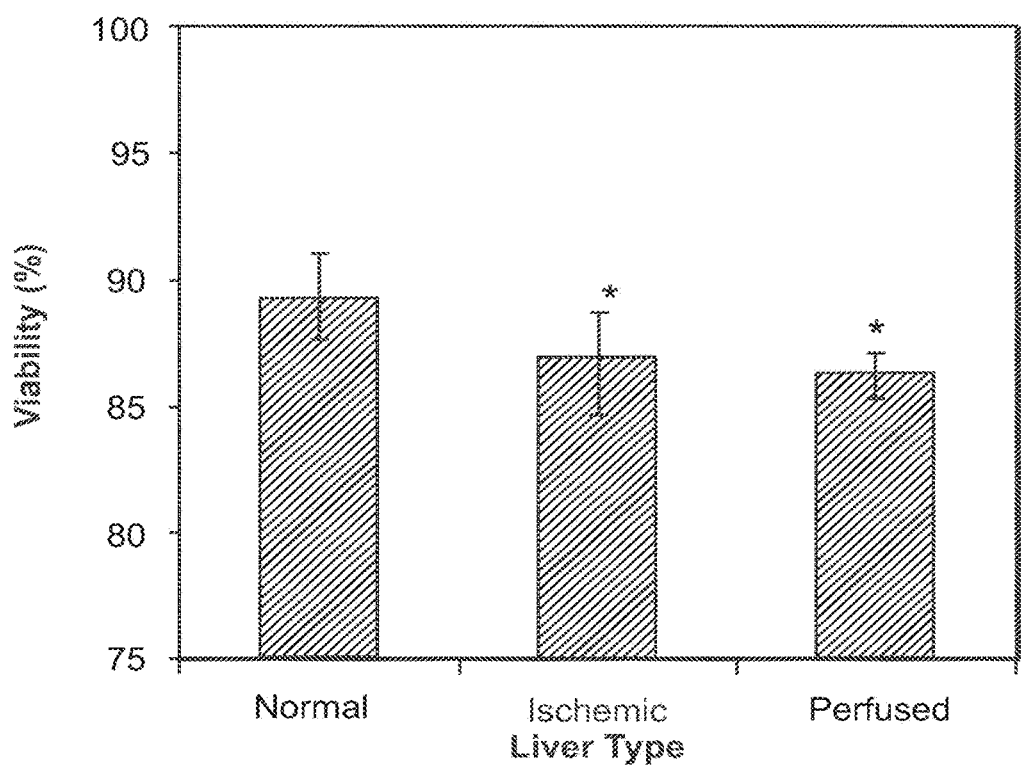

As depicted in FIG. 11A, the cell yield is increased from 15 million to 100 million. As depicted in FIG. 11B, the viability of these recovered cells are well in the acceptable range (>85%), although slightly lower than obtained with non-ischemic livers. A single asterisk (*) denotes a statistically significant difference as compared to normal livers. A double asterisk(**) denotes a statistically significant difference as compared to ischemic, non-perfused livers (p<0.05). These results demonstrate that normothermic perfusion increases the number of cells isolated from ischemic livers by approximately sixfold.

Figure 12A:
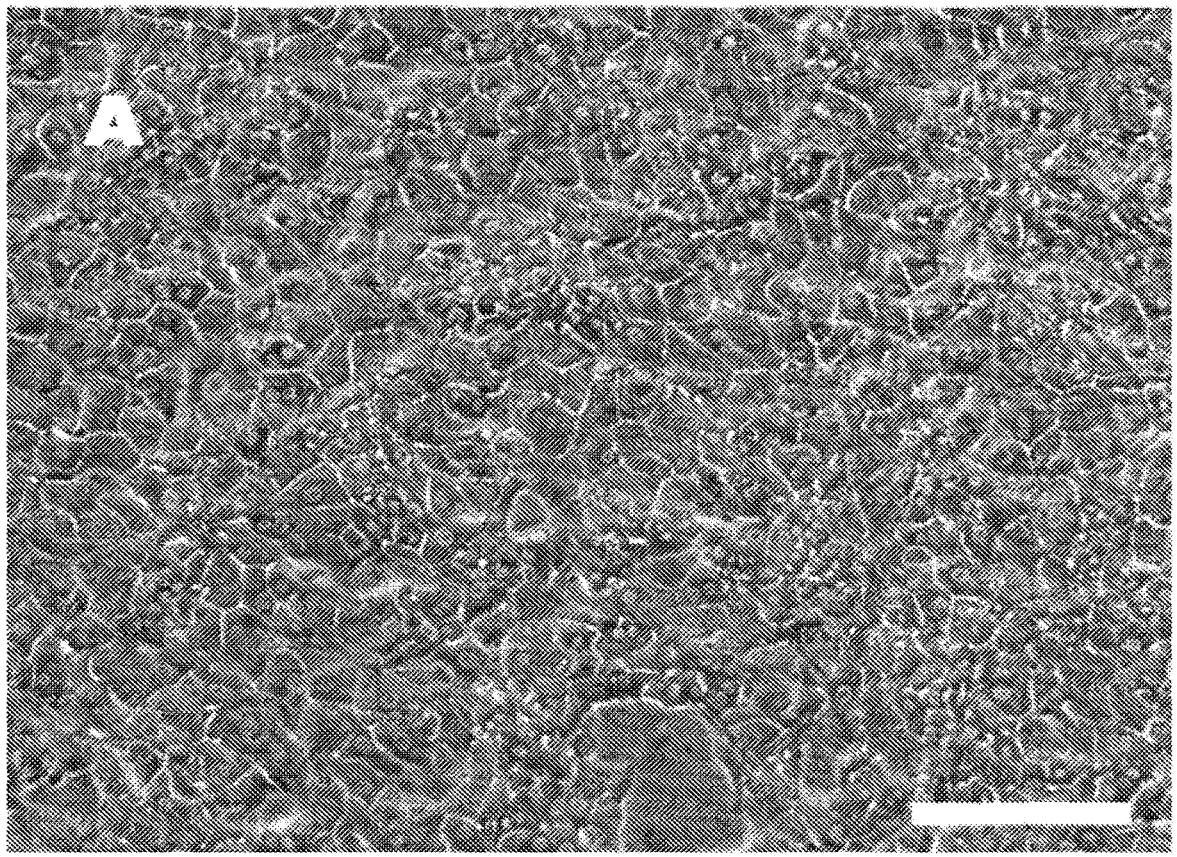
FIGS. 12A-12C depict phase contrast microscopy of cells obtained from ischemic livers after perfusion (FIG. 12A), healthy control livers (FIG. 12B), and one-hour ischemic livers directly isolated (FIG. 12C) in a collagen double gel, respectively, at two weeks post-seeding.
Figure 12B:
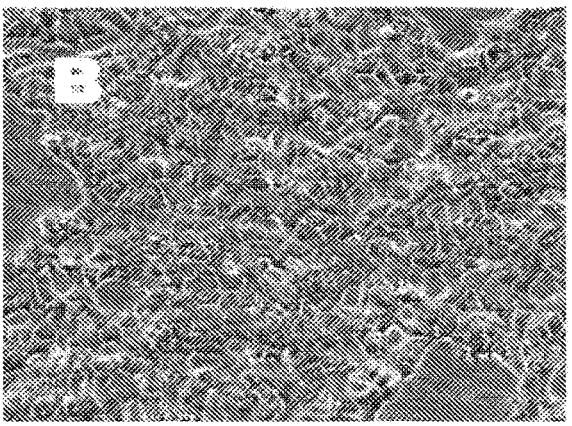
Figure 12C:
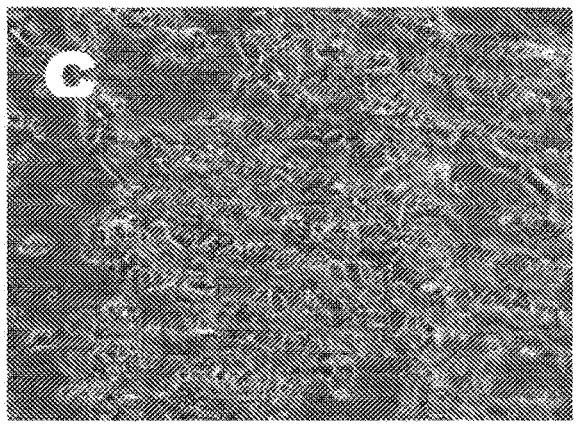
Figure 12D:
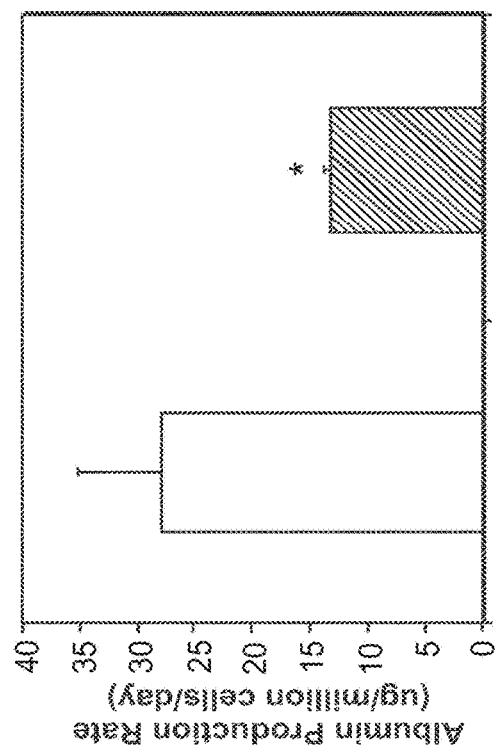
FIG. 12D depicts urea production rates for hepatocytes from perfused ischemic livers compared to fresh livers during six hours of suspension culture.
Figure 12E:
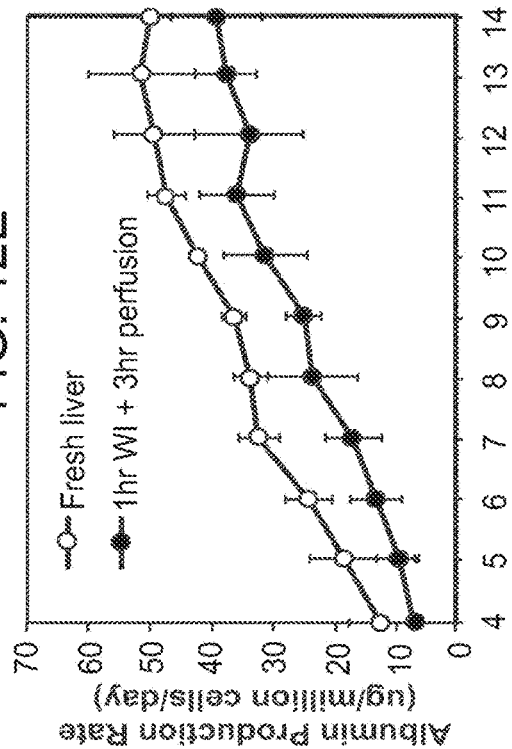
FIG. 12E depicts albumin secretion for hepatocytes from perfused ischemic livers compared to fresh livers during six hours of suspension culture as evaluated with an enzyme-linked immunosorbent assay (ELISA).

Hepatocytes obtained from perfusion-treated livers were compared to cells obtained from fresh rat livers. FIG. 12A depicts phase contrast microscopy of cells Obtained from one-hour ischemic livers after perfusion in a collagen double gel at two weeks post-seeding. Compared to cells obtained from normal (fresh) livers depicted in FIG. 12B, there were no remarkable differences. By comparison, cells obtained from untreated ischemic livers depicted in FIG. 12C did not reach confluency, appeared steatotic and unhealthy, and dedifferentiation was observed. As depicted in FIGS. 12D and 12E, urea synthesis by the hepatocytes from perfusion-treated ischemic cells when cultured in suspension for six hours was similar to those obtained from fresh livers, whereas albumin synthesis was approximately 50% of normal hepatocytes for the duration of the experiment (statistically different at p<0.05).

Figure 12F:
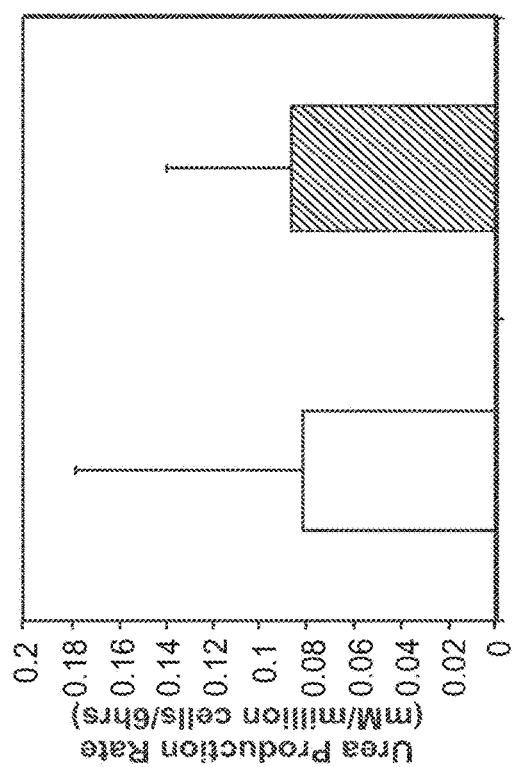
FIG. 12F depicts urea production rates for hepatocytes from perfused ischemic livers compared to fresh livers when cultures in collagen double gel.
Figure 12G:
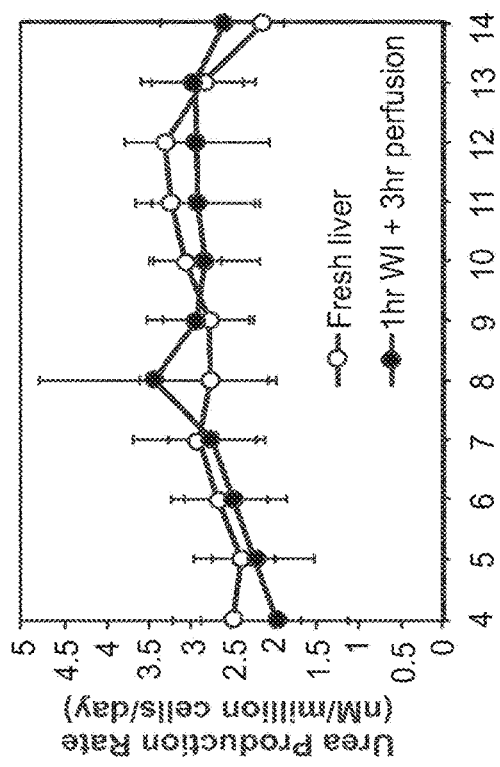
FIG. 12G depicts albumin secretion for hepatocytes from perfused ischemic livers compared to fresh livers when cultured in collagen double gel.

As depicted in FIGS. 12F and 12G, urea and albumin synthesis by the hepatocytes from perfusion-treated ischemic cells when culture in collagen sandwich culture for 14 days was similar to that obtained from fresh livers. There was a slight drop in albumin, but the difference did not reach statistical significance for any day.

These results demonstrate that with the organ perfusion system 100 described herein, the recovery of hepatocytes can be increased significantly and that the recovered hepatocytes are capable of performing essential hepatic functions at a level lower, but still comparable to cells obtained from healthy livers.

WORKING EXAMPLE #3

Decellularization of Ischemic Livers

Figure 13A:
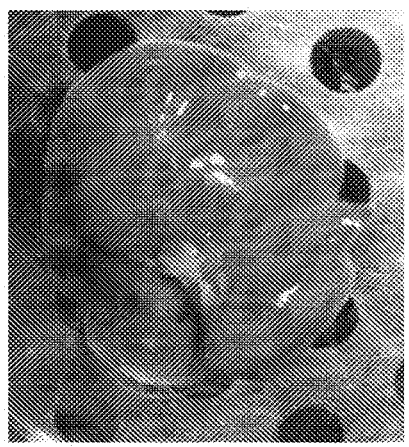
FIGS. 13A-13E are representative photographs of livers during the decellularization process.
Figure 13B:
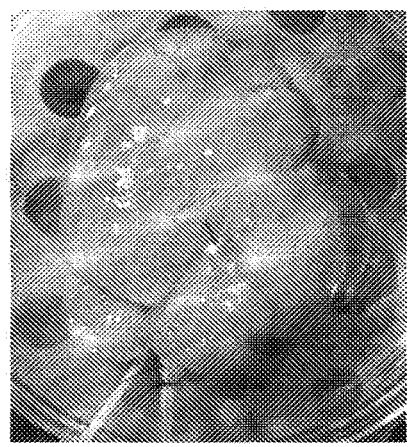
Figure 13C:
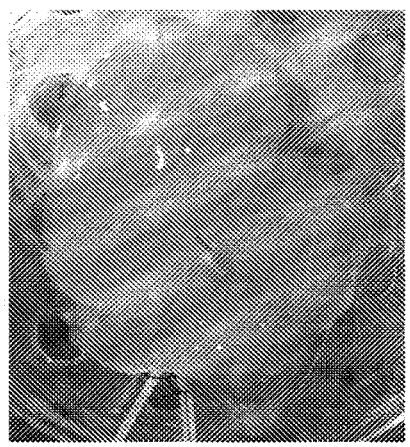
Figure 13D:
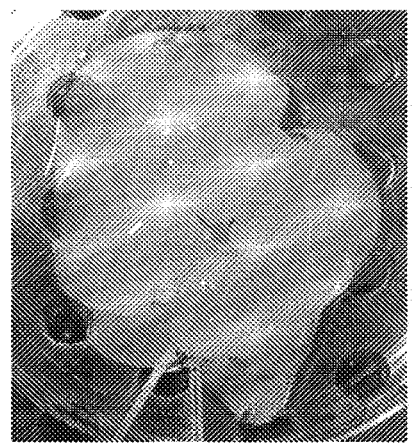
Figure 13E:
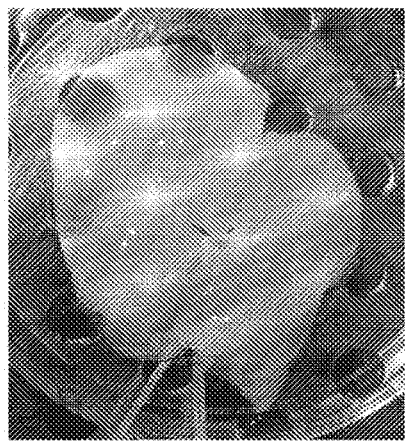

As depicted in FIG. 13A-13E, ischemic rat livers (one hour of warm ischemia at 34° C. in a saline solution) can be decellularized in intact form with the vasculature generally well-preserved. Livers were perfused through the portal vein with 0.1% sodium dodecyl sulfate (SDS) for four hours. FIGS. 13A-13E are representative photographs of livers during the decellularization process. FIG. 13A depicts a liver at t=0 minutes. FIG. 13A depicts a liver at t=25 minutes, FIG. 13C depicts a liver at t=1 hour. FIG. 1317 depicts a liver at t=2 hours. FIG. 13E depicts a liver at t=4 hours. This procedure yielded a fully decellularized construct suitable for use as a bioscaffold for recellularization.

WORKING EXAMPLE #4

Recellularization of Decellularized Livers with Primary Rat Hepatocytes

After storage in an antibiotic solution at 4° C., the decellularized matrices were washed thoroughly and brought to room temperature by perfusion with phosphate buffered saline ("PBS"). After four hours of PBS perfusion, the portal vein of each decellularized liver was cannulated with a sterile 18-gauge cannulae and sutured. The livers were then mounted in the perfusion system and infused with $100 \times 10^6$ isolated rat hepatocytes for over one hour. FIGS. 14A-14D depict representative livers at 0, 10, 20, 30, and 40 minutes post-seeding, respectively.

The recellularized liver native matrices were then cultured for 8 hours under continuous perfusion with oxygenated culture medium. A time period of eight hours was chosen as the initial period of testing because direct cell death due to perfusion damage or poor oxygenation typically kills most cells within two to four hours post-cell-isolation. Thus, eight hours would provide a good indication of the damage induced by the repopulation process. The infused hepatocytes were counted to evaluate cell engraftment immediately after cell seeding and it was found that around 70% of the seeded cells remained in the livers and engrafted around the vessels with most hepatocytes in the parenchyma.

To assess viability, recellularized livers were stained for glycogen and the majority of the cells were positive for PAS (Periodic Acid Schiff, staining demonstrating that infused hepatocytes were viable and active in the short term following recellularization. FIG. 15A depicts a hematoxylin and eosin (H&E) stained decellularized liver matrix. FIG. 15B depicts an H&E-stained recellularized liver matrix. FIG. 15C depicts a PAS-stained recellularized liver matrix. It was also notable that the vascular structure seemed to be preserved.

To further assess the success of reseeding, apoptosis in the seeded cells was evaluated via TUNEL (terminal deoxynucleotidyl transferase dUTP nick end labeling) staining after eight hours of perfusion. FIG. 16A depicts a negative control of TUNEL staining without antibody. In FIG. 16B, apoptotic cells stained in green. FIG. 16C depicts positive control of TUNEL staining of a DNAse exposed liver sample. DAPI (4', 6-diamidino-2-phenylindole) staining is depicted in the lower left corner of FIGS. 16A-16C. Less than 20% cells were positive for apoptosis. Stable oxygen uptake rates were also observed during this period.

Figure 17A:
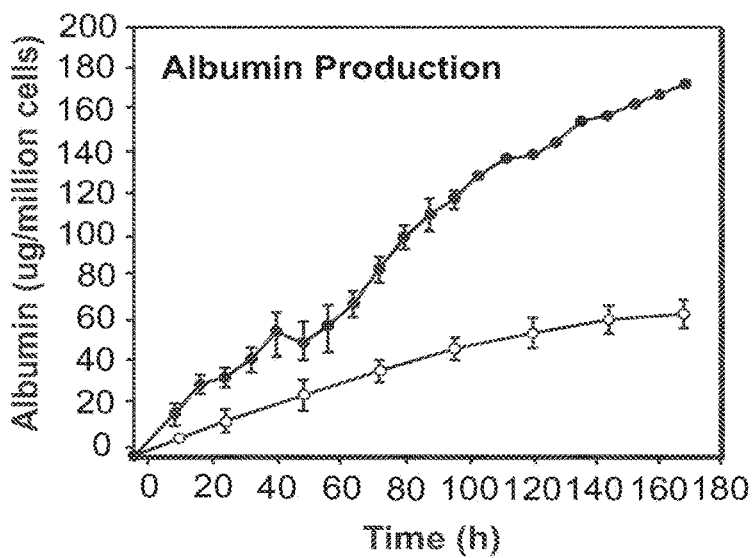
FIG. 17A-17C depict albumin, urea, and lactate dehydrogenase levels for recellularized livers compared to hepatocytes in collagen culture.
Figure 17B:
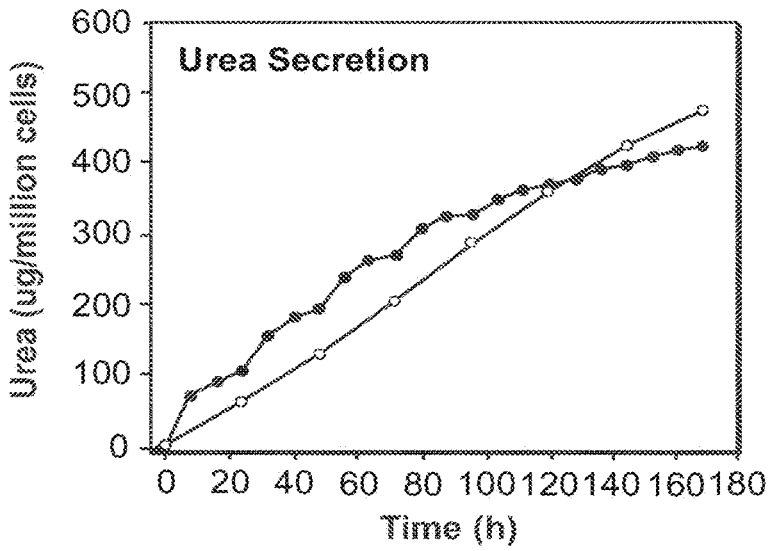
Figure 17C:
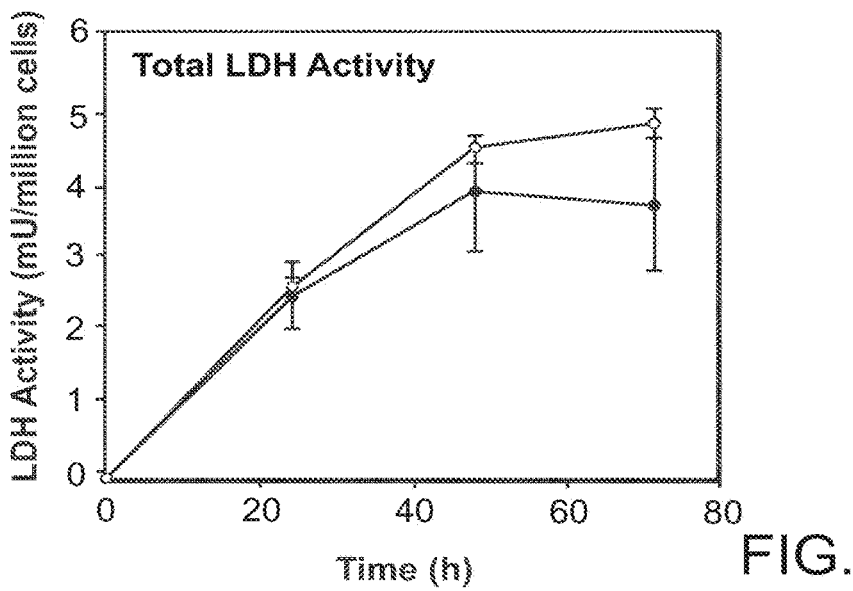

To assess viability after repopulation, recellularized livers were perfusion-cultured for seven days. As depicted in FIGS. 17A and 17B, there was steady production of albumin (measured by ELISA) and urea (measured with a BUN assay kit) proving hepatic functionality in the recellularized liver. As depicted in FIG. 17B, extracellular lactate dehydrogenase levels (measured with an LDH kit) during first 80 hours of perfusion are identical to cell culture levels, indicating no significant damage to the cells in the system. In FIGS. 17A-17C, data for liver grafts repopulated with primary rat hepatocytes are represented with closed circles, while data for collagen sandwiched cultured primary rat hepatocytes are represented with open circles.

Figures 18A, 18B, 18C:
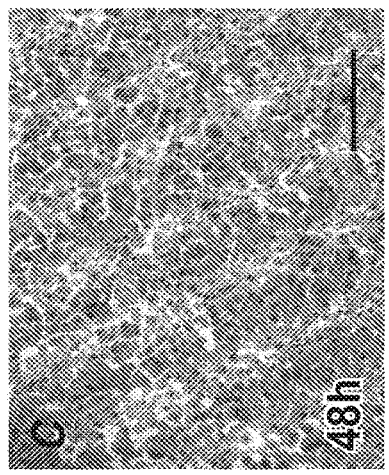
FIGS. 18A-18F are representative photographs of H&E-stained liver matrices.
Figures 18D, 18E, 18F:
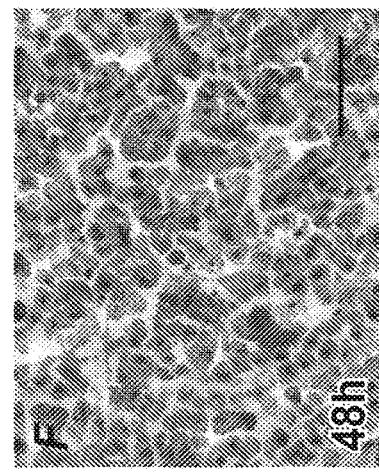

In addition, hepatocytes demonstrated the ability to home to and engraft in the liver matrix and around the vessels as depicted by FIGS. 18A-18F, which are photographs of H&E-stained liver matrices. FIGS. 18A and 18D depict an H&E-stained normal liver matrix at 20× and 40× power, respectively. FIGS. 18B and 18E depict an H&E-stained repopulated liver matrix at 20× and 40× power, respectively, after 24 hours of perfusion culturing. FIGS. 18C and 18F depict an ME-stained repopulated liver matrix at 20× and 40× power, respectively, after 48 hours of perfusion culturing. The cells were well distributed and healthy after 48 hours, with polygonal shaped cells containing multiple nuclei present. These results demonstrate that hepatocytes can be seeded in the recellularized grafts and the hepatocyte function can be maintained up to a week.

WORKING EXAMPLE #5

In Vivo Transplantation of Decellularized Liver Graft

Figure 19B:
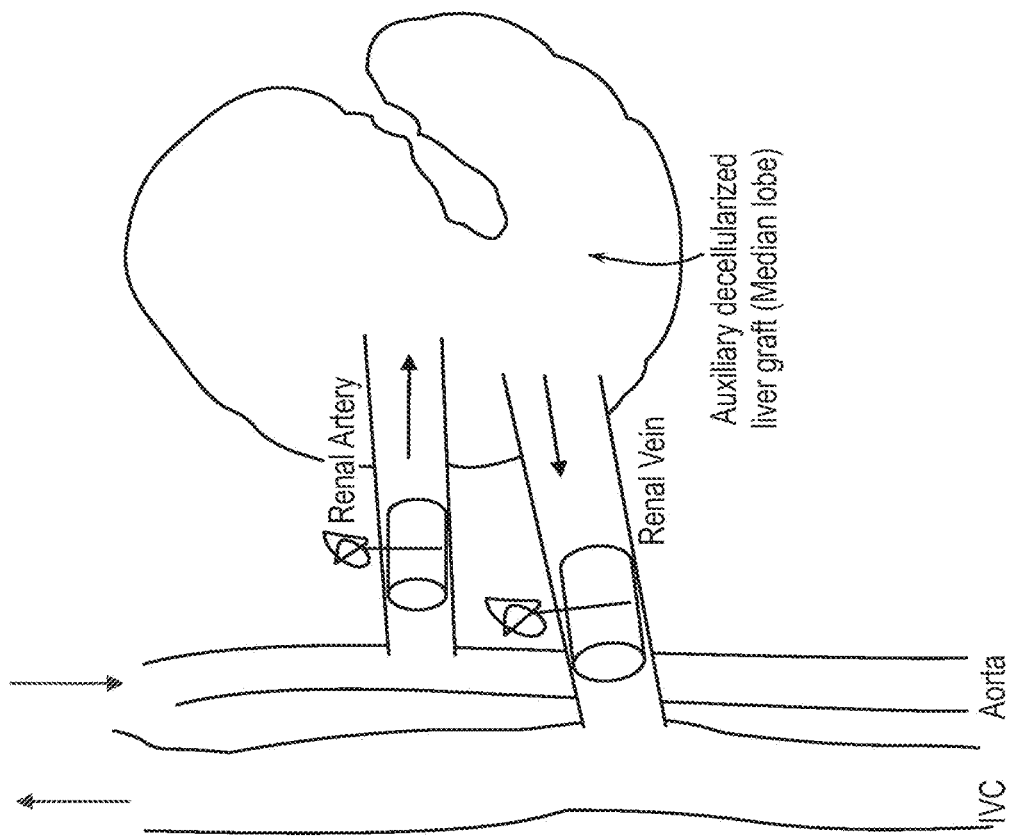
FIG. 19B is a schematic of a transplanted recellularized liver.
Figure 19A:
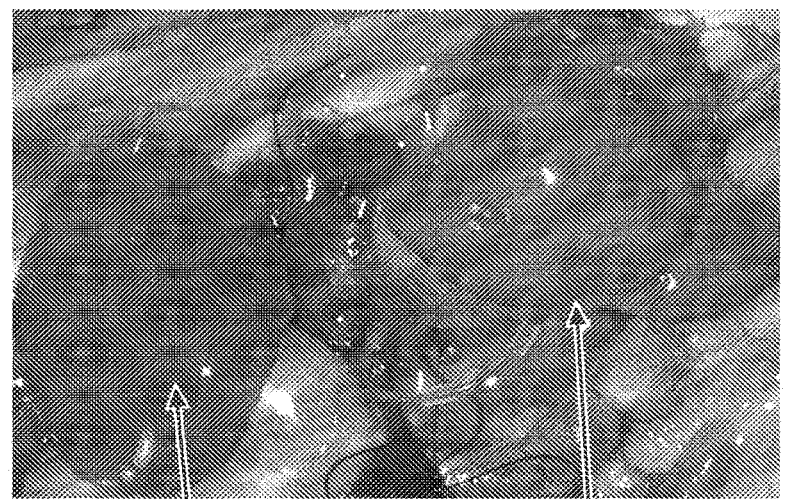
FIG. 19A is a photograph of a transplanted liver bioscaffold.
Figure 20C:
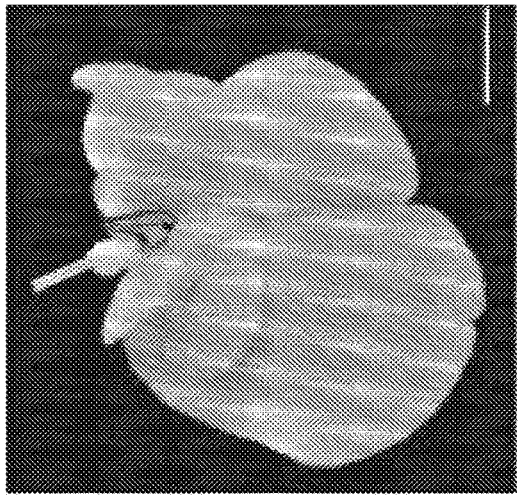
FIGS. 20A-20E are representative photographs of ischemic rat livers during a decellularization process at 0 hours, 18 hours, 48 hours, 52 hours, and 72 hours, respectively. The scale bars represent 10 mm.
Figure 20B:
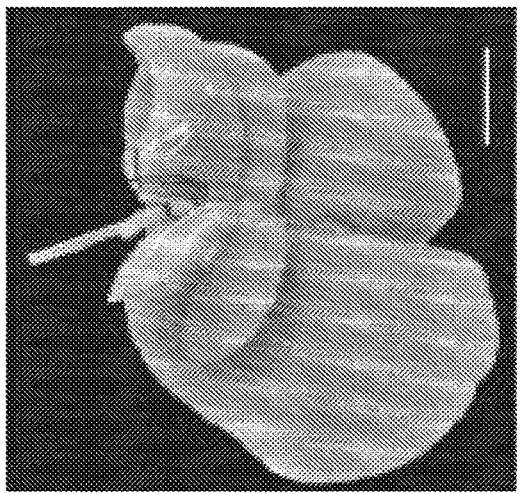
Figure 20E:
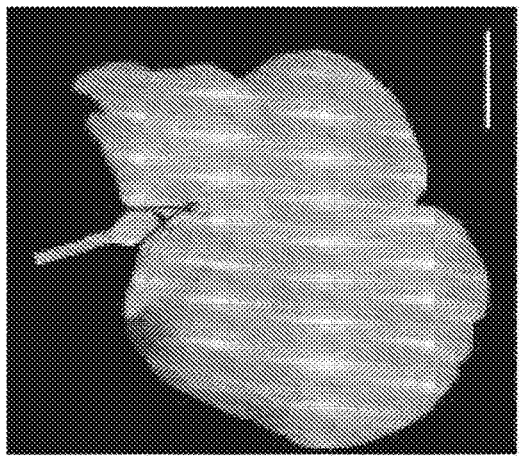
Figure 20A:
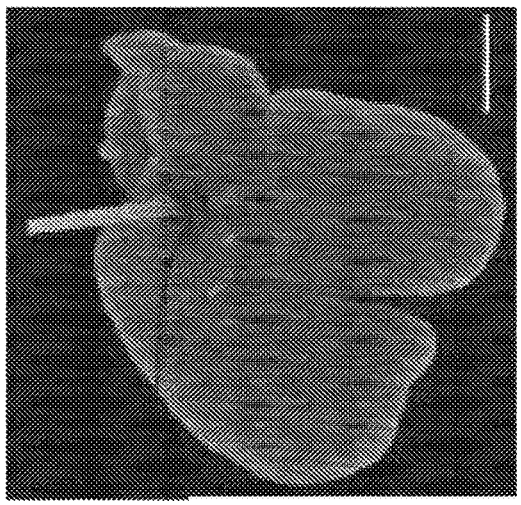
Figure 20D:
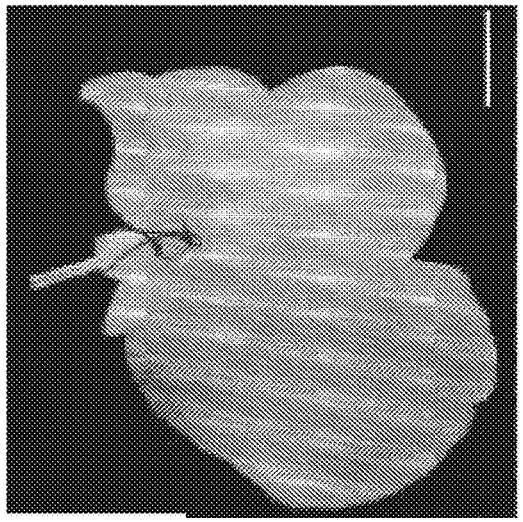

As depicted in FIGS. 19A and 19B, the decellularized grafts were transplanted to test whether the liver extracellular matrix (ECM) was capable of handling the pressure and viscosity of blood flow. The decellularized liver was subjected to resection of the right superior lobe, right inferior lobe, left lateral lobe, and the inferior and superior caudate lobes with piercing sutures to avoid damage to the stump and paracaval circulation circuit. The hepatic artery, superior vena cava (SVC), and bile duct were closed. After a left nephrectomy, the decellularized liver graft, which was reduced to about 30% of the original size, was implanted into the left upper quadrant of the recipient's abdomen. The inferior vena cava (IVC) was anastomosed by a stent technique. The donor's portal vein was completely arterialized to the recipient's left renal artery in a stent technique. Using a stent with an internal diameter of 0.3 mm, the flow in the arterialized portal vein was regulated to achieve physiologic parameters.

Overall, the decellularized graft was well perfused, able to sustain the flow, and no occlusion of blood circulation was observed in the bioscaffold.

WORKING EXAMPLE #6

Characterization of Decellularized Liver Matrix (DLM)

Figure 21:
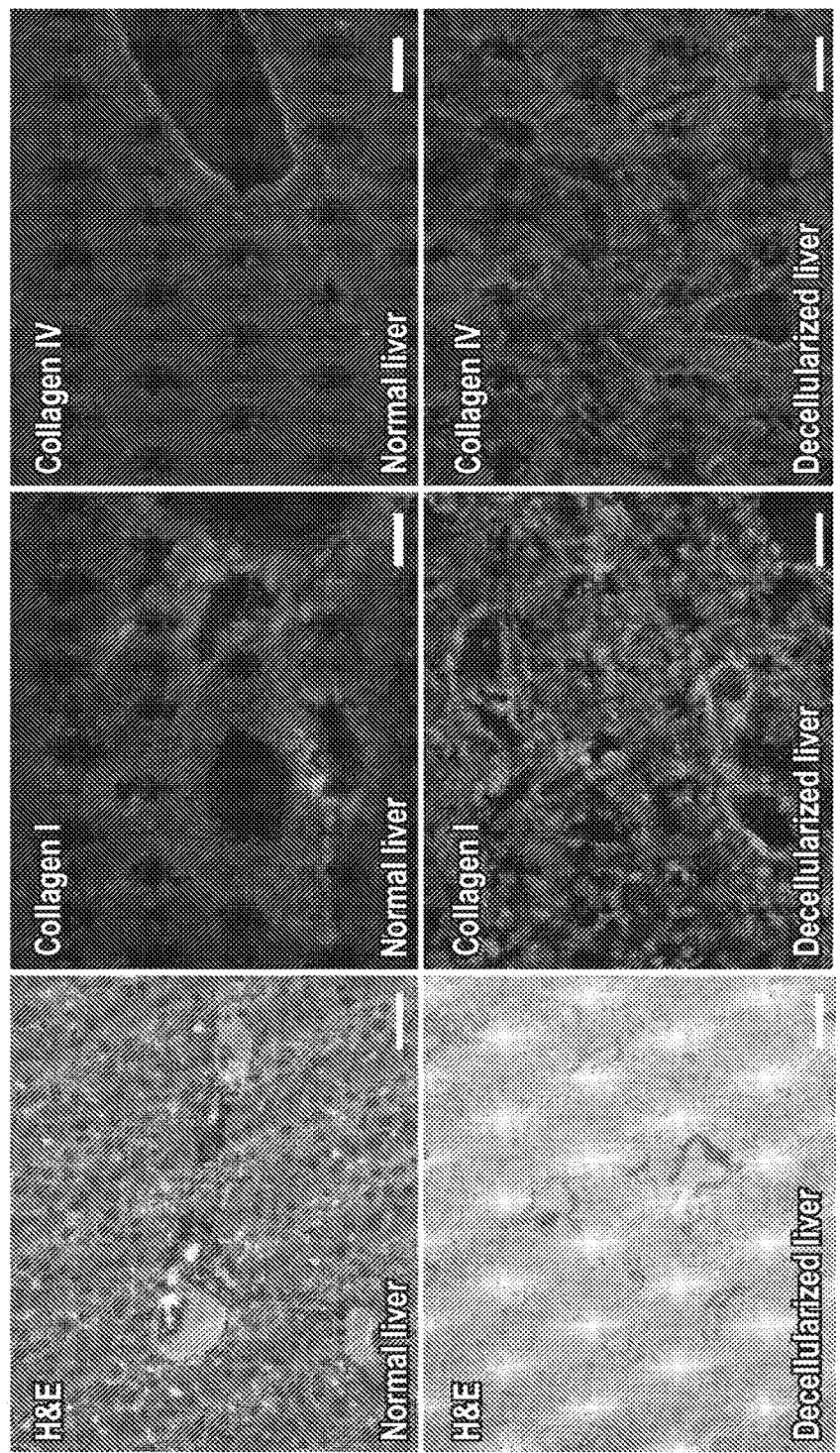
FIG. 21 is a comparison of a normal liver (top row) and a decellularized liver matrix (bottom row) produced through staining for (from left to right across each row) hematoxylin and eosin, collagen I (red), collagen IV (red), fibronectin (red), and lamin (red). Sections were counterstained with DAPI (blue). The scale bars represented 100 µm.
Figure 21:
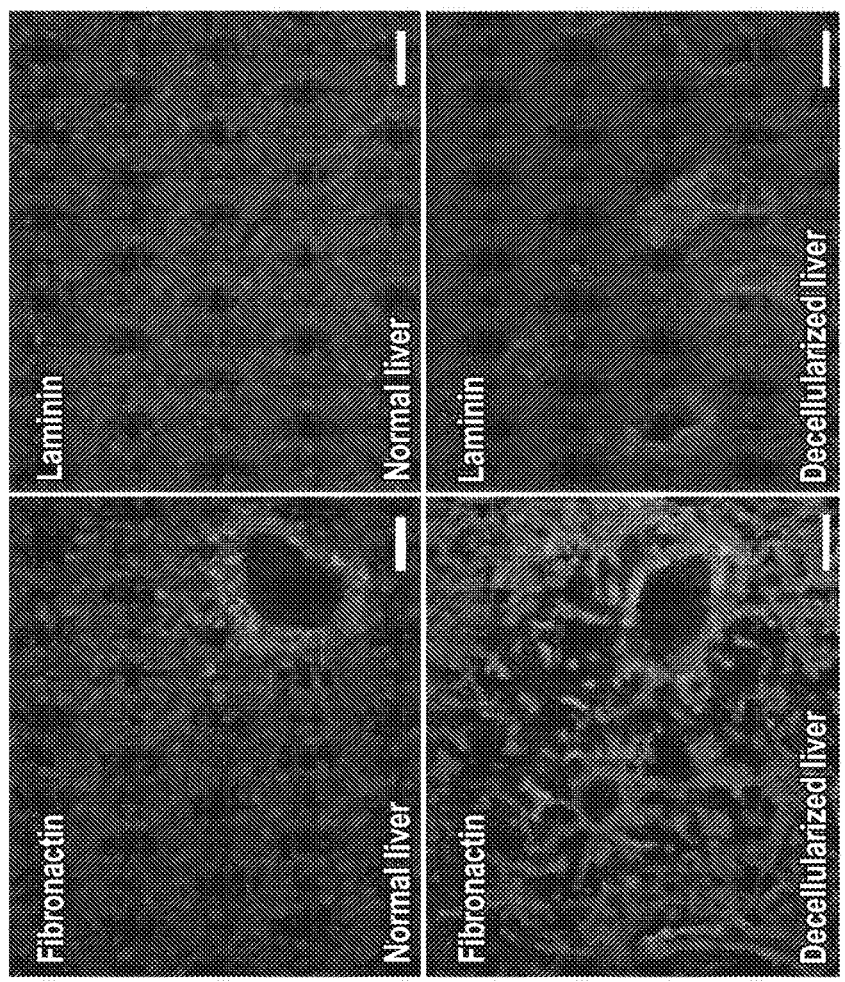

Whole organ decellularization was achieved by portal perfusion with sodium dodecyl sulfate (SDS), an anionic detergent that lyses cells and solubilizes cytoplasmic components. Following 72 hours of decellularization, a translucent acellular scaffold, which retained the gross shape of liver, was generated as depicted in FIGS. 20A-20E. Histological evaluation revealed no nuclei or cytoplasmic staining in the DLM compared to normal rat liver as depicted in the leftmost segments of FIG. 21. Immunostaining for extracellular matrix (ECM) proteins, collagen type I, collagen type IV, fibronectin and laminin-β1, indicated that both structural and basement membrane components of the ECM were retained similarly to native liver as depicted in the remaining panes of FIG. 21. The lack of DAPI staining in DLM confirms the absence of cells. Both collagen type IV and fibronectin were observed in decellularized sinusoidal spaces, while laminin-β1 is seen in the basement membrane of the larger vessels. 100% of the fibrillar collagen and approximately 50% of the glycosarninoglycans of native liver were retained following decellularization. Residual DNA content in the DLM was less than 3%.

Figure 22B:
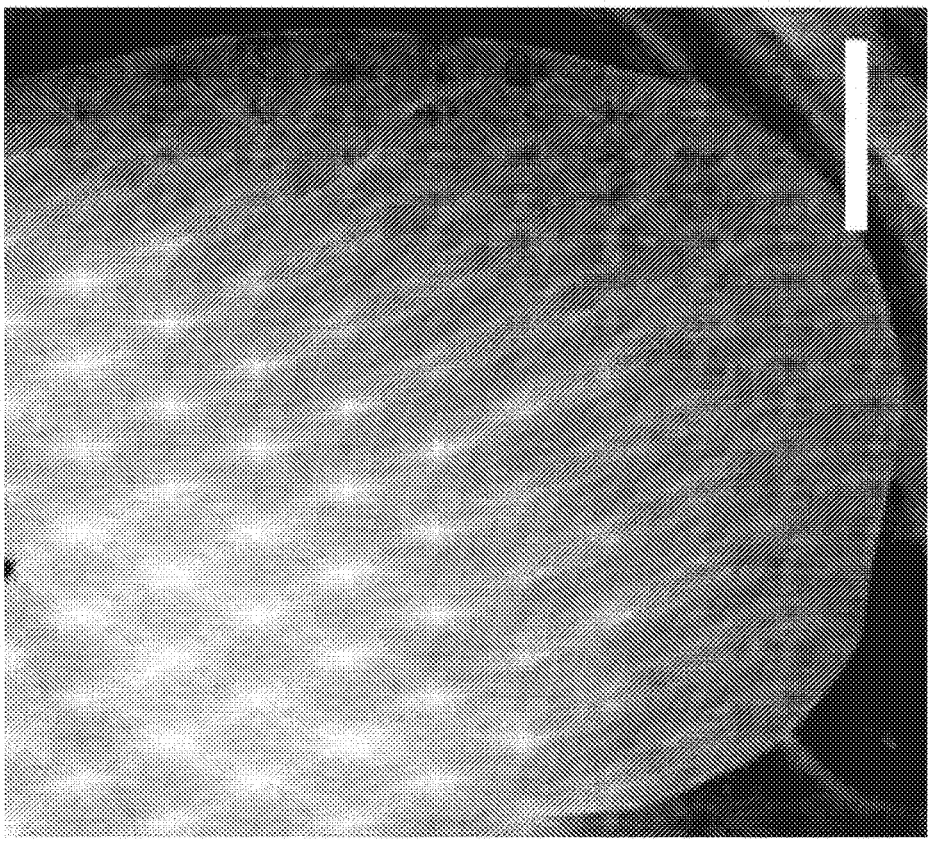
FIGS. 22A and 22B are representative photographs of decellularized left lateral and median lobes of a decellularized liver matrix with the vascular tree visible.
Figure 22A:
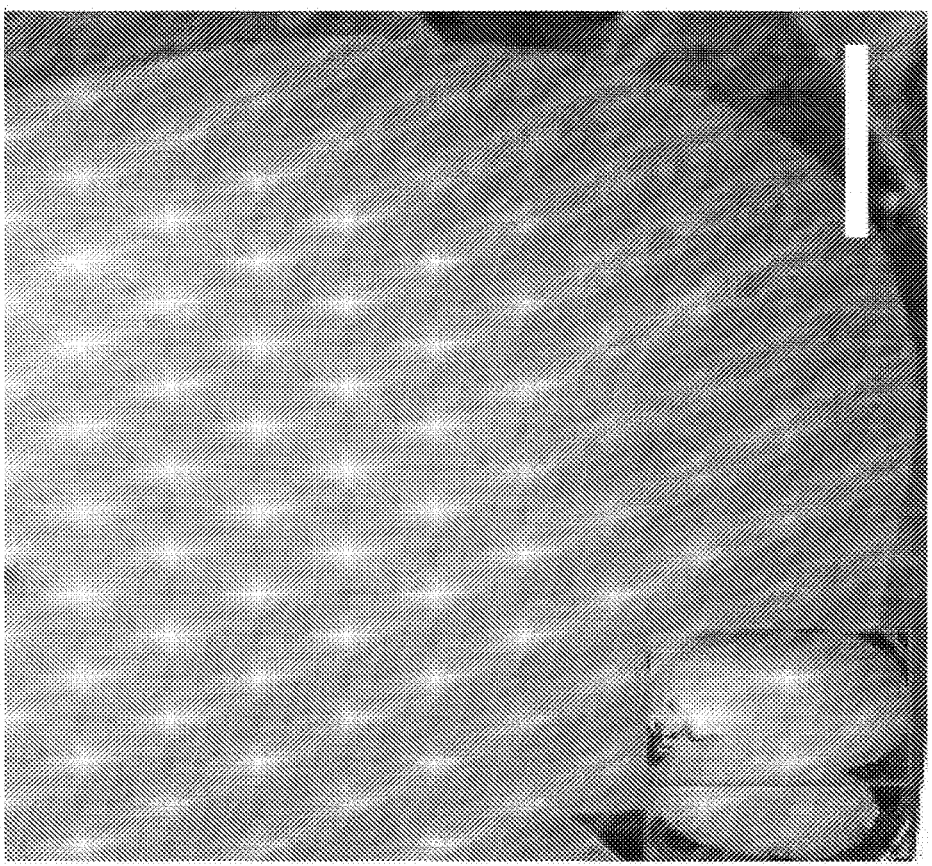

To demonstrate that decellularization protocol was successful in retaining a functional vascular bed, its perfusion was characterized using Allura Red dye. Structural components of the vascular tree were clearly apparent in the translucent matrix as depicted in FIGS. 22A and 22B. The dye injected through the portal vein flowed as would be expected inside the vascular network, gradually moving from larger vessels to smaller capillaries, suggesting the microvasculature remained intact.

Figure 23B:
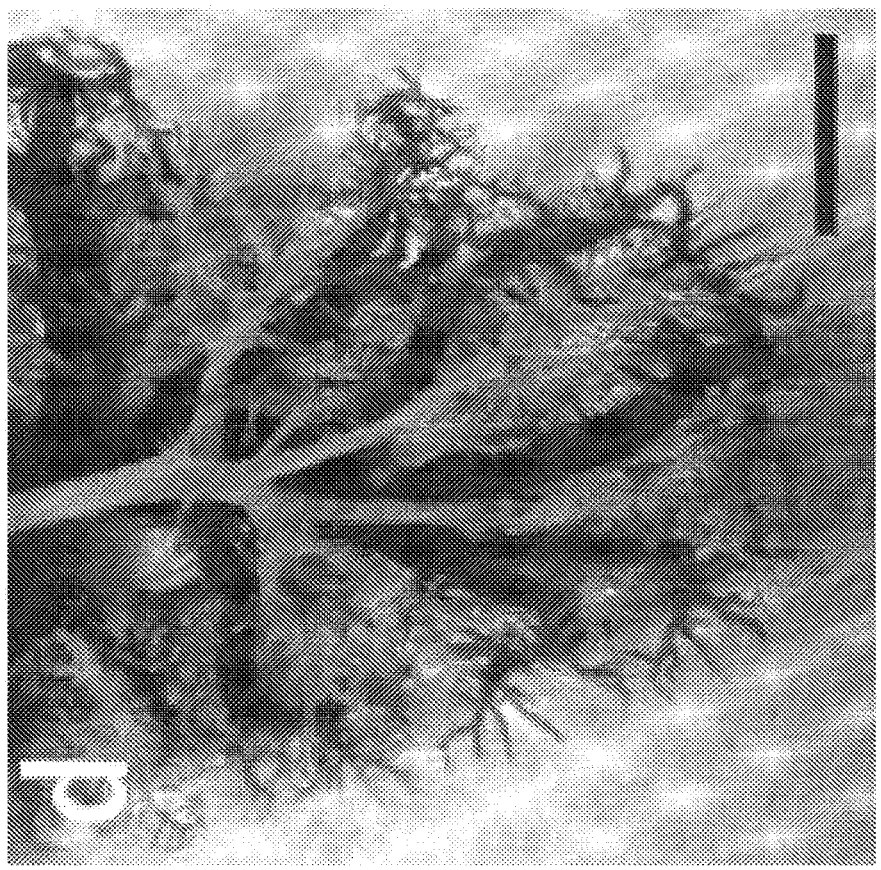
FIGS. 23A and 23B are representative photographs of corrosion cast models the vascular tree of a normal liver (FIG. 23A) and a decellularized liver matrix (FIG. 23B) with portal (red) and venous (blue) vasculature.
Figure 23A:
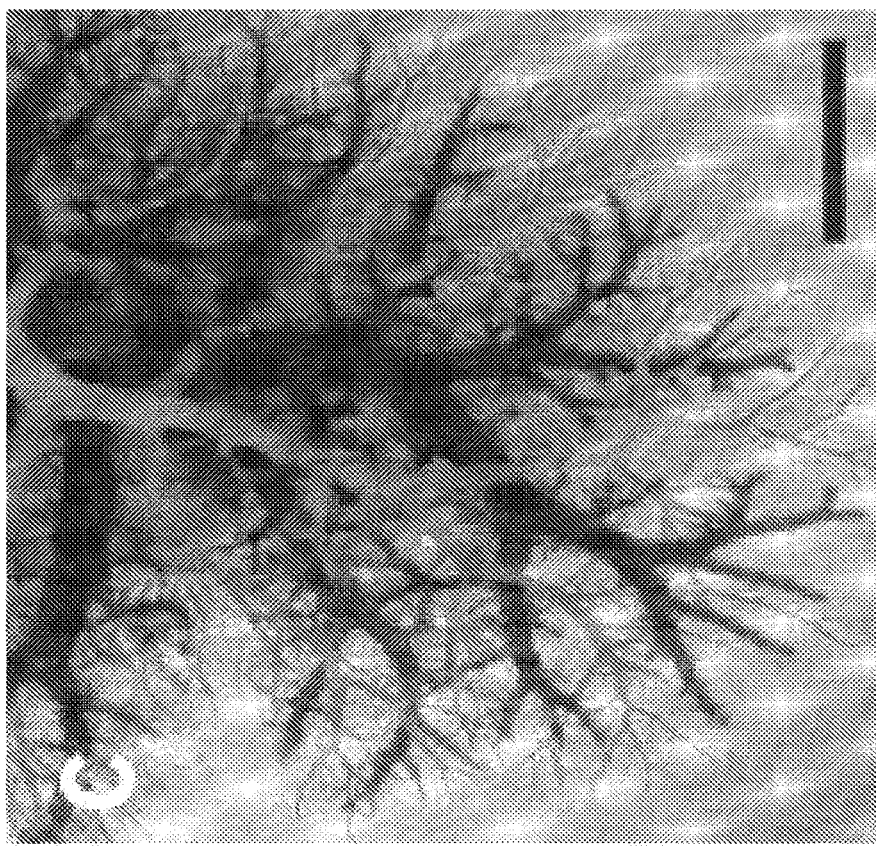

The intricate vascular tree was further characterized by generating a corrosion cast of the DLM as depicted in FIGS. 23A and B. Portal (red) and venous (blue) vasculature casting of both normal (FIG. 23A) and decellularized (FIG. 23B) livers showed that the larger portal and venous circulation system of vessels and the vast majority of the smaller microcirculatory branches were preserved, indicating that physiologic flow could be achieved by traversing the portal venous system and emptying into the systemic venous circulation via the hepatic vein and inferior vena cava (IVC).

Figure 24A:
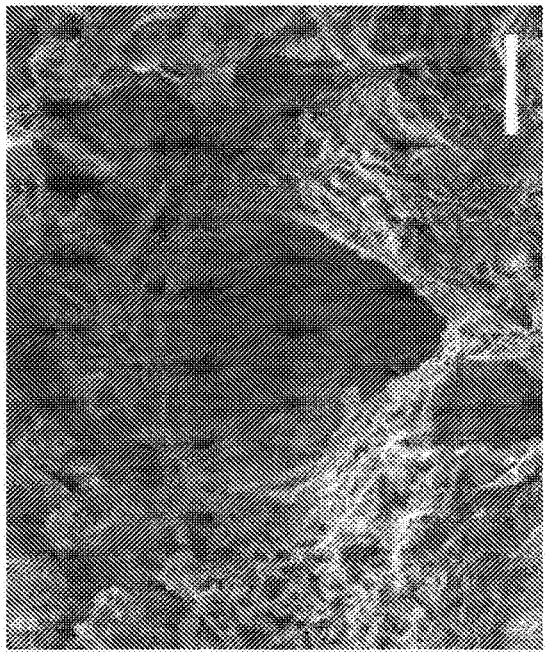
FIGS. 24A-C are scanning electron microscopy (SEM) micrographs of a decellularized liver matrix.
Figure 24B:
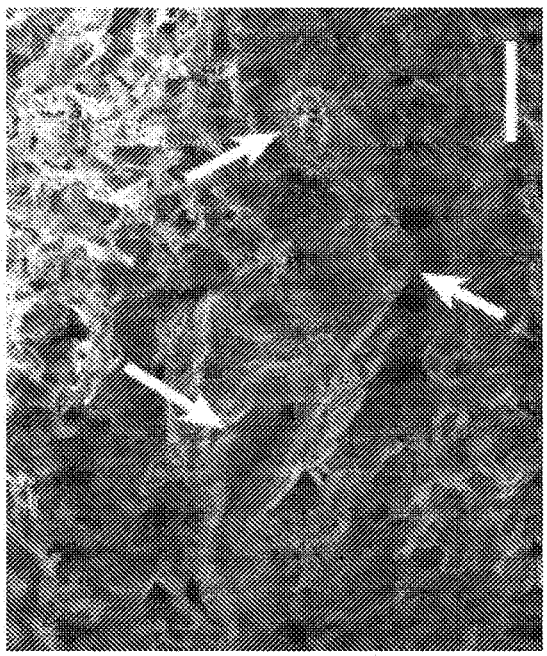
Figure 24C:
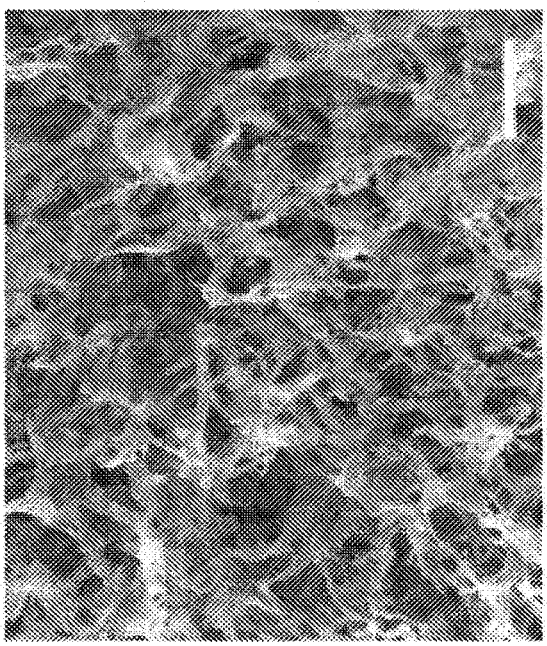

Moreover, scanning electron microscopy (SEM) images confirmed the presence of large vessels within the DLM as depicted in FIG. 24A. Remnants of small vessels closely resembling a portal triad were also observed as depicted in FIG. 24B. The honeycomb of about 30-μm diameter gaps in the ECM depicted in FIG. 24C is thought to be the footprint of hepatocytes removed during decellularization.

WORKING EXAMPLE #7

Recellularization of a Decellularized Liver Matrix

Presence of a functional vascular bed in the DLM offers the ability to control hepatocyte engraftment and characterize liver-specific metabolic function in vitro prior to transplantation of the recellularized graft. Primary rat hepatocytes were introduced via portal vein perfusion recirculation.

Figure 25:
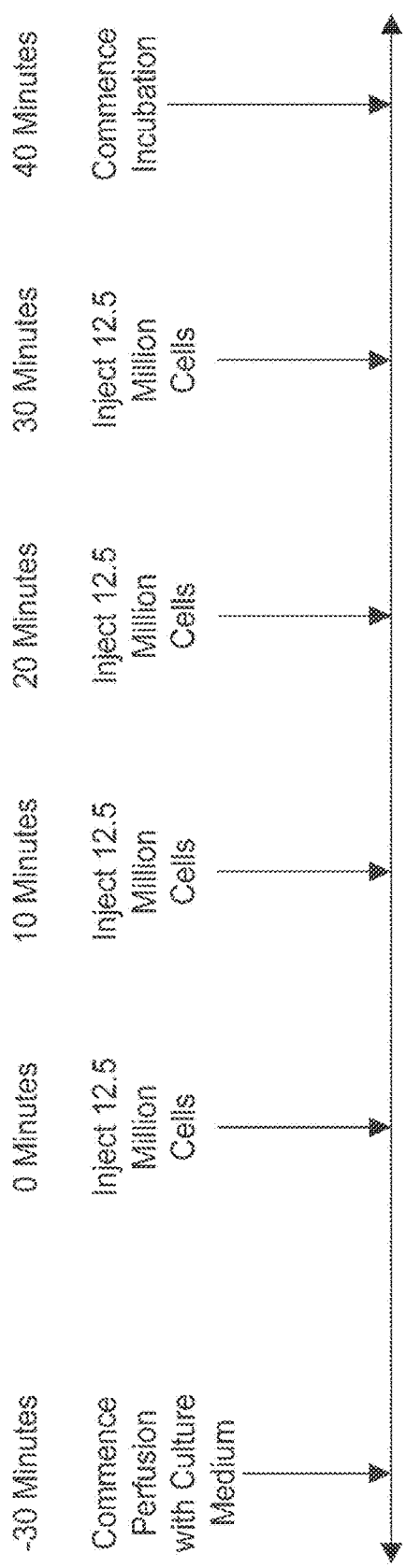
FIG. 25 depicts an exemplary method of recellularizing a decellularized organ (e.g., a decellularized liver matrix).

As depicted in FIG. 25, roughly 12.5 million cells were introduced at each step, for a total of four steps, with 10 minute intervals between each step. Cell viability and distribution in the parenchyma using this four-step seeding protocol was superior to single step infusion of 50 million cells for 40 min. Engraftment efficiency using the four-step protocol was 95.6±3.4%.

Figure 26:
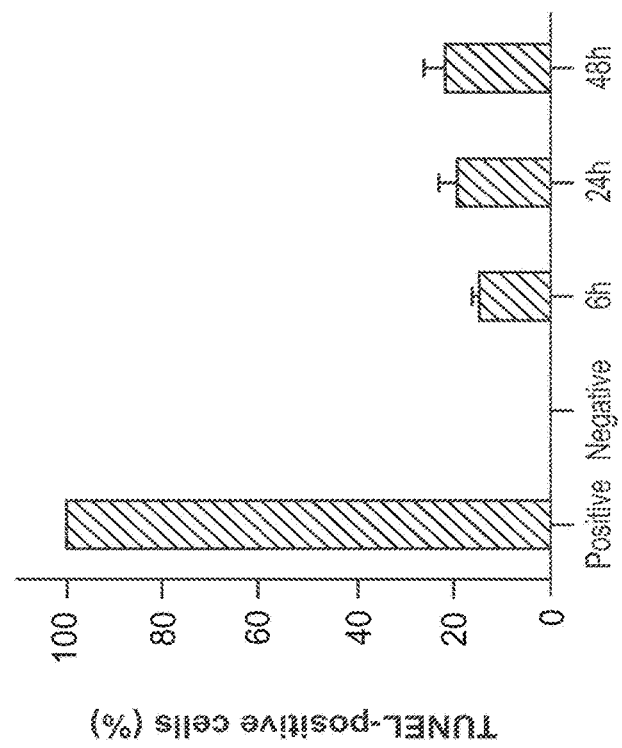
FIG. 26 is bar graph depicting the percentage of TUNEL-positive cells in recellularized liver grafts as a function of perfusion-culture time.
Figure 27:
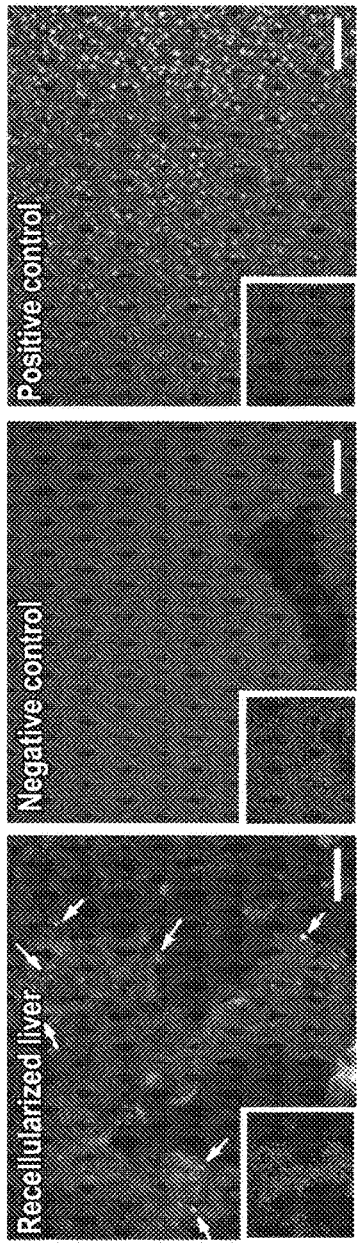
FIG. 27 provides three images of TUNEL-stained recellularized liver grafts. The left photograph depicts a recellularized graft after 48 hours in culture. The center photograph depicts a freshly isolated liver, which was used as a negative control. The right photograph depicts a DNAse-treated normal live, which was used as a positive control. Arrows indicate TUNEL-positive cells. Each photograph contains an inset photograph depicting a Hoeschst 33258 counterstain of the respective sections. The scale bar in each of the large photographs represents 200 µm.
Figure 28:
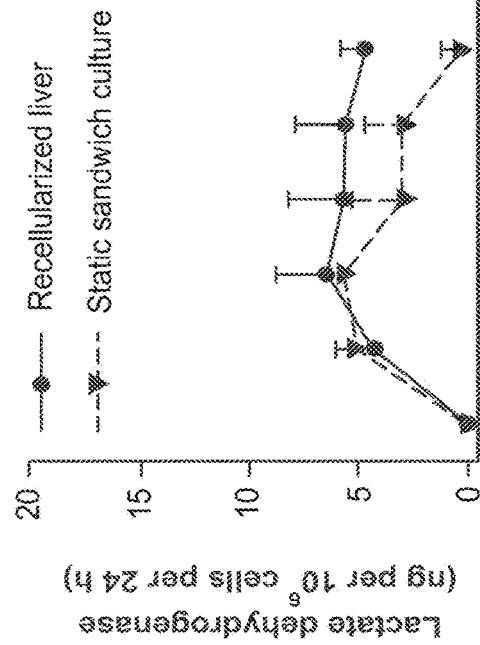
FIG. 28 is a line graph of lactate dehydrogenase release from recellularized liver grafts during perfusion culture as compared with a static sandwich culture.
Figure 29A:
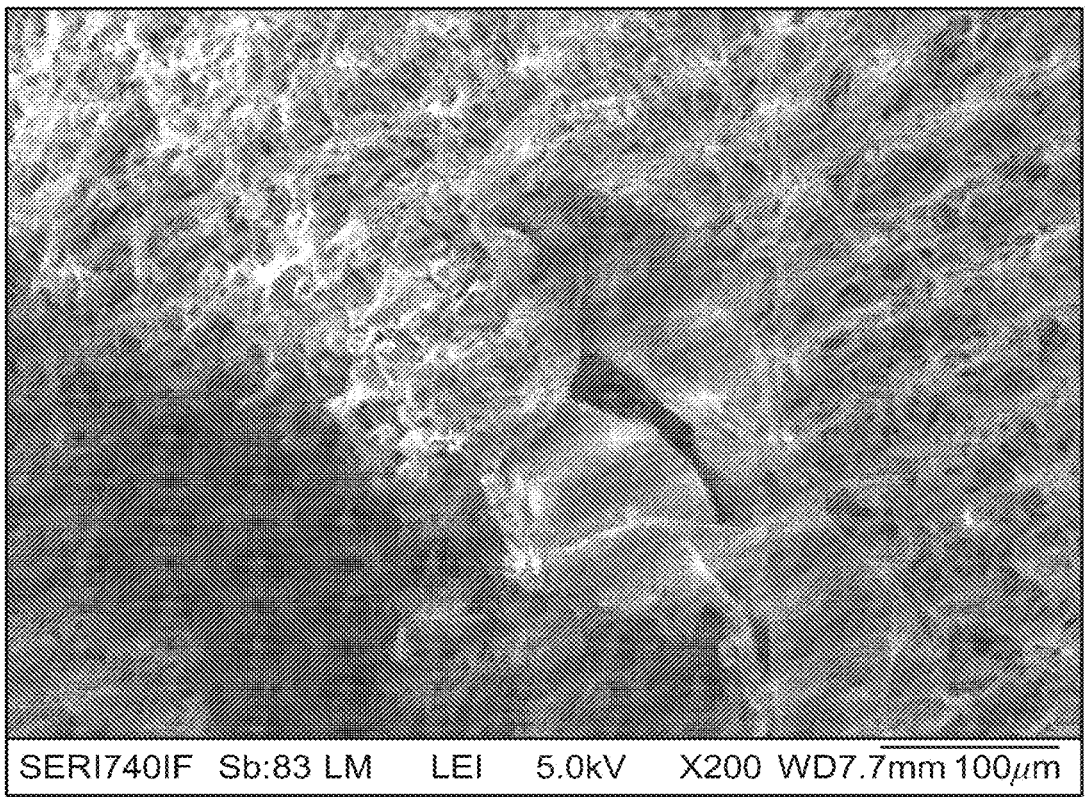
FIGS. 29A and 29B are SEM micrographs of recellularized liver grafts after two days in culture.
Figure 29B:
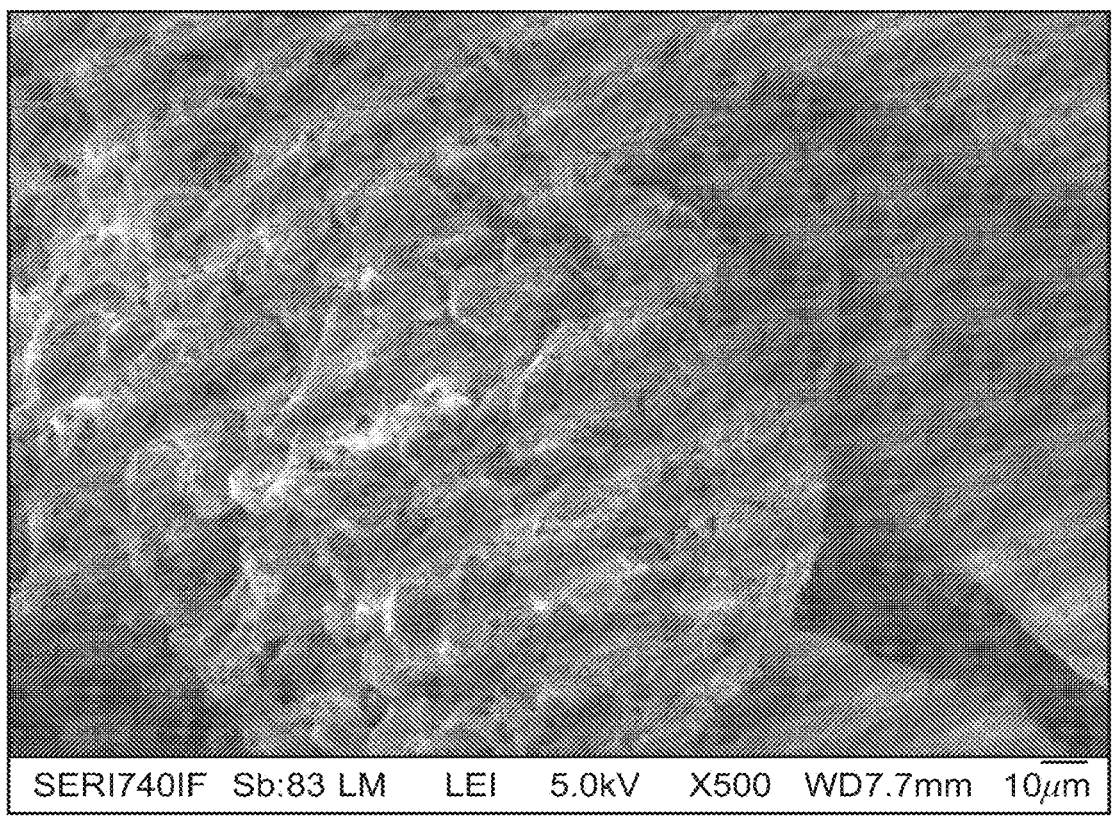
Figure 30:
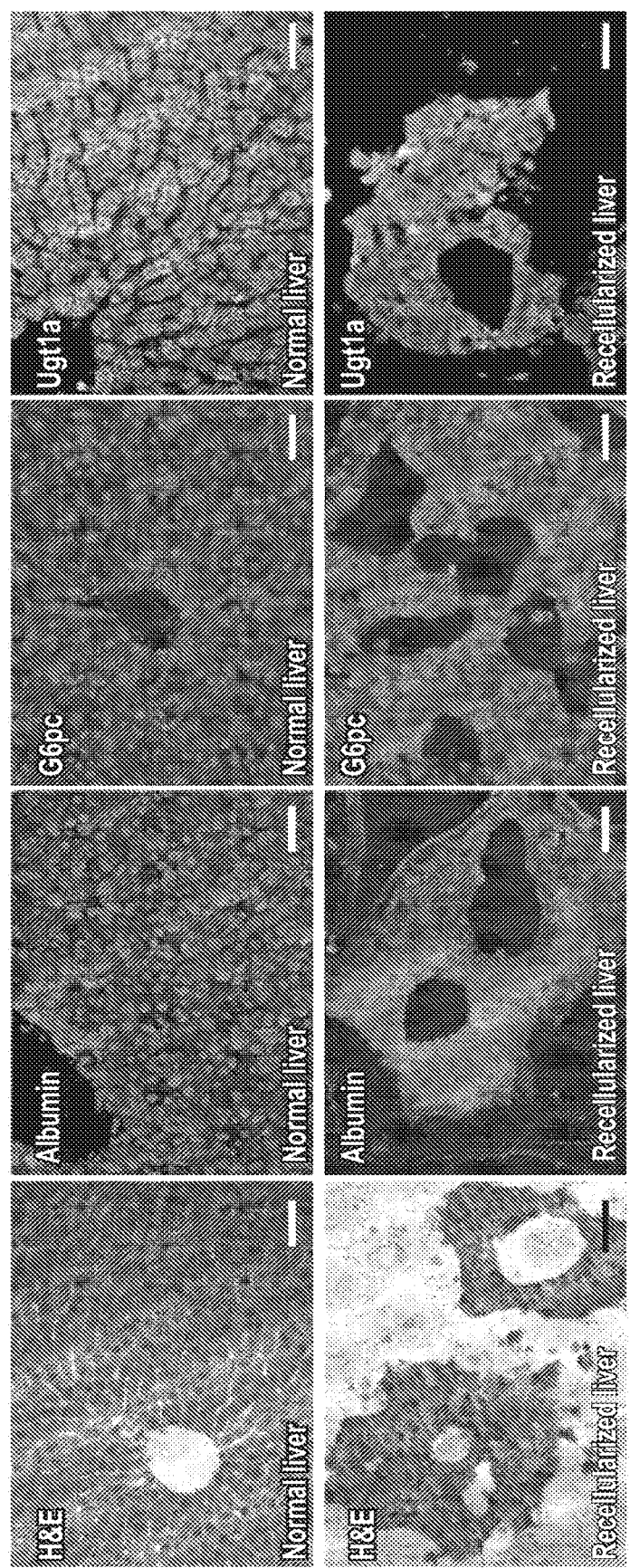
FIG. 30 is a comparison of a normal liver (top row) and a recellularized liver graft (bottom row) produced through immunostaining after two days of culture for (front left to right across each row) hematoxylin and eosin, albumin (red), G6pc (red), and Ugt1a (green). The scale bars represent 100 µm.

Following seeding, the recellularized liver grafts were transferred into a specially-designed perfusion chamber as depicted in FIG. 2B for in vitro culture. The perfusion chamber features two hermetically-sealed silicon sheets, forming a pouch filled with culture medium. This design avoids rigid surfaces, thereby preventing development of pressure spots, while enabling sterile culture of the recellularized grafts up to two weeks in vitro. Histological staining of recellularized sections at 4 hours and at 1 day, 2 days and 5 days revealed that at 4 hours, a majority of the cells remain in and around the vessels, whereas at 1 day and 2 days, the cells leave the vessels and are distributed throughout the matrix. No changes in the distribution of the cells were observed within the matrix at 5 days, as compared to previous days The recellularized liver graft was continuously perfused for 5 days. Hepatocyte viability was maintained during culture. As depicted in FIG. 26, quantification of TUNEL-positive cells (depicted in FIG. 27) revealed that less than 20% of the cells were apoptotic on the first 2 days of culture. LDH release during perfusion was comparable and statistically not different between groups indicating minimal cell death (p=0.0455) as depicted in FIG. 28. SEM and histological analysis depicted in FIG. 29 demonstrated that hepatocytes engrafted around the larger vessels, populating the surrounding parenchyma and suggesting that the cells migrated beyond the matrix barrier to reach decellularized sinusoidal spaces. Functional characteristics of engrafted hepatocytes in the decellularized matrix were assessed via immunostaining at 2 days of culture using Ugt1a (a sensitive enzyme with a short half-life (about 50 min) whose presence demonstrates hepatocyte viability and function), G6pc, and albumin as depicted in FIG. 30. The level of immunostaining for these markers in engrafted hepatocytes was similar to normal livers.

Figure 31A:
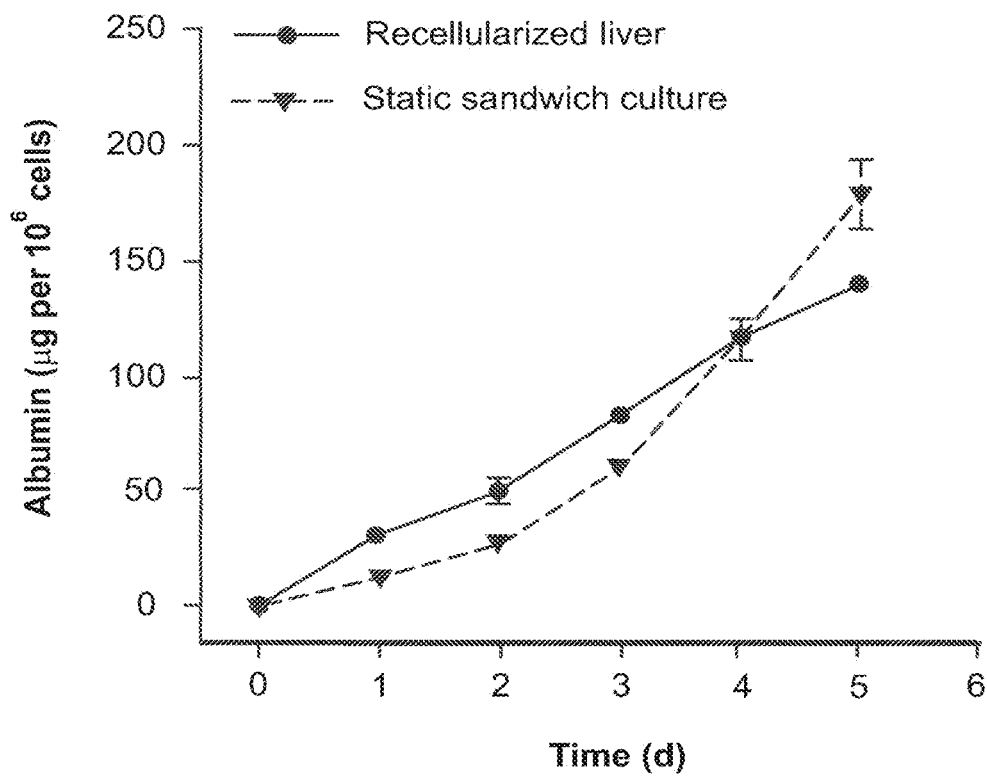
FIGS. 31A and 31B are line graphs depicting albumin synthesis and urea secretion, respectively, for recellularized liver grafts in comparison with a static sandwich culture.
Figure 31B:
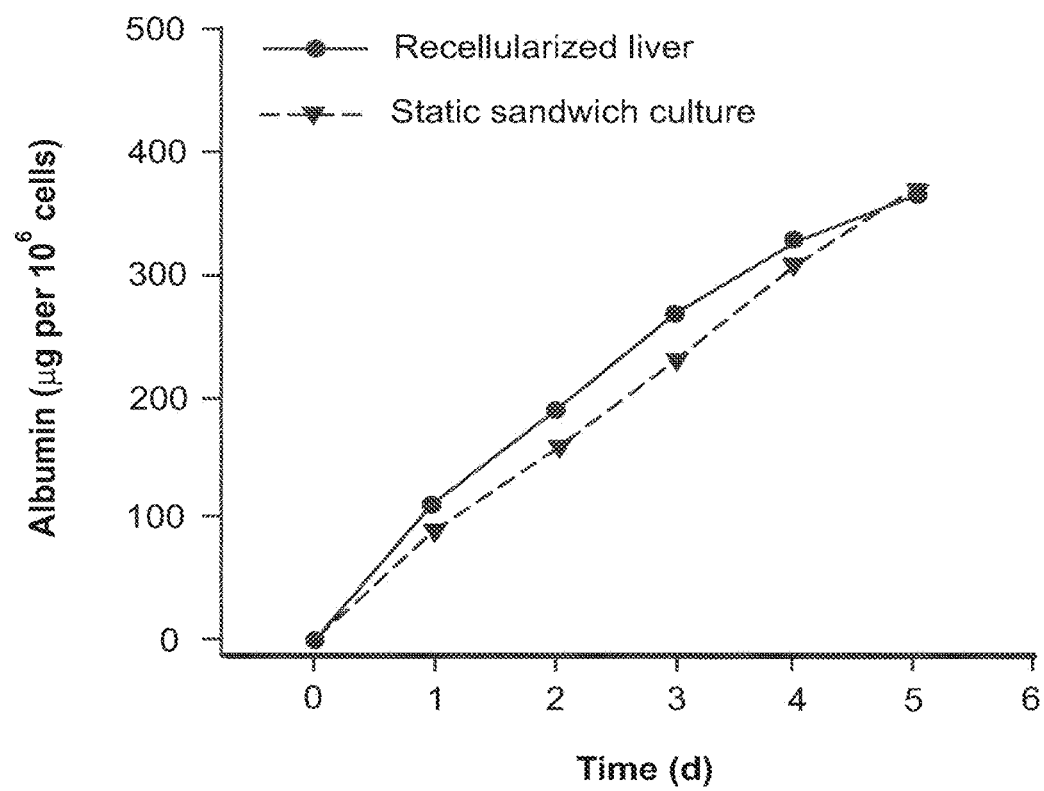

To assess the metabolic activity of engrafted hepatocytes, hepatocyte albumin production and urea synthesis was quantified as depicted in FIGS. 31A and 31B. The cumulative urea levels in the recellularized liver system were statistically higher than ho hepatocyte sandwich culture during the 5 day culture period (p=0.0017). The difference in cumulative albumin levels was statistically not significant (p=0.0176). Albumin production rate by the recellularized liver graft was 27.6±7.0 μg million per cells per day as compared to 140 μg million per cells per day by the normal adult rat liver as discussed in R. Hoffenberg, "Measurement of the synthesis of liver-produced plasma proteins with particular reference to dietary protein and amino acid supply," 123 Biochem. J. 3P (1972).

Figure 32A:
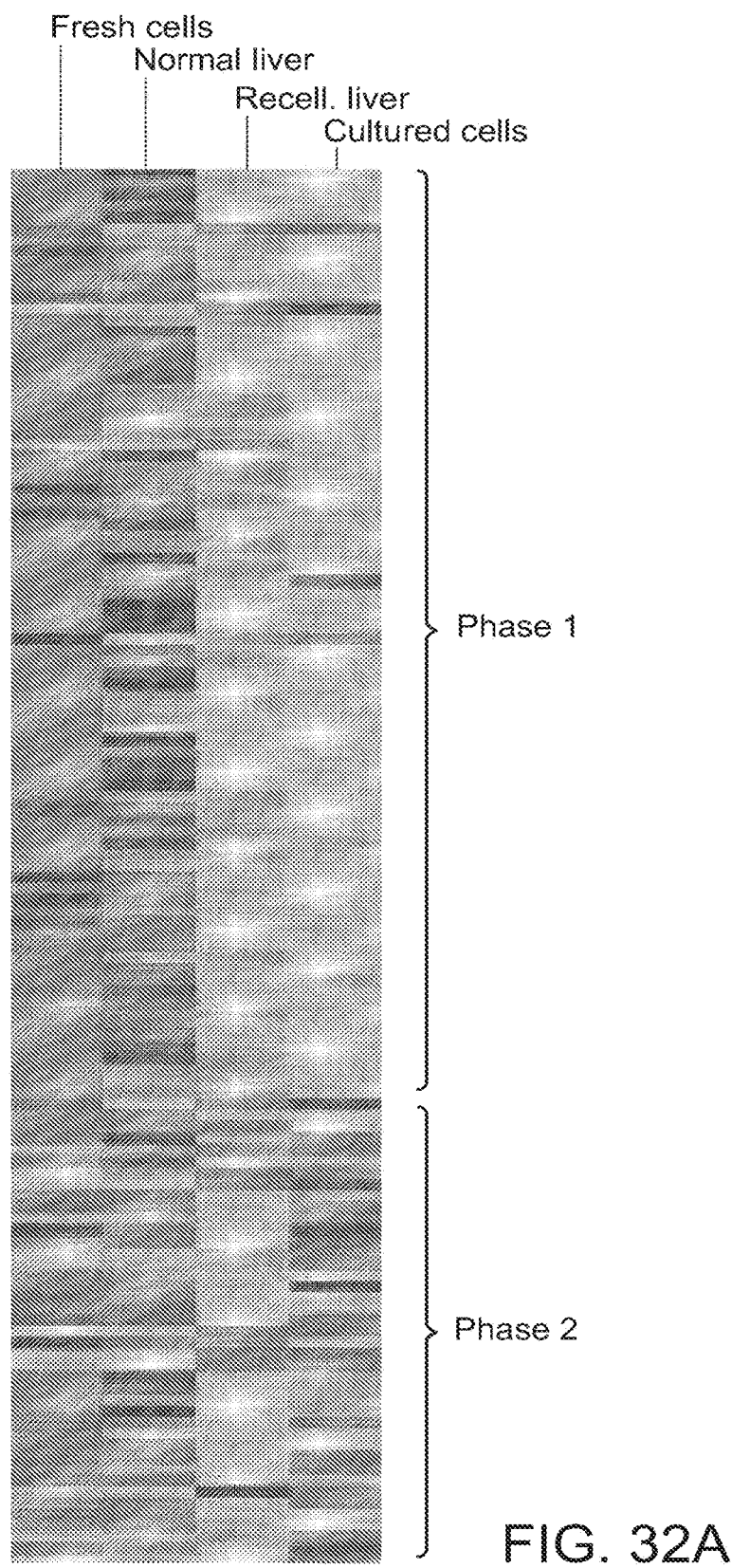
FIG. 32A depicts a gene expression analysis of hepatocytes in a recellularized liver graft after two days of culture compared to a normal liver, fresh hepatocytes, and sandwich culture hepatocytes after two days of culture for phase I and phase II drug metabolism enzymes.
Figure 32B:
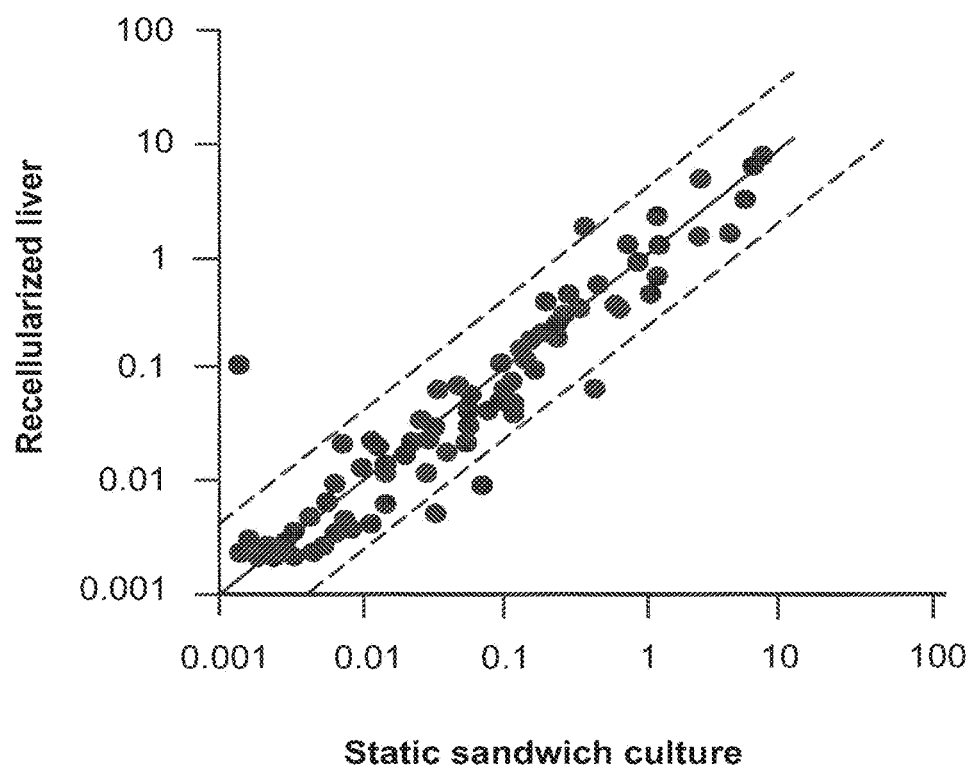
FIG. 32B is a scatter plot comparing gene expression of phase I and phase II drug metabolism enzymes for a recellularized liver graft and sandwich culture hepatocytes after two days of culture.
Figure 33A:
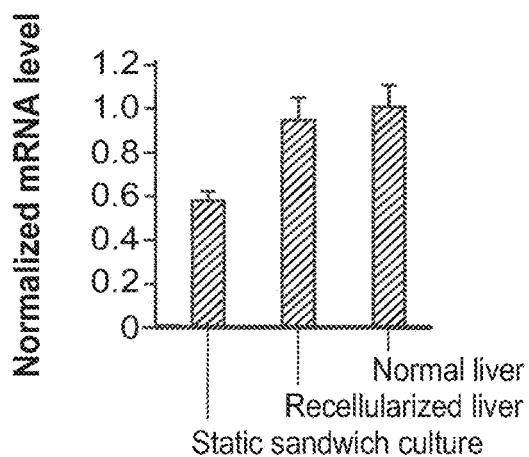
FIGS. 33A-33F are bar graphs of gene expression of cyp2c11, Gstm2, Ugt1a1, Cyp1a1, Adh1, and Cyp3a18, respectively. All error bars represent the standard error of the mean (n=3).
Figure 33B:
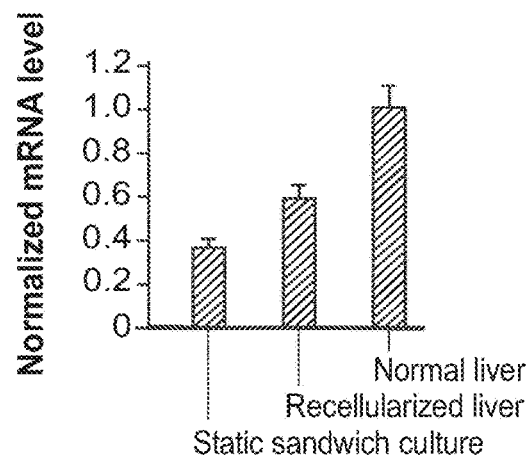
Figure 33C:
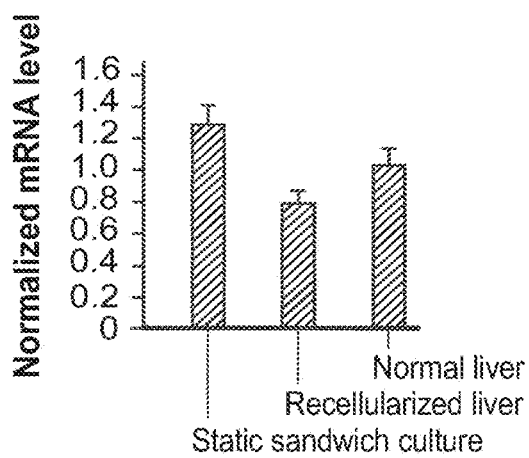
Figure 33D:
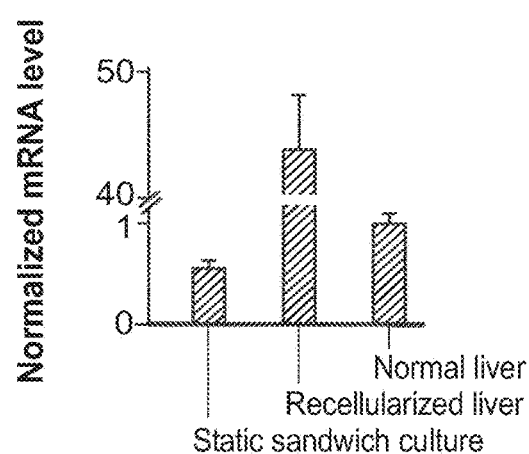
Figure 33E:
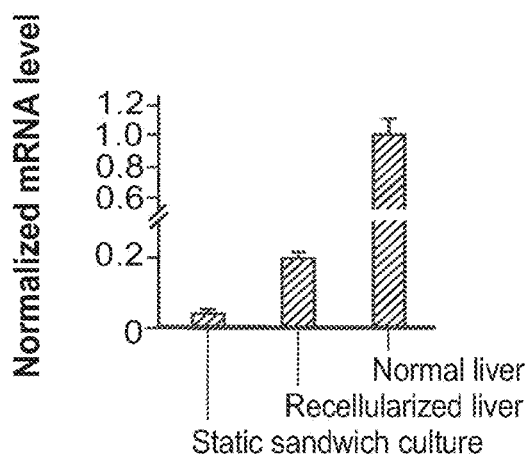
Figure 33F:
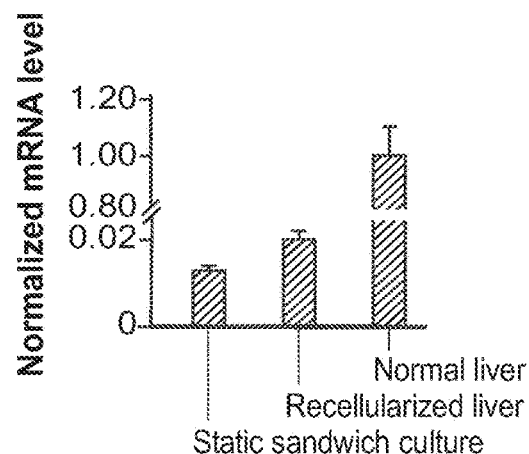

As depicted in FIGS. 32A and 32B, analysis of the expression of drug metabolism enzymes via quantitative Real Time Polymerase Chain Reaction (RT-PCR) at 2 days revealed that expression levels of phase I and phase II drug metabolism enzymes in the recellularized liver were similar to those measured in sandwich hepatocyte cultures (p=0.0499). As expected at this stage in culture and depicted in FIG. 32A, gene transcription levels were overall much lower than those of freshly isolated hepatocytes. However, Cyp2c11 (encoding cytochrome P450, subfamily 2, polypeptide 11) Gstm2 (glutathione S-transferase mu 2), Ugt1a1 (encoding UDP glucuronosyltransferase-1 family, polypeptide A1) and Cyp1a1 (encoding cytochrome P450, family-1, subfamily a, polypeptide 1) were expressed in the recellularized liver at similar levels to those in normal liver as depicted in FIGS. 33A-33D. Adh1 (encoding alcohol dehydrogenase-1) and Cyp3a18 (encoding cytochrome P450, family 3, subfamily a, polypeptide 18) expression levels were higher in recellularized liver than in the sandwich plate culture control, although they were much lower than in normal liver as depicted in FIGS. 33E and 33F. Primary hepatocytes are known to require between 7 to 10 days in culture before their metabolic activity and gene transcription levels stabilize as discussed in S. R. Khetani & S. N. Bhatia, "Microscale culture of human liver cells for drug development," 26 Nature Biochemistry 20-26 (2008).

WORKING EXAMPLE #8

Seeding of Non-Parenchymal Cells

Seeding of a non-parenchymal component to the recellularized liver graft was demonstrated by incorporating microvascular endothelial cells (ECs) to the hepatocyte-repopulated graft, and testing by perfusion-culture for up to 5 days to allow for EC engraftment. Histological analysis showed that endothelial cells were capable of lining the vasculature encircled by hepatocytes at 3 days of culture. Hepatocytes remained viable as indicated by TUNEL staining and immunohistochemistry.

In order to test the scalability of the seeding approach as well as the limits of the perfusion-culture system, the median lobe of DLM was repopulated with 200 million hepatocytes and perfused with a culture medium for 10 days. This cellular amount corresponds to approximately 20% of rat's liver mass and is more than double the minimum hepatic mass necessary for therapeutic interventions. In these studies, 50 million hepatocytes were injected at each of the four steps mentioned above in the context of FIG. 25. The metabolic activity of the recellularized liver graft was assessed through albumin production, urea secretion and total bite acid synthesis and the cumulative levels of production of these metabolites were found to be at similar levels to static sandwich culture controls (p=0.5249, 0.5271, and 0.0114, respectively) indicating the scalability of methods described herein as well as the usability of the perfusion-culture system described herein as an in vitro model.

WORKING EXAMPLE #9

Transplantation of Recellularized Liver Grafts

The functional vascular structure demonstrated herein enables transplantation of the recellularized liver graft by connecting the graft to the blood supply, thereby allowing for the transplantation of a critical hepatocyte mass while avoiding ischemic damage due to poor graft perfusion.

Figure 34:
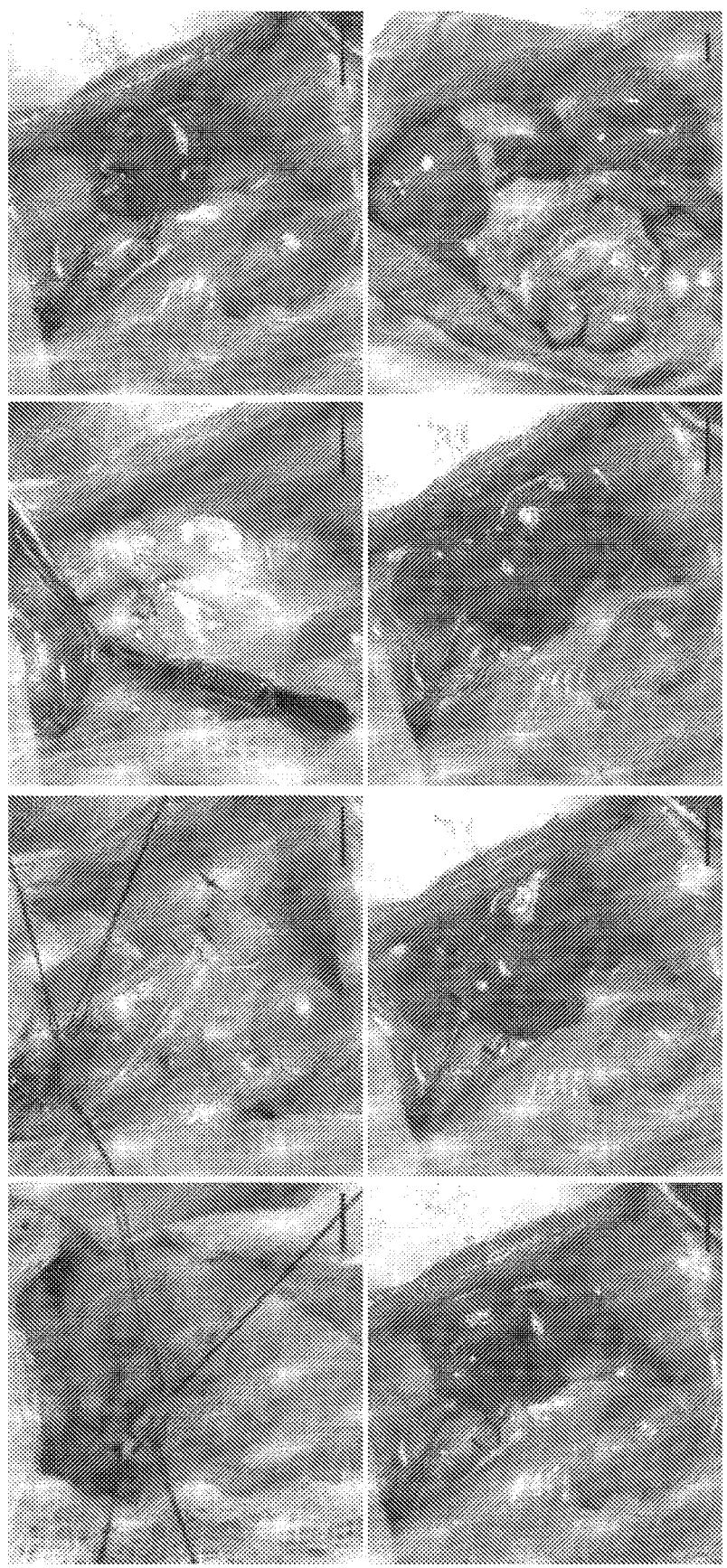
FIG. 34 is a series of representative images of recellularized liver graft transplantation. The top row depicts (from left to right): a transplant site, a recellularized graft at the transplant site, a transplanted graft before blood reperfusion, and a graft after declamping the renal artery. The bottom row depicts (from left to right): a transplanted graft at one minute after clamping, a transplanted graft at two minutes after clamping, a transplanted graft at four minutes after clamping, and an auxiliary recellularized liver graft in contrast with the native liver.
Figure 35:
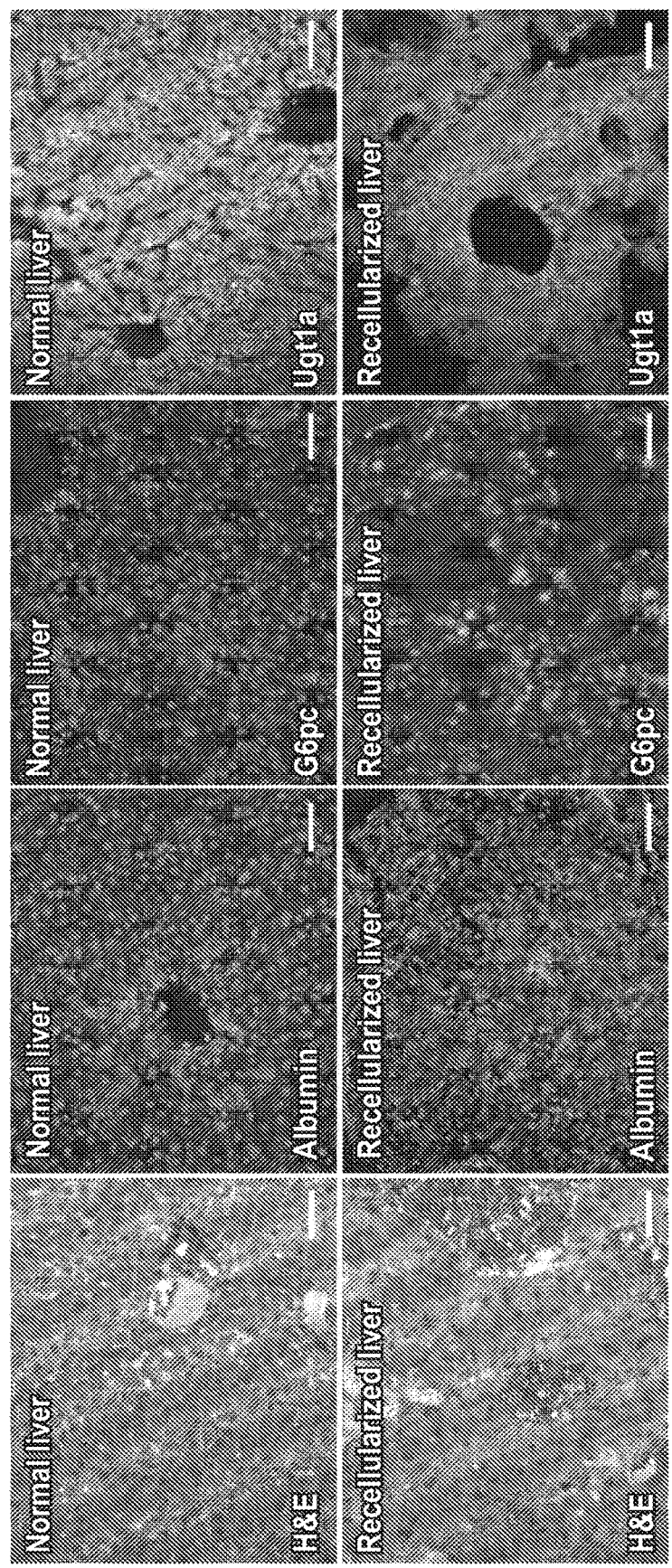
FIG. 35 is a comparison of a normal liver (top row) and a recellularized liver graft (bottom row) produced through immunostaining eight hours after transplantation for (from left to right across each row) hematoxylin and eosin, albumin (red), G6pc (red), and Ugt1a (green). Sections were counterstained with Hoescht 33258 (blue). The scale bars represent 100 µm.

Briefly, recipient animals underwent unilateral nephrectomy to prepare a viable site for auxiliary liver graft transplantation. The renal vein and artery were used to as ports to create blood flow within the graft. Upon unclamping of the artery, the graft was perfused, quickly filling with blood, and appropriate efflux was established within 5 minutes as depicted in FIG. 34. The recellularized graft was kept in vivo for 8 hours prior to harvesting for further analysis. TUNEL staining revealed that there was minimal damage to the hepatocytes due to the arterial blood flow and consequent shear stress during 8 h of transplantation. 19.7±13.7% of cells were TUNEL-positive after transplantation as compared 21.4±5.8% of cells before transplantation (p=0.55). Histological staining indicated that the hepatocytes retained bath normal morphology and their parenchymal positions as depicted in the leftmost panes of FIG. 35. Immunohistochemical staining for albumin, G6pc, and Ugt1a confirmed that hepatic function was also retained in the transplanted grafts with minimal indications of ischemic damage as depicted in FIG. 35.

To investigate early graft function beyond 8 hours, an ex vivo whole blood perfusion technique that has been shown to be representative of early graft performance and predict primary graft failure in an orthotopic rat liver transplant model in H. Tolbloom, et al., "Recovery of Warm Ischemic Rat Liver Grafts by Normothermic Extracorporeal Perfusion," 87 Transplantation 170-77 (2009) was adopted as a surrogate model of transplantation. Ex vivo perfusion system was similar to the in vitro perfusion described herein except that the perfusate consisted of whole rat blood diluted with perfusion medium (hematocrit 20%). The recellularized liver graft was perfused for 24 hours during which the blood was replenished three times at eight-hour intervals to maintain the hematocrit level at 20%. TUNEL staining and histological analysis showed that hepatocytes remained viable (22.6±13.8% TUNEL positive cells) and preserved their morphology and parenchymal position at the end of ex vivo blood perfusion. In addition, hepatocytes remained metabolically active during the 24 hours of ex vivo blood perfusion as evidenced by urea and albumin secretion.

EQUIVALENTS

The functions of several elements may, in alternative embodiments, be carried out by fewer elements, or a single element. Similarly, in some embodiments, any functional element may perform fewer, or different, operations than those described with respect to the illustrated embodiment. Also, functional elements (e.g., modules, computers, and the like) shown as distinct for purposes of illustration may be incorporated within other functional elements, separated in different hardware or distributed in a particular implementation.

While certain embodiments according to the invention have been described, the invention is not limited to just the described embodiments. Various changes and/or modifications can be made to any of the described embodiments without departing from the spirit or scope of the invention. Also, various combinations of elements, steps, features, and/or aspects of the described embodiments are possible and contemplated even if such combinations are not expressly identified herein.

INCORPORATION BY REFERENCE

The entire contents of all patents, published patent applications, and other references cited herein are hereby expressly incorporated herein in their entireties by reference.

The invention claimed is:

1. A method of recellularizing a liver of an adult subject with hepatocytes comprising:
   (a) decellularizing the liver by perfusing the liver with a perfusate comprising (i) one or more oxygen carriers, (ii) a collagenase, and (iii) one or more anti-inflammatory agents to generate a decellularized liver;
   (b) isolating adult cells from the perfusate; and
   (c) infusing the decellularized liver with hepatocytes, thereby recellularizing the decellularized liver with the hepatocytes.

2. The method of claim 1, wherein the liver is a mammalian liver.

3. The method of claim 1, wherein the liver is a human liver.

4. The method of claim 1, wherein the adult cells are selected from the group consisting of: hepatocytes, endothelial cells, cholangiocytes (bile duct cells), Kupffer cells, stellate cells, and smooth muscle cells.

5. The method of claim 1, wherein the liver is ischemic.

6. The method of claim 1, wherein the one or more oxygen carriers include erythrocytes.

7. The method of claim 1, wherein the perfusate is a normothermic perfusate.

8. The method of claim 1, wherein the perfusate is a room temperature perfusate.

9. The method of claim 1, wherein the perfusate is a hypothermic perfusate.

10. The method of claim 1, further comprising culturing the isolated adult cells.

11. The method of claim 1, wherein the step of isolating the adult cells from the perfusate includes filtering the perfusate after the perfusate has been perfused through the liver to isolate the adult cells.

12. The method of claim 11, wherein the filtering the perfusate step comprises filtering the perfusate through one or more mesh filters to isolate the adult cells.

13. The method of claim 12, wherein the one or more mesh filters have pore sizes ranging from about 1 μm to about 1000 μm.

14. The method of claim 1, wherein the step of isolating the adult cells from the perfusate includes performing density centrifugation on the perfusate after the perfusate has been perfused through the liver to isolate the adult cells.

15. The method of claim 1, further comprising circulating the perfusate through a dialyzer during step (a).

16. The method of claim 1, wherein the liver is a damaged liver.

17. The method of claim 1, wherein the perfusate improves the vitality of the adult cells.

18. The method of claim 1, wherein the perfusate, as provided to the liver, further comprises one or more substrates for metabolism.

19. The method of claim 18, wherein the one or more substrates for metabolism are selected from the group consisting of: a carbohydrate; lactate; a fatty acid; and a vitamin.

20. The method of claim 1, wherein the perfusate, as provided to the liver, further comprises an amino acid.

21. The method of claim 19, wherein the carbohydrate is glucose.

22. The method of claim 1, wherein the one or more anti-inflammatory agents is selected from the group consisting of: hydrocortisone, an antihistamine, and a non-steroidal anti-inflammatory drug (NSAID).

23. The method of claim 1, further comprising transplanting the recellularized liver into a recipient after step (c).

* * * * *